United States Patent
Gu et al.

(10) Patent No.: US 12,258,317 B2
(45) Date of Patent: Mar. 25, 2025

(54) ISOQUINOLINONE COMPOUND FOR INHIBITING SSAO/VAP-1, AND USE THEREOF

(71) Applicant: SUNSHINE LAKE PHARMA CO., LTD., Guangdong (CN)

(72) Inventors: Zheng Gu, Dongguan (CN); Jianhao Li, Dongguan (CN); Weihua Wang, Dongguan (CN); Haoxiong Qin, Dongguan (CN); Xinshan Deng, Dongguan (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 780 days.

(21) Appl. No.: 17/608,842

(22) PCT Filed: May 20, 2020

(86) PCT No.: PCT/CN2020/091184
§ 371 (c)(1),
(2) Date: Nov. 4, 2021

(87) PCT Pub. No.: WO2020/233583
PCT Pub. Date: Nov. 26, 2020

(65) Prior Publication Data
US 2022/0315536 A1     Oct. 6, 2022

(30) Foreign Application Priority Data

May 20, 2019 (CN) .......................... 201910418254.8

(51) Int. Cl.
| C07D 217/24 | (2006.01) |
| A61P 1/16 | (2006.01) |
| C07D 401/06 | (2006.01) |
| C07F 9/38 | (2006.01) |
| C07F 9/40 | (2006.01) |

(52) U.S. Cl.
CPC .............. *C07D 217/24* (2013.01); *A61P 1/16* (2018.01); *C07D 401/06* (2013.01); *C07F 9/3817* (2013.01); *C07F 9/4006* (2013.01)

(58) Field of Classification Search
CPC ........ C07D 217/24; C07D 401/06; A61P 1/16
See application file for complete search history.

(56) References Cited

U.S. PATENT DOCUMENTS

| 8,426,587 B2 | 4/2013 | McDonald et al. |
| 9,815,782 B2 | 11/2017 | Deodhar et al. |
| 10,160,723 B2 | 12/2018 | Deodhar et al. |
| 2006/0025438 A1 | 2/2006 | Salter-Cid et al. |
| 2020/0087248 A1 | 3/2020 | Zhu et al. |
| 2020/0377461 A1 | 12/2020 | Gu et al. |

FOREIGN PATENT DOCUMENTS

| WO | WO-2013163675 A1 * | 11/2013 | ........... A61K 31/166 |
| WO | WO-2018196677 A1 * | 11/2018 | ........... A61K 31/166 |
| WO | 2019/024924 A1 | 2/2019 | |

OTHER PUBLICATIONS

Kumar, G.N. and Surapaneni, S. (2001), Role of drug metabolism in drug discovery and development. Med. Res. Rev., 21: 397-411. (Year: 2001).*
Brown, N. Bioisosterism in medicinal chemistry. 2012, Bioisosteres in medicinal chemistry, 1-14. (Year: 2012).*
Foot, J. S., et al. J. Pharmacol. Exp. Ther. 2013, 347:365-374. (Year: 2013).*
Healy, A. M., et al. Advanced Drug Delivery Reviews. 2017, 117, 25-46. (Year: 2017).*
Zhu, J. WO 2018196677. English translation. (Year: 2018).*
Rautio, J., et al. Nature Reviews Drug Discovery. 2018, 17, pp. 559-587. (Year: 2018).*
Li, H., et al. Front. Pharmacol. 2021, 12:679707. (Year: 2021).*
Metabolite. Merriam Webster. Online dictionary. Web. pp. 1-10. (Year: 2024).*
Aug. 24, 2020 International Search Report issued in International Patent Application No. PCT/CN2020/091184.
Aug. 24, 2020 Written Opinion issued in International Patent Application No. PCT/CN2020/091184.
S. Karim et al. "Vascular Adhesion Protein-1 (VAP-1) Modulates Glucose and Lipid Uptake in Non-Alcoholic Fatty Liver Disease (NAFLD)". Gut, vol. 60, No. Suppl 2, Sep. 30, 2011, pp. A40-A41.

* cited by examiner

*Primary Examiner* — Eric Olson
*Assistant Examiner* — Samuel L Galster
(74) *Attorney, Agent, or Firm* — Oliff PLC

(57) ABSTRACT

An isoquinolinone compound acts as an inhibitor of semicarbazide-sensitive oxidase (SSAO) and/or vascular adhesion protein-1 (VAP-1), and the use thereof, and further relates to a pharmaceutical composition containing the compound. The compound or the pharmaceutical composition can be used to prepare a drug for preventing, treating or ameliorating inflammation and/or inflammation-related diseases, diabetes and/or diabetes-related diseases in patients, and especially can be used to prepare a drug for preventing, treating or ameliorating non-alcoholic fatty liver diseases in patients.

20 Claims, No Drawings

ISOQUINOLINONE COMPOUND FOR INHIBITING SSAO/VAP-1, AND USE THEREOF

CROSS-REFERENCE TO RELATED APPLICATION

This is a U.S. national stage application of the International Patent Application No. PCT/CN2020/091184, filed May 20, 2020, which claims the priority and benefits of Chinese Patent Application No. 201910418254.8, filed with the State Intellectual Property Office of China on May 20, 2019, which is incorporated herein by reference in its entirety.

FIELD OF THE INVENTION

The invention belongs to the pharmaceutical field, specifically, it relates to an isoquinolinone compound as an inhibitor of semicarbazide-sensitive amine oxidase (SSAO) and/or vascular adhesion protein-1 (VAP-1), preparation method thereof, a pharmaceutical composition containing the compound and pharmaceutical uses of the compound or pharmaceutical composition thereof. More in particular, the invention relates to the compound having Formula (I) or a pharmaceutically acceptable salt thereof, or a stereoisomer, a geometric isomer, and a pharmaceutical composition containing the compound, further relates to use of the compound and pharmaceutical composition in the manufacture of a medicament for preventing, treating or ameliorating inflammation and/or a disease related to inflammation, diabetes and/or a disease related to diabetes, especially in the manufacture of a medicament for preventing, treating or ameliorating patients' non-alcoholic fatty liver disease.

BACKGROUND OF THE INVENTION

Amine oxidase (AO) is a kind of protein with special biological functions, which exists widely in organisms, for example, in higher animals such as human and microbial cells. It can metabolize various endogenous or exogenous monoamines, diamines and polyamines. There are two main kinds of amine oxidases that are well known. One is copper-containing amine oxidases, which mainly include semicarbazide-sensitive amine oxidase (SSAO) and diamine oxidase (DAO); the other is flavin-containing amine oxidases, which mainly include monoamine oxidase and polyamine oxidase. Wherein semicarbazide-sensitive amine oxidase (SSAO) is an amine oxidase which contains divalent copper ions, takes 6-hydroxydopoquinone as coenzyme, and is particularly sensitive to semicarbazide, mainly exists in the form of dimer. Diamine oxidase (DAO) is mainly expressed in kidney, placenta, intestine and seminal vesicle (Elmore et al, 2002). It only acts on diamine, especially histamine, so it is also called histamine oxidase. Monoamine oxidase is divided into Monoamine Oxidase A (MAO-A) and Monoamine Oxidase B (MAO-B), which mainly exist in the mitochondria of most cells and use covalently bound flavin adenine dinucleotide (FAD) as the cofactor. Polyamine oxidase is another FAD-dependent amine oxidase which oxidatively deaminates spermine and spermidine. SSAO is different from MAO-A and MAO-B in terms of their substrates, inhibitors, cofactors, subcellular localization and function, it is a copper dependent amine oxidase that uses substances other than FAD, such as trihydroxyphenylalanine quinone (TPQ), as cofactors.

SSAO widely exists in the tissues with rich vascular content in mammals. It mainly exists in two forms, one is soluble form, which mainly exists in circulating blood; the other is membrane binding form, which widely distributes in organs and tissues, especially in fat cells, vascular endothelial cells and smooth muscle cells. SSAO is a multifunctional enzyme, and its pathophysiological functions vary with the tissue distribution of SSAO. In adipocytes and smooth muscle cells, SSAO can promote the transference of glucose transporter 4 (GLUT4) from adipocytes to cell membrane, thereby regulating glucose transport. In endothelial cells, SSAO exists in the form of vascular adhesion protein-1 (VAP-1), which mediates the adhesion and exudation of leukocytes and endothelial cells and plays a role in inflammatory.

VAP-1 is an endothelial adhesion molecule with dual functions. On the one hand, it is an adhesion molecule of lymphocytes, which promotes the adhesion of lymphocytes to vascular endothelium; on the other hand, VAP-1 has the function of enzyme, which can catalyze primary amines into corresponding aldehydes. VAP-1 is encoded by AOC3 gene located on human chromosome 17. VAP-1 protein may exist in plasma in a form of a solute, and also may exist on the surface of endothelial cells, adipocytes and smooth muscle cells in a form bound to membranes. The cloning of VAP-1 antigen revealed that it belongs to semicarbazide sensitive amine oxidase (Smith D. J, Salmi M, Bono P, et al. J I. *J Exp Med*, 1998,188(1): 17-27), which has the same structure as SSAO. Therefore, in recent years, researchers usually study SSAO by equating it with VAP-1. Therefore, the present invention describes the protein as SSAO/VAP-1.

Inflammation is the first response of the immune system to infection or irritation. The movement of leukocytes into tissue circulation is important for this process. Inappropriate inflammatory response can lead to local inflammation of other healthy tissues, which can lead to diseases such as rheumatoid arthritis, inflammatory bowel disease, multiple sclerosis, asthma, chronic obstructive pulmonary disease (COPD), eczema, psoriasis, etc. Leukocytes first adhere to the endothelium by binding with adhesion molecules before they pass through the vessel wall. Membrane-bound SSAO/VAP-1 is abundantly expressed in vascular endothelial cells such as high-efficiency vein endothelial cells (HVE) of lymphoid organs, and also expressed in hepatic sinusoidal endothelial cells (HSEC), smooth muscle cells and adipocytes. SSAO/VAP-1 contains sialic acid, which can induce cell adhesion, regulate leukocyte transport, participate in granulocyte exosmosis, and increase its level in the process of inflammation. The migration of neutrophils from blood to an inflammatory site is realized through the combination of adhesion molecules and vascular endothelial cells. It was found that the SSAO/VAP-1 activity in the pneumonia transgenic mice overexpressing SSAO/VAP-1 was increased, the accumulation of tissue protein-formaldehyde was formed, and the inflammatory cells in bronchoalveolar lavage fluid increased significantly. When SSAO/VAP-1 selective inhibitor was used to inhibit its activity, neutrophils, macrophage inflammatory protein 1-α and tumor necrosis factor-α in bronchoalveolar lavage fluid were reduced significantly, indicating that the deamination mediated by SSAO/VAP-1 has a significant effect on the occurrence and development of pneumonia (Smith D J, Salmi M, Bono P, et al, J Exp Med, 1998, 188: 17-27).

In the glucose transport system, insulin stimulates uptake and utilization of glucose by insulin sensitive tissues such as adipose tissue, myocardium, skeletal muscle by promoting the transfer of glucose transporter (GLUT) from the interior of the cell to its cell membrane. GLUT4 is an important GLUT subtype involved in glucose transport, which is mainly stored in the cytoplasm in the form of vesicles. In the study of the mechanism of SSAO/VAP-1 promoting glucose transportation and GLUT4 transference in adipocytes, Enrique-Tarancon et al. found that SSAO/VAP-1 in rat adipocytes was mainly expressed on the membrane surface of adipocytes in the form of membrane binding, and 18%-24% SSAO/VAP-1 was expressed in rat adipocytes, 3T3-L1 adipocytes and GLUT4 vesicles in rat skeletal muscle cells (Enrique-Tarancon Marti L, Morin N, et al. *J Blol Chem*, 1998, 273(14): 8025-8032). Mercader et al. administered FVB/n male mice with an inhibitor of SSAO/VAP-1 carbamide in drinking water for a long time, and found that the body mass index of FVB/n mice decreased by 31% and the body mass decreased by 15%, indicating that SSAO/VAP-1 inhibitor can inhibit fat deposition, reduce body mass and play an important role in regulating fat metabolism (Mereader J, Iffiu-Soltesz Z, Bour S, et al, *J Obes*, 2011, 2011:475-786).

The thickness of elastic layer of vascular wall is positively correlated with the ratio of SSAO/VAP-1 to elastin, which indicates that SSAO/VAP-1 may be involved in the organization of elastic fibers, and the characteristics and quantity of elastic fibers are important factors affecting the mechanical properties of arterial walls and the differentiation of vascular smooth muscle cells. The increase of SSAO/VAP-1 activity can lead to the destruction of the elastic fiber structure of aortic membrane, accompanied by the decrease of the grade of maturity of the elastin component and the increase of collagen, which will eventually cause the aorta to expand. The overexpression of SSAO/VAP-1 in smooth muscle can reduce arterial elasticity and impair the blood pressure regulating ability. The study found that although rodents are usually less prone to atherosclerosis, some mouse breeds, such as C57BL/6 mice, still have atherosclerotic plaques after administration of high cholesterol diet causing atherosclerosis. The activity of SSAO/VAP-1 was significantly increased in C57BL/6 mice which were prone to atherosclerosis. The deamination mediated by SSAO/VAP-1 may exist in the process of atherosclerosis and vascular disease.

In conclusion, SSAO/VAP-1 inhibitors have enzyme and adhesion activity and a significant correlation with incremental regulation in many inflammatory disorders, which make it a therapeutic target for all of the above diseases, and it has a good prospect of pharmaceutical development.

SUMMARY OF THE INVENTION

The present invention provides a novel compound having a good inhibition of SSAO/VAP-1 activity, the compound and a pharmaceutical composition thereof can be used in the manufacture of a medicament for preventing, treating or ameliorating inflammation and/or a disease related to inflammation, diabetes and/or a disease related to diabetes, a mental disorder, an ischemic disease, a vascular disease, fibrosis or tissue transplant rejection, in particular for preventing, treating or ameliorating nonalcoholic steatohepatitis in a patient.

In one aspect, provided herein is a compound having Formula (I) or a stereoisomer, a geometric isomer, a tautomer, an N-oxide, a solvate, a metabolite, a pharmaceutically acceptable salt or a prodrug thereof,

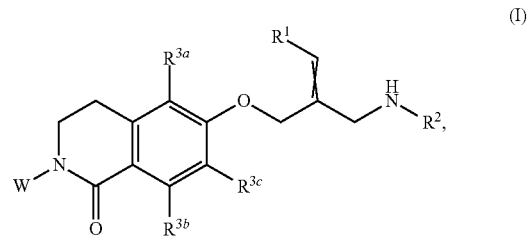

wherein, $R^1$ is F, Cl, Br or I;

$R^2$ is H, deuterium, $C_{1-6}$ alkyl, $C_{1-6}$ haloalkyl, $C_{3-6}$ cycloalkyl, 3-6 membered heterocyclyl, $C_{6-10}$ aryl, 5-6 membered heteroaryl or

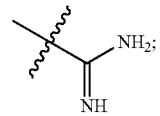

each of $R^{3a}$, $R^{3b}$ and $R^{3c}$ is independently H, deuterium, F, Cl, Br, I, CN, $NO_2$, —COOH, OH, $NH_2$, —C(=O)—$C_{1-6}$ alkyl, —C(=O)—$C_{1-6}$ alkoxy, $C_{1-6}$ alkyl, $C_{1-6}$ alkoxy, $C_{1-6}$ haloalkyl, $C_{1-6}$ haloalkoxy, hydroxy $C_{1-6}$ alkyl, amino $C_{1-6}$ alkyl, cyano $C_{1-6}$ alkyl, carboxy $C_{1-6}$ alkyl, $C_{3-6}$ cycloalkyl, 5-6 membered heterocyclyl, $C_{6-10}$ aryl or 5-6 membered heteroaryl;

W is -L-$R^4$ or —$(CR^aR^b)_t$P(=O)($R^5$)($R^6$);

L is —$(CR^aR^b)_p$—C(=O)—$NR^c$—, —$(CR^aR^b)_q$—S—, —$(CR^aR^b)_q$—S(=O)—, —$(CR^aR^b)_s$—S(=O)$_2$—, —$(CR^aR^b)_q$—S(=O)$_2$—$NR^c$— or —$(CR^aR^b)_q$—S(=O)—$NR^c$—;

each of q, p, s and t is independently 0, 1, 2, 3, 4 or 5;

each of $R^a$, $R^b$ and $R^c$ is independently H, deuterium, F, Cl, Br, I, CN, $NO_2$, —COOH, OH, $NH_2$, $C_{1-6}$ alkyl, $C_{1-6}$ alkoxy, $C_{1-6}$ haloalkyl, $C_{1-6}$ haloalkoxy, hydroxy $C_{1-6}$ alkyl, amino $C_{1-6}$ alkyl, cyano $C_{1-6}$ alkyl, carboxyl $C_{1-6}$ alkyl, $C_{3-6}$ cycloalkyl, 3-6 membered heterocyclyl, $C_{6-10}$ aryl or 5-6 membered heteroaryl;

$R^4$ is H, deuterium, $C_{1-8}$ alkyl, $C_{2-6}$ alkenyl, $C_{2-6}$ alkynyl, $C_{1-6}$ haloalkyl, $C_{3-6}$ cycloalkyl, 3-6 membered heterocyclyl, $C_{6-10}$ aryl or 5-6 membered heteroaryl, wherein each of the $C_{1-8}$ alkyl, $C_{2-6}$ alkenyl, $C_{2-6}$ alkynyl, $C_{1-6}$ haloalkyl, $C_{3-6}$ cycloalkyl, 3-6 membered heterocyclyl, $C_{6-10}$ aryl and 5-6 membered heteroaryl is independently unsubstituted or substituted with 1, 2, 3 or 4 $R^y$;

or $R^c$ and $R^4$ together with the nitrogen atom to which they are attached, form 3-6 membered heterocyclyl or 5-6 membered heteroaryl, wherein each of 3-6 membered heterocyclyl and 5-6 membered heteroaryl is independently unsubstituted or substituted with 1, 2, 3 or 4 $R^y$;

each of $R^5$ and $R^6$ is independently OH, $NH_2$, $C_{1-6}$ alkyl, $C_{1-6}$ alkoxy, $C_{1-6}$ alkylamino, $C_{3-6}$ cycloalkyl, $C_{3-6}$ cycloalkyloxy, $C_{3-6}$ cycloalkylamino, 3-6 membered heterocyclyl, 3-6 membered heterocyclyloxy, 3-6 membered heterocyclylamino, $C_{6-10}$ aryl, $C_{6-10}$ aryloxy, $C_{6-10}$ arylamino, 5-6 membered heteroaryl, 5-6 membered heteroaryloxy or 5-6 membered heteroarylamino, wherein each of the $C_{1-6}$ alkyl, $C_{1-6}$ alkoxy, $C_{1-6}$ alkylamino, $C_{3-6}$ cycloalkyl, $C_{3-6}$ cycloalkyloxy, $C_{3-6}$ cycloalkylamino, 3-6 membered heterocyclyl, 3-6 membered heterocyclyloxy, 3-6 membered heterocyclylamino, $C_{6-10}$ aryl, $C_{6-10}$ aryloxy, $C_{6-10}$ arylamino, 5-6 membered heteroaryl, 5-6 membered heteroaryloxy and 5-6 membered heteroarylamino is independently unsubstituted or substituted with 1, 2, 3 or 4 BY;

or $R^5$ and $R^6$ together with the phosphorus atom to which they are attached, form 3-6 membered heterocyclyl or 5-6 membered heteroaryl, wherein each of 3-6 membered heterocyclyl and 5-6 membered heteroaryl is independently unsubstituted or substituted with 1, 2, 3 or 4 $R^y$;

each $R^y$ is independently deuterium, F, Cl, Br, I, CN, $NO_2$, —COOH, OH, $NH_2$, —SH, —C(=O)—$C_{1-6}$ alkyl, —C(=O)—$C_{1-6}$ alkoxy, —S(=O)$_2$—$C_{1-6}$ alkyl, —S(=O)$_2$—$C_{1-6}$ alkylamino, $C_{1-6}$ alkyl, $C_{1-6}$ alkoxy, $C_{1-6}$ haloalkyl, $C_{1-6}$ haloalkoxy, hydroxy $C_{1-6}$ alkyl, amino $C_{1-6}$ alkyl, cyano $C_{1-6}$ alkyl, carboxy $C_{1-6}$ alkyl, $C_{3-6}$ cycloalkyl, 5-6 membered heterocyclyl, $C_{6-10}$ aryl or 5-6 membered heteroaryl.

In some other embodiments, $R^4$ is H, deuterium, $C_{1-6}$ alkyl, $C_{2-4}$ alkenyl, $C_{2-4}$ alkynyl, $C_{1-4}$ haloalkyl, $C_{3-6}$ cycloalkyl, 5-6 membered heterocyclyl, $C_{6-10}$ aryl or 5-6 membered heteroaryl, wherein each of the $C_{1-6}$ alkyl, $C_{2-4}$ alkenyl, $C_{2-4}$ alkynyl, $C_{1-4}$ haloalkyl, $C_{3-6}$ cycloalkyl, 5-6 membered heterocyclyl, $C_{6-10}$ aryl and 5-6 membered heteroaryl is independently unsubstituted or substituted with 1, 2, 3 or 4 BY;

or $R^c$ and $R^4$ together with the nitrogen atom to which they are attached, form 5-6 membered heterocyclyl or 5-6 membered heteroaryl, wherein each of 5-6 membered heterocyclyl and 5-6 membered heteroaryl is independently unsubstituted or substituted with 1, 2, 3 or 4 $R^y$;

In still other embodiments, $R^4$ is H, deuterium, methyl, ethyl, n-propyl, isopropyl, n-butyl, isobutyl, tert-butyl, n-pentyl, n-hexyl, vinyl, allyl, propenyl, ethynyl, —$CHF_2$, —$CF_3$, —$CH_2CHF_2$, —$CH_2CF_3$, cyclopropyl, cyclobutyl, cyclopentyl, cyclohexyl, pyrrolidinyl, pyrazolidinyl, tetrahydrofuranyl, tetrahydrothienyl, tetrahydropyranyl, piperidinyl, morpholinyl, thiomorpholinyl, piperazinyl, phenyl, naphthyl, furanyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the methyl, ethyl, n-propyl, isopropyl, n-butyl, isobutyl, tert-butyl, n-pentyl, n-hexyl, vinyl, allyl, propenyl, ethynyl, —$CHF_2$, —$CF_3$, —$CH_2CHF_2$, —$CH_2CF_3$, cyclopropyl, cyclobutyl, cyclopentyl, cyclohexyl, pyrrolidinyl, pyrazolidinyl, tetrahydrofuranyl, tetrahydrothienyl, tetrahydropyranyl, piperidinyl, morpholinyl, thiomorpholinyl, piperazinyl, phenyl, naphthyl, furanyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3 or 4 $R^y$;

or $R^c$ and $R^4$ together with the nitrogen atom to which they are attached, form pyrrolidinyl, pyrazolidinyl, imidazolidinyl, piperidinyl, morpholinyl, piperazinyl, pyrrolyl, pyridyl, pyrazolyl, imidazolyl, triazolyl, tetrazolyl, oxazolyl, isoxazolyl, oxadiazolyl, 1,3,5-triazinyl, pyrazinyl, thiazolyl or pyrimidinyl, wherein each of the pyrrolidinyl, pyrazolidinyl, imidazolidinyl, piperidinyl, morpholinyl, piperazinyl, pyrrolyl, pyridyl, pyrazolyl, imidazolyl, triazolyl, tetrazolyl, oxazolyl, isoxazolyl, oxadiazolyl, 1,3,5-triazinyl, pyrazinyl, thiazolyl or pyrimidinyl is independently unsubstituted or substituted with 1, 2, 3 or 4 $R^y$.

In some other embodiments, each of $R^5$ and $R^6$ is independently OH, $NH_2$, $C_{1-4}$ alkyl, $C_{1-4}$ alkoxy, $C_{1-4}$ alkylamino, $C_{3-6}$ cycloalkyl, $C_{3-6}$ cycloalkyloxy, $C_{3-6}$ cycloalkylamino, 5-6 membered heterocyclyl, 5-6 membered heterocyclyloxy, 5-6 membered heterocyclylamino, $C_{6-10}$ aryl, $C_{6-10}$ aryloxy, $C_{6-10}$ arylamino, 5-6 membered heteroaryl, 5-6 membered heteroaryloxy or 5-6 membered heteroarylamino, wherein each of the $C_{1-4}$ alkyl, $C_{1-4}$ alkoxy, $C_{1-4}$ alkylamino, $C_{3-6}$ cycloalkyl, $C_{3-6}$ cycloalkyloxy, $C_{3-6}$ cycloalkylamino, 5-6 membered heterocyclyl, 5-6 membered heterocyclyloxy, 5-6 membered heterocyclylamino, $C_{6-10}$ aryl, $C_{6-10}$ aryloxy, $C_{6-10}$ arylamino, 5-6 membered heteroaryl, 5-6 membered heteroaryloxy and 5-6 membered heteroarylamino is independently unsubstituted or substituted with 1, 2, 3 or 4 $R^y$;

or $R^5$ and $R^6$ together with the phosphorus atom to which they are attached, form 5-6 membered heterocyclyl or 5-6 membered heteroaryl, wherein each of 5-6 membered heterocyclyl and 5-6 membered heteroaryl is independently unsubstituted or substituted with 1, 2, 3 or 4 $R^y$.

In still other embodiments, each of $R^5$ and $R^6$ is independently OH, $NH_2$, methyl, ethyl, n-propyl, isopropyl, n-butyl, isobutyl, tert-butyl, methoxy, ethoxy, n-propyloxy, isopropyloxy, N-methylamino, N,N-dimethylamino, N-ethylamino, N,N-diethylamino, N-n-propylamino, N-isopropylamino, cyclopropyl, cyclobutyl, cyclopentyl, cyclohexyl, cyclopropyloxy, cyclobutyloxy, cyclopentyloxy, cyclohexyloxy, N-cyclopropylamino, N,N-dicyclopropylamino, N-cyclobutylamino, N-cyclopentylamino, N-cyclohexylamino, 5-6 membered heterocyclyl, 5-6 membered heterocyclyloxy, 5-6 membered heterocyclylamino, phenyl, phenyloxy, N-phenylamino, 5-6 membered heteroaryl, 5-6 membered heteroaryloxy or 5-6 membered heteroarylamino, wherein each of the methyl, ethyl, n-propyl, isopropyl, n-butyl, isobutyl, tert-butyl, methoxy, ethoxy, n-propyloxy, isopropyloxy, N-methylamino, N,N-dimethylamino, N-ethylamino, N,N-diethylamino, N-n-propylamino, N-isopropylamino, cyclopropyl, cyclobutyl, cyclopentyl, cyclohexyl, cyclopropyloxy, cyclobutyloxy, cyclopentyloxy, cyclohexyloxy, N-cyclopropylamino, N,N-dicyclopropylamino, N-cyclobutylamino, N-cyclopentylamino, N-cyclohexylamino, 5-6 membered heterocyclyl, 5-6 membered heterocyclyloxy, 5-6 membered heterocyclylamino, phenyl, phenyloxy, N-phenylamino, 5-6 membered heteroaryl, 5-6 membered heteroaryloxy and 5-6 membered heteroarylamino is independently unsubstituted or substituted with 1, 2, 3 or 4 $R^y$;

or $R^5$ and $R^6$ together with the phosphorus atom to which they are attached, form 5-6 membered heterocyclyl or 5-6 membered heteroaryl, wherein each of 5-6 membered heterocyclyl and 5-6 membered heteroaryl is independently unsubstituted or substituted with 1, 2, 3 or 4 $R^y$.

In some other embodiments, each $R^y$ is independently deuterium, F, Cl, Br, I, CN, $NO_2$, —COOH, OH, $NH_2$, —SH, —C(=O)—$C_{1-4}$ alkyl, —C(=O)—$C_{1-4}$ alkoxy, —S(=O)$_2$—$C_{1-4}$ alkyl, —S(=O)$_2$—$C_{1-4}$ alkylamino, $C_{1-4}$ alkyl, $C_{1-4}$ alkoxy, $C_{1-4}$ haloalkyl, $C_{1-4}$ haloalkoxy, hydroxy $C_{1-4}$ alkyl, amino $C_{1-4}$ alkyl, cyano $C_{1-4}$ alkyl, carboxy $C_{1-4}$ alkyl, $C_{3-6}$ cycloalkyl, 5-6 membered heterocyclyl, $C_{6-10}$ aryl or 5-6 membered heteroaryl.

In still other embodiments, each $R^y$ is independently deuterium, F, Cl, Br, I, CN, $NO_2$, —COOH, OH, $NH_2$, —SH, —C(=O)-methyl, —C(=O)-ethyl, —C(=O)-methoxy, —C(=O)-ethoxy, —S(=O)$_2$-methyl, —S(=O)$_2$-ethyl, —S(=O)$_2$-n-propyl, —S(=O)$_2$-isopropyl, —S(=O)$_2$-n-butyl, —S(=O)$_2$-tert-butyl, —S(=O)$_2$-methylamino, —S(=O)$_2$-ethylamino, —S(=O)$_2$-n-propylamino, —S(=O)$_2$-isopropylamino, —S(=O)$_2$-tert-butylamino, methyl, ethyl, n-propyl, isopropyl, n-butyl, isobutyl, tert-butyl, methoxy, ethoxy, n-propyloxy, isopropyloxy, —CHF$_2$, —CF$_3$, —CH$_2$CHF$_2$, —CH$_2$CF$_3$, trifluoromethoxy, hydroxymethyl, hydroxyethyl, aminomethyl, aminoethyl, cyanomethyl, cyanoethyl, carboxymethyl, cyclopropyl, cyclobutyl, cyclopentyl, cyclohexyl, 5-6 membered heterocyclyl, phenyl or 5-6 membered heteroaryl.

In some other embodiments, each of $R^a$, $R^b$ and $R^c$ is independently H, deuterium, F, Cl, Br, I, CN, NO$_2$, —COOH, OH, NH$_2$, $C_{1-4}$ alkyl, $C_{1-4}$ alkoxy, $C_{1-4}$ haloalkyl, $C_{1-4}$ haloalkoxy, hydroxy $C_{1-4}$ alkyl, amino $C_{1-4}$ alkyl, cyano $C_{1-4}$ alkyl, carboxyl $C_{1-4}$ alkyl, $C_{3-6}$ cycloalkyl, 5-6 membered heterocyclyl, $C_{6-10}$ aryl or 5-6 membered heteroaryl.

In still other embodiments, each of $R^a$, $R^b$ and $R^c$ is independently H, deuterium, F, Cl, Br, I, CN, NO$_2$, —COOH, OH, NH$_2$, methyl, ethyl, n-propyl, isopropyl, methoxy, ethoxy, —CHF$_2$, —CF$_3$, —CH$_2$CHF$_2$, —CH$_2$CF$_3$, trifluoromethoxy, hydroxymethyl, hydroxyethyl, aminomethyl, aminoethyl, cyanomethyl, carboxymethyl, cyclopropyl, cyclobutyl, cyclopentyl, cyclohexyl, 5-6 membered heterocyclyl, phenyl or 5-6 membered heteroaryl.

In some other embodiments, $R^2$ is H, deuterium, methyl, ethyl, n-propyl, isopropyl, n-butyl, isobutyl, tert-butyl, —CHF$_2$, —CF$_3$, —CH$_2$CHF$_2$, —CH$_2$CF$_3$, cyclopropyl, cyclobutyl, cyclopentyl, cyclohexyl, 5-6 membered heterocyclyl, phenyl or 5-6 membered heteroaryl or

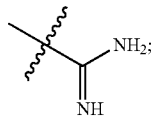

each of $R^{3a}$, $R^{3b}$ and $R^{3c}$ is independently H, deuterium, F, Cl, Br, I, CN, NO$_2$, —COOH, OH, NH$_2$, —C(=O)-methyl, —C(=O)-ethyl, —C(=O)-methoxy, —C(=O)-ethoxy, methyl, ethyl, n-propyl, isopropyl, n-butyl, isobutyl, tert-butyl, methoxy, ethoxy, —CHF$_2$, —CF$_3$, —CH$_2$CHF$_2$, —CH$_2$CF$_3$, trifluoromethoxy, hydroxymethyl, hydroxyethyl, aminomethyl, aminoethyl, cyanomethyl, carboxymethyl, cyclopropyl, cyclobutyl, cyclopentyl, cyclohexyl, 5-6 membered heterocyclyl, phenyl or 5-6 membered heteroaryl.

In some other embodiments, the pharmaceutically acceptable salt is hydrochloride, hydrobromide, phosphate, oxalate, maleate, tartrate, citrate, malate or methanesulfonate.

In other aspect, provided herein is a pharmaceutical composition comprising the compound disclosed herein.

In some embodiments, the pharmaceutical composition disclosed herein further comprises any one of pharmaceutically acceptable carriers, excipients, adjuvants, vehicles or combinations thereof.

In other aspect, provided herein is use of the compound or the pharmaceutical composition disclosed herein in the manufacture of a medicament for inhibiting SSAO/VAP-1.

In other aspect, provided herein is use of the compound or the pharmaceutical composition disclosed herein in the manufacture of a medicament for preventing, treating or ameliorating a disease related to SSAO/VAP-1 protein or regulated by SSAO/VAP-1 in a subject.

In other aspect, provided herein is a method of inhibiting SSAO/VAP-1, or preventing, treating or ameliorating a disease related to SSAO/VAP-1 protein or regulated by SSAO/VAP-1 comprising administering to the subject a therapeutically effective amount of the compound or the the pharmaceutical composition disclosed herein.

In other aspect, provided herein is the compound or the pharmaceutical composition disclosed herein for use in inhibiting SSAO/VAP-1, or preventing, treating or ameliorating a disease related to SSAO/VAP-1 protein or regulated by SSAO/VAP-1.

In some embodiments, wherein the disease related to SSAO/VAP-1 protein or regulated by SSAO/VAP-1 is inflammation and/or a disease related to inflammation, diabetes and/or a disease related to diabetes, a mental disorder, an ischemic disease, a vascular disease, fibrosis or tissue transplant rejection.

In other embodiments, the inflammation and/or a disease related to inflammation disclosed herein is arthritis, systemic inflammatory response syndrome, pyemia, synovitis, a Crohn's disease, ulcerative colitis, an inflammatory bowel disease, hepatopathy, a respiratory disease, an eye disease, a skin disease or neuritis.

In other embodiments, the diabetes and/or a disease related to diabetes disclosed herein is type I diabetes, type II diabetes, X syndrome, diabetic retinopathy, diabetic nephropathy, diabetic neuropathy or diabetic macular edema.

In other embodiments, the mental disorder disclosed herein is severe depression, bipolar depression or attention deficit hyperactivity disorder.

In other embodiments, the ischemic disease disclosed herein is apoplexia and/or a complication thereof, myocardial infarction and/or a complication thereof or damage of inflammatory cells to tissues after apoplexia.

In other embodiments, the fibrosis disclosed herein is hepatic fibrosis, cystic fibrosis, renal fibrosis, idiopathic pulmonary fibrosis or radiation-induced fibrosis.

In other embodiments, the vascular disease disclosed herein is atherosclerosis, chronic heart failure or congestive heart failure.

In still other embodiments, the arthritis disclosed herein is osteoarthritis, rheumarthritis, rheumatoid arthritis or juvenile rheumatoid arthritis.

In still other embodiments, the systemic inflammatory response syndrome disclosed herein is systemic inflammatory sepsis.

In still other embodiments, the inflammatory bowel disease disclosed herein is irritable bowel syndrome.

In still other embodiments, the hepatopathy disclosed herein is a liver autoimmune disease, autoimmune hepatitis, primary biliary cirrhosis, sclerosing cholangitis, autoimmune cholangitis, an alcoholic liver disease or a non-alcoholic fatty liver disease.

In still other embodiments, the non-alcoholic fatty liver disease is non-alcoholic simple fatty liver, non-alcoholic steatohepatitis, non-alcoholic fatty liver disease-related cryptogenic cirrhosis or primary liver cancer.

In still other embodiments, the respiratory disease disclosed herein is asthma, acute lung injury, acute respiratory distress syndrome, lung inflammation, a chronic obstructive pulmonary disease, bronchitis or bronchiectasis.

In still other embodiments, the eye disease disclosed herein is uveitis, iritis, retinitis, autoimmune ophthalmia, inflammation driven by angiogenesis and/or lymphogenesis, macular degeneration.

In still other embodiments, the skin disease disclosed herein is contact dermatitis, skin inflammation, psoriasis or eczema.

In still other embodiments, the neuritis disclosed herein is Parkinson's disease, Alzheimer's disease, vascular dementia, multiple sclerosis, chronic multiple sclerosis.

The foregoing merely summarizes certain aspects disclosed herein and is not intended to be limiting in nature. These aspects and other aspects and embodiments are described more fully below.

EXAMPLES

The invention provides an isoquinolinone compound having SSAO/VAP-1 inhibition activity, a preparation method thereof, a pharmaceutical composition containing the same, and uses thereof. Skilled in the art can learn from this article to properly improve the process parameters to implement the preparation method. Of particular note is that all similar substitutions and modifications to the skilled person is obvious, and they are deemed to be included in the present invention.

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention. One skilled in the art will recognize many methods and materials similar or equivalent to those described herein, which could be used in the practice of the present invention. The present invention is by no means limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and Smith et al., "March's Advanced Organic Chemistry", John Wiley & Sons, New York: 2007, the entire contents of which are hereby incorporated by reference.

The grammatical articles "a", "an" and "the", as used herein, are intended to include "at least one" or "one or more" unless otherwise indicated herein or clearly contradicted by the context. Thus, the articles used herein refer to one or more than one (i.e. at least one) articles of the grammatical objects. By way of example, "a component" means one or more components, and thus, possibly, more than one component is contemplated and may be employed or used in an implementation of the described embodiments.

Unless otherwise stated, the terms used in the specification and claims of the present invention have the following definitions.

The term "comprise" is an open expression, it means comprising the contents disclosed herein, but don't exclude other contents.

As described herein, compounds disclosed herein may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted". The terms "optionally" or "optional" mean that the subsequently described event or condition can but does not necessarily occur, and the description includes the case where the event or condition occurs, and the case where the event or condition does not occur. In general, unless otherwise indicated, an optionally substituted group may have a substituent at each substitutable position of the group. When more than one position in a given structure can be substituted with more than one substituent selected from a specified group, the substituent may be either the same or different at each position. The substituents described therein may be, but not limited to, deuterium, F, Cl, Br, I, CN, $NO_2$, —COOH, OH, $NH_2$, —SH, —C(=O)-alkyl, —C(=O)-alkoxy, —S(=O)$_2$-alkyl, —S(=O)$_2$-alkylamino, alkyl, haloalkyl, haloalkoxy, alkylamino, alkoxy, hydroxyalkyl, aminoalkyl, cyanoalkyl, carboxyalkyl, alkenyl, alkynyl, cycloalkyl, heterocyclyl, aryl, heteroaryl, cycloalkyloxy, cycloalkylamino, heterocyclyloxy, heterocyclylamino, aryloxy, arylamino, heteroaryloxy, heteroarylamino,

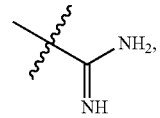

etc.

Furthermore, what need to be explained is that the phrases "each . . . is independently" and "each of . . . and . . . is independently", unless otherwise stated, should be broadly understood, which can mean that the specific options expressed by the same symbol are independent of each other in different groups; or the specific options expressed by the same symbol are independent of each other in same groups.

At each part of the present specification, substitutes of compounds disclosed herein are disclosed in groups or in ranges. It is specifically intended that the invention includes each and every individual subcombination of the members of such groups and ranges. For example, the term "$C_{1-6}$ alkyl" is especially $C_1$ alkyl (methyl), $C_2$ alkyl (ethyl), $C_3$ alkyl, $C_4$ alkyl, $C_5$ alkyl and $C_6$ alkyl disclosed independently, and "3-6 membered heterocyclyl" refers to 3 membered heterocyclyl, 4 membered heterocyclyl, 5 membered heterocyclyl and 6 membered heterocyclyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "halogen" refers to fluoro (F), chloro (Cl), bromo (Br), or iodo (I).

The term "alkyl" or "alkyl group" refers to a saturated linear or branched-chain monovalent hydrocarbon group of 1-20 carbon atoms, wherein the alkyl group is optionally substituted with one or more substituents described herein. In some embodiments, the alkyl group contains 1-10 carbon atoms. In other embodiments, the alkyl group contains 1-8 carbon atoms, i.e., $C_{1-8}$ alkyl. In other embodiments, the alkyl group contains 1-6 carbon atoms, i.e., $C_{1-6}$ alkyl. In still other embodiments, the alkyl group contains 1-4 carbon atoms, i.e., $C_{1-4}$ alkyl. In yet other embodiments, the alkyl group contains 1-2 carbon atoms, i.e., $C_{1-2}$ alkyl.

Some non-limiting examples of the alkyl group include, methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), isobutyl (i-Bu, —CH$_2$CH(CH$_3$)$_2$), sec-butyl (s-Bu, —CH(CH$_3$)CH$_2$CH$_3$), tert-butyl (t-Bu, —C(CH$_3$)$_3$), n-pentyl (—CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), n-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), n-heptyl and n-octyl, etc.

The term "alkenyl" refers to linear or branched-chain monovalent hydrocarbon radical of 2 to 12 carbon atoms with at least one site of unsaturation, i.e., a carbon-carbon, sp$^2$ double bond, wherein the alkenyl radical may be optionally substituted with one or more substituents described herein, and includes radicals having "cis" and "trans" orientations, or alternatively, "E" and "Z" orientations. In some embodiments, the alkenyl contains 2 to 8 carbon atoms. In other embodiments, the alkenyl contains 2 to 6 carbon atoms, i.e., $C_{2-6}$ alkenyl. In still other embodiments, the alkenyl contains 2 to 4 carbon atoms, i.e., $C_{2-4}$ alkenyl.

Some non-limiting examples of the alkenyl group include vinyl (—CH=CH$_2$), allyl (—CH$_2$CH=CH$_2$), propenyl (—CH=CHCH$_3$), butenyl (—CH=CHCH$_2$CH$_3$, —CH$_2$CH=CHCH$_3$, —CH$_2$CH$_2$CH=CH$_2$, —CH=C(CH$_3$)$_2$, —CH=C(CH$_3$)$_2$, —CH$_2$C(CH$_3$)=CH$_2$), pentenyl (—CH$_2$CH$_2$CH$_2$CH=CH$_2$, —CH$_2$CH$_2$CH=CHCH$_3$, —CH$_2$CH$_2$CH=CHCH$_3$, —CH$_2$CH=CHCH$_2$CH$_3$, —CH=CHCH$_2$CH$_2$CH$_3$, —CH$_2$CH$_2$C(CH$_3$)=CH$_2$, —CH$_2$CH=C(CH$_3$)$_2$, —CH=CHCH(CH$_3$)$_2$, —C(CH$_2$CH$_3$)=CHCH$_3$, —CH(CH$_2$CH$_3$)CH=CH$_2$), and so on.

The term "alkynyl" refers to a linear or branched monovalent hydrocarbon radical of 2 to 12 carbon atoms with at least one site of unsaturation, i.e., a carbon-carbon, sp triple bond, wherein the alkynyl radical may be optionally substituted with one or more substituents described herein. In some embodiments, the alkynyl contains 2 to 8 carbon atoms. In other embodiments, the alkynyl contains 2 to 6 carbon atoms, i.e., $C_{2-6}$ alkynyl. In still other embodiments, the alkynyl contains 2 to 4 carbon atoms, i.e., $C_{2-4}$ alkynyl. Some non-limiting examples of the alkynyl group include ethynyl (—C≡CH), 1-propynyl (—C≡CH—CH$_3$), propargyl (—CH$_2$C≡CH), 1-butynyl, 2-butynyl, 1-pentynyl, 2-pentynyl, 3-methyl-1-butynyl, 1-hexynyl, 1-heptynyl and 1-octynyl, etc.

The term "alkoxy" refers to an alkyl group, as previously defined, attached to parent molecular moiety via an oxygen atom, i.e., alkyl-O—, wherein the alkoxy group may be optionally substituted with one or more substituents described in the present invention. In some embodiments, the alkoxy group contains 1-20 carbon atoms. In other embodiments, the alkoxy group contains 1-10 carbon atoms. In other embodiments, the alkoxy group contains 1-8 carbon atoms. In other embodiments, the alkoxy group contains 1-6 carbon atoms, i.e., $C_{1-6}$ alkoxy. In still other embodiments, the alkoxy group contains 1-4 carbon atoms, i.e., $C_{1-4}$ alkoxy. In yet other embodiments, the alkoxy group contains 1-3 carbon atoms, i.e., $C_{1-3}$ alkoxy.

Some non-limiting examples of the alkoxy group include, but are not limited to, methoxy (MeO, —OCH$_3$), ethoxy (EtO, —OCH$_2$CH$_3$), n-propyloxy (n-PrO, n-propoxy, —OCH$_2$CH$_2$CH$_3$), isopropyloxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-isopropyloxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like.

The term "cycloalkyloxy" refers to a cycloalkyl group, as previously defined, attached to parent molecular moiety via an oxygen atom, i.e., cycloalkyl-O—, wherein the cycloalkyloxy group may be optionally substituted with one or more substituents described in the present invention.

Examples of cycloalkyloxy groups include, but are not limited to, cyclopropyloxy

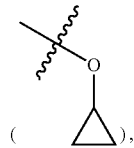

cyclobutyloxy

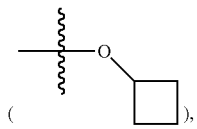 [SMILES: *OC1CCC1]

cyclopentyloxy

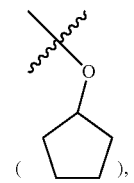

cyclohexyloxy

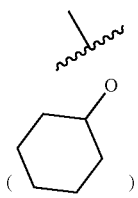

and the like.

The term "heterocyclyloxy" refers to a heterocyclyl group, as previously defined, attached to parent molecular moiety via an oxygen atom, i.e., heterocyclyl-O—, wherein the heterocyclyloxy group may be optionally substituted with one or more substituents described in the present invention. Examples of heterocyclyloxy groups include, but are not limited to,

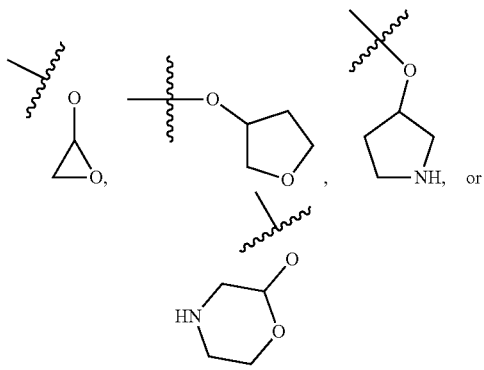

and the like.

The term "aryloxy" refers to an aryl group, as previously defined, attached to parent molecular moiety via an oxygen atom, i.e., aryl-O—, wherein the aryloxy group may be optionally substituted with one or more substituents described in the present invention. Examples of aryloxy groups include, but are not limited to, phenyloxy

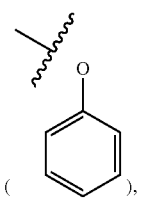

naphthyloxy

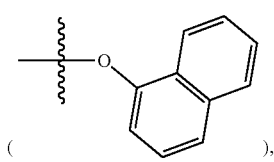 [SMILES: *Oc1cccc2ccccc12]

and the like.

The term "heteroaryloxy" refers to a heteroaryl group, as previously defined, attached to parent molecular moiety via an oxygen atom, i.e., heteroaryl-O—, wherein the heteroaryloxy group may be optionally substituted with one or more substituents described in the present invention. Examples of heteroaryloxy groups include, but are not limited to,

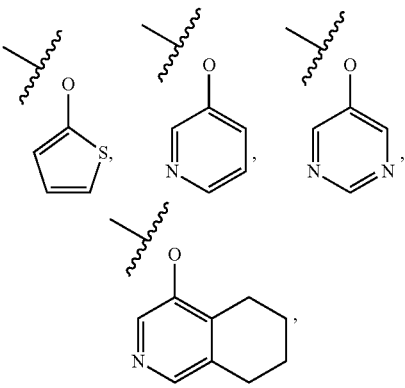

and the like.

The term "alkylamino" includes "N-alkylamino" and "N,N-dialkylamino", i.e., an amino group is independently substituted with one or two alkyl radicals and wherein the alkyl group is as defined herein. Wherein, the alkylamino group may be optionally substituted with one or more substituents disclosed herein. In some embodiments, the alkylamino group is one or two $C_{1-6}$ alkyl groups attached to a nitrogen atom, i.e., $C_{1-6}$ alkylamino. In some embodiments, the alkylamino group is one or two $C_{1-4}$ alkyl groups attached to a nitrogen atom, i.e., $C_{1-4}$ alkylamino. In some embodiments, the alkylamino group is one or two $C_{1-2}$ alkyl groups attached to a nitrogen atom, i.e., $C_{1-2}$ alkylamino. Examples of alkylamino groups include, but are not limited to, methylamino (N-methylamino), ethylamino (N-ethylamino), N,N-dimethylamino, N,N-diethylamino, n-propylamino (N-n-propylamino), isopropylamino (N-isopropylamino), tert-butylamino (N-tert-butylamino) and so on.

The term "cycloalkylamino" includes "N-cycloalkylamino" and "N,N-bicycloalkylamino", which refers to an amino group is independently substituted with one or two cycloalkyl groups. The cycloalkyl group is as defined herein, wherein the cycloalkylamino group may be optionally substituted with one or more substituents described in the present invention. Some non-limiting examples of cycloalkylamino group include cyclopropylamino (N-cyclopropylamino), N,N-dicyclopropylamino, cyclobutylamino (N-cyclobutylamino), cyclopentylamino (N-cyclopentylamino), cyclohexylamino (N-cyclohexylamino).

The term "heterocyclylamino" includes "N-heterocyclylamino" and "N,N-diheterocyclylamino", which refers to an amino group is substituted by one or two heterocyclyl groups. The heterocyclyl group is as defined herein, wherein the heterocyclylamino group may be optionally substituted by one or more substituents described in the present invention. Examples of heterocyclylamino include, but are not limited to, N-pyrrolidinylamino, and the like.

The term "arylamino" includes "N-arylamino" and "N,N-diarylamino", which refers to an amino group is substituted by one or two aryl groups. The aryl group is as defined herein, wherein the arylamino group may be optionally substituted by one or more substituents described in the present invention. Examples of arylamino include, but are not limited to, phenylamino (N-phenylamino), and the like.

The term "heteroarylamino" includes "N-heteroarylamino" and "N,N-diheteroarylamino", which refers to an amino group is substituted by one or two heteroaryl groups. The heteroaryl group is as defined herein, wherein the heteroarylamino group may be optionally substituted with one or more substituents described in the present invention. Examples of heteroarylamino include, but are not limited to, N-pyrimidinylamino, and the like.

The term "haloalkyl" refers to an alkyl group having one or more halogen substituents, wherein the haloalkyl group may be optionally substituted with one or more substituents disclosed herein. In some embodiments, the haloalkyl group contains 1-10 carbon atoms. In some embodiments, the haloalkyl group contains 1-8 carbon atoms. In other embodiments, the haloalkyl group contains 1-6 carbon atoms, i.e., $C_{1-6}$ haloalkyl. In other embodiments, the haloalkyl group contains 1-4 carbon atoms, i.e., $C_{1-4}$ haloalkyl. In still other embodiment, the haloalkyl group contains 1-3 carbon atoms, i.e., $C_{1-3}$ haloalkyl. In yet other embodiment, the haloalkyl group contains 1-2 carbon atoms, i.e., $C_{1-2}$ haloalkyl. Examples of haloalkyl groups include, but are not limited to, fluoromethyl (—$CH_2F$), difluoromethyl (—$CHF_2$), trifluoromethyl (—$CF_3$), fluoroethyl (—$CHFCH_3$, —$CH_2CH_2F$), difluoroethyl (—$CF_2CH_3$, —$CFHCFH_2$, —$CH_2CHF_2$), perfluoroethyl, fluoropropyl (—$CHFCH_3$, —$CH_2CHFCH_3$, —$CH_2CH_2CH_2F$), difluoropropyl (—$CF_2CH_2CH_3$, —$CFHCFHCH_3$, —$CH_2CH_2CHF_2$, —$CH_2CF_2CH_3$, —$CH_2CHFCH_2F$), trifluoropropyl, 1,1-dichloroethyl, 1,2-dichloropropyl, etc.

The term "haloalkoxy" refers to an alkoxy group having one or more halogen substituents, wherein the haloalkoxy group may be optionally substituted with one or more substituents disclosed herein. In some embodiments, the haloalkoxy group contains 1-10 carbon atoms. In some embodiments, the haloalkoxy group contains 1-8 carbon atoms. In other embodiments, the haloalkoxy group contains 1-6 carbon atoms, i.e., $C_{1-6}$ haloalkoxy. In other embodiments, the haloalkoxy group contains 1-4 carbon atoms, i.e., $C_{1-4}$ haloalkoxy. In still other embodiment, the haloalkoxy group contains 1-3 carbon atoms, i.e., $C_{1-3}$ haloalkoxy. In yet other embodiment, the haloalkoxy group contains 1-2 carbon atoms, i.e., $C_{1-2}$ haloalkoxy. Some non-limiting examples of the haloalkoxy group include trifluoromethoxy, difluoromethoxy, etc.

The term "hydroxyalkyl" refers to an alkyl group substituted with one or more hydroxy groups (—OH), wherein the alkyl group is as defined herein, wherein the hydroxyalkyl group may be optionally substituted with one or more substituents disclosed herein. In some embodiments, the hydroxyalkyl group in the present invention refers to $C_{1-6}$ alkyl substituted with one or more hydroxy groups (—OH), i.e., hydroxy $C_{1-6}$ alkyl; in some embodiments, the hydroxyalkyl group refers to $C_{1-4}$ alkyl substituted with one or more hydroxy groups (—OH), i.e., hydroxy $C_{1-4}$ alkyl; in some embodiments, the hydroxyalkyl group refers to $C_{1-2}$ alkyl substituted with one or more hydroxy groups (—OH), i.e., hydroxy $C_{1-2}$ alkyl. Examples of hydroxyalkyl groups include, but are not limited to, hydroxymethyl, hydroxyethyl (e.g., 2-hydroxyethyl), hydroxy-n-propyl (e.g., —$CH_2CH_2CH_2OH$), and the like.

The term "aminoalkyl" refers to an alkyl group substituted with one or more amino groups (—$NH_2$), wherein the alkyl group are as defined herein, wherein the aminoalkyl group may be optionally substituted with one or more substituents disclosed herein. In some embodiments, the aminoalkyl group in the present invention refers to $C_{1-6}$ alkyl substituted with one or more amino groups (—$NH_2$), i.e., amino $C_{1-6}$ alkyl; in some embodiments, the aminoalkyl group refers to $C_{1-4}$ alkyl substituted with one or more amino groups (—$NH_2$), i.e., amino $C_{1-4}$ alkyl; in some embodiments, the aminoalkyl group refers to $C_{1-2}$ alkyl substituted with one or more amino groups (—$NH_2$), i.e., amino $C_{1-2}$ alkyl. Examples of aminoalkyl groups include, but are not limited to, aminomethyl, aminoethyl (e.g., 2-aminoethyl), amino-n-propyl (e.g., —$CH_2CH_2CH_2NH_2$), and the like.

The term "cyanoalkyl" refers to an alkyl group substituted with one or more cyano groups (—CN), wherein the alkyl group are as defined herein, wherein the cyanoalkyl group may be optionally substituted with one or more substituents disclosed herein. In some embodiments, the cyanoalkyl group in the present invention refers to $C_{1-6}$ alkyl substituted with one or more cyano groups (—CN), i.e., cyano $C_{1-6}$ alkyl; in some embodiments, the cyanoalkyl group refers to $C_{1-4}$ alkyl substituted with one or more cyano groups (—CN), i.e., cyano $C_{1-4}$ alkyl; in some embodiments, the cyanoalkyl group refers to $C_{1-2}$ alkyl substituted with one or more cyano groups (—CN), i.e., cyano $C_{12}$ alkyl. Examples of cyanoalkyl groups include, but are not limited to, cyanomethyl, cyanoethyl (e.g., 2-cyanoethyl), and the like.

The term "carboxyalkyl" refers to an alkyl group substituted with one or more carboxy groups (—COOH), wherein the alkyl group are as defined herein, wherein the carboxyalkyl group may be optionally substituted with one or more substituents disclosed herein. In some embodiments, the carboxyalkyl group in the present invention refers to $C_{1-6}$ alkyl substituted with one or more carboxy groups (—COOH), i.e., carboxy $C_{1-6}$ alkyl; in some embodiments, the carboxyalkyl group refers to $C_{1-4}$ alkyl substituted with one or more carboxy groups (—COOH), i.e., carboxy $C_{1-4}$ alkyl; in some embodiments, the carboxyalkyl group refers to $C_{1-2}$ alkyl substituted with one or more carboxy groups (—COOH), i.e., carboxy $C_{1-2}$ alkyl. Examples of carboxyalkyl groups include, but are not limited to, carboxymethyl, carboxyethyl (e.g., 2-carboxyethyl), and the like.

The term "cycloalkyl" refers to a saturated ring having 3 to 12 ring carbon atoms as a monocyclic, bicyclic, or tricyclic ring system, which has one or more attachments attaching to the rest of the molecule, wherein the cycloalkyl group is optionally substituted with the substituents described in the present invention. In some embodiments, cycloalkyl is a ring system containing 3-10 ring carbon atoms, i.e., $C_{3-10}$ cycloalkyl; in still other embodiments, cycloalkyl is a ring system containing 3-8 ring carbon atoms, i.e., $C_{3-8}$ cycloalkyl; in yet other embodiments, cycloalkyl is a ring system containing 3-6 ring carbon atoms, i.e., $C_{3-6}$ cycloalkyl. Examples of cycloalkyl groups include, but are not limited to, cyclopropyl, cyclobutyl, cyclopentyl, cyclohexyl and the like.

The term "heterocyclyl" refers to a saturated or partially unsaturation, nonaromatic ring having 3 to 12 atoms as a monocyclic, bicyclic, or tricyclic ring system, in which at least one ring member is selected from nitrogen, sulfur and oxygen. Wherein, the heterocyclic group is non-aromatic and does not contain any aromatic ring, and the ring system has one or more connection points connected to the rest of the molecule. The heterocyclyl group may be optionally substituted with one or more substituents disclosed herein. The term "heterocyclyl" includes monocyclic, bicyclic or polycyclic fused, spiro or bridged heterocyclic ring systems. Bicyclic heterocyclic groups include bridged bicyclic heterocyclyl, fused bicyclic heterocyclyl and spiro bicyclic heterocyclyl. The terms "heterocyclyl", "heterocyclic group" and "heterocycle" are used interchangeably herein. Unless otherwise specified, the heterocyclyl group may be carbon or nitrogen linked, and a —CH$_2$— group can be optionally replaced by a —C(=O)— group. In which, the sulfur can be optionally oxygenized to S-oxide, and the nitrogen can be optionally oxygenized to N-oxide. In some embodiments, the heterocyclyl is a ring system composed of 3-10 ring atoms; in some embodiments, the heterocyclyl is a ring system composed of 5-10 ring atoms; in some embodiments, the heterocyclyl is a ring system composed of 5-8 ring atoms; in some embodiments, the heterocyclyl is a ring system composed of 6-8 ring atoms; in some embodiments, the heterocyclyl is a ring system composed of 5-6 ring atoms; in other embodiments, the heterocyclyl is a ring system composed of 3-6 ring atoms; in other embodiments, the heterocyclyl is a ring system composed of 3 ring atoms; in other embodiments, the heterocyclyl is a ring system composed of 4 ring atoms; in other embodiments, the heterocyclyl is a ring system composed of 5 ring atoms; in other embodiments, the heterocyclyl is a ring system composed of 6 ring atoms.

Examples of the heterocyclyl group include, but are not limited to, oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, tetrahydropyrrolyl, dihydropyrrolyl, tetrahydropyridinyl, tetrahydropyrimidinyl, tetrahydropyrazinyl, tetrahydropyridazinyl, etc. Some non-limiting examples of the heterocyclyl group wherein —CH$_2$— group is replaced by —C(=O)— moiety include 2-oxopyrrolidinyl, oxo-1,3-thiazolidinyl, 2-piperidinonyl, 3,5-dioxopiperidinyl, pyrimidinedione-yl, and the like. Some non-limited examples of the heterocyclyl group wherein the ring sulfur atom is oxidized is sulfolanyl and 1,1-dioxo-thiomorpholinyl. Bridged heterocyclyl groups include, but are not limited to, 2-oxabicyclo[2.2.2] octyl, 1-azabicyclo[2.2.2] octyl, 3-azabicyclo[3.2.1] octyl, etc.

The term "m-membered", where m is an integer typically describes the number of ring-forming atoms in a moiety where the number of ring-forming atoms is m. For example, piperidinyl is an example of a 6 membered heterocyclyl group and furanyl is an example of a 5 membered heteroaryl group. As another example, "3-6 membered heterocyclyl" refers to a heterocyclic group consisting of 3, 4, 5, or 6 atoms.

The term "aryl" refers to monocyclic, bicyclic and tricyclic aromatic carbocyclic ring systems having a total of six to fourteen ring members, or six to twelve ring members, or six to ten ring members, wherein each ring in the system contains 3 to 7 ring members and that has a single point or multipoint of attachment to the rest of the molecule. Wherein the aryl may be optionally substituted with one or more substituents disclosed herein. The term "aryl" may be used interchangeably with the term "aryl ring" or "aromatic ring". Some non-limiting examples of the aryl group include phenyl, naphthyl and anthracenyl.

The term "heteroaryl" refers to monocyclic, bicyclic and tricyclic aromatic carbocyclic ring systems having a total of 5 to 14 ring members, wherein at least one ring in the system is aromatic, and in which at least one ring member is selected from heteroatom, and wherein each ring in the system contains 3 to 7 ring members and that has a single point or multipoint of attachment to the rest of the molecule. Wherein the heteroaryl may be optionally substituted with one or more substituents disclosed herein. Unless otherwise stated, the heteroaryl group may be connected to the rest of the molecule (such as the parent nucleus structure in the general formula) through any reasonable position (which may be C in CH or N in NH). When a —CH$_2$— group is present in the heteroaryl group, the —CH$_2$— group may be optionally replaced by —C(=O)—. The term "heteroaryl" and "heteroaromatic ring" or "heteroaromatic compound" can be used interchangeably herein. In some embodiments, heteroaryl is a heteroaryl group of 5-8 ring atoms comprising 1, 2, 3 or 4 heteroatoms independently selected from O, S and N; in other embodiments, heteroaryl is a heteroaryl group of 5-7 ring atoms comprising 1, 2, 3 or 4 heteroatoms independently selected from O, S and N; in other embodiments, heteroaryl is a heteroaryl group of 5-6 ring atoms comprising 1, 2, 3 or 4 heteroatoms independently selected from O, S and N; in other embodiments, heteroaryl is a heteroaryl group of 5 ring atoms comprising 1, 2, 3 or 4 heteroatoms independently selected from O, S and N; in other embodiments, heteroaryl is a heteroaryl group of 6 ring atoms comprising 1, 2, 3 or 4 heteroatoms independently selected from O, S and N.

Some non-limiting examples of heteroaryl include the following monocyclic groups: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5H-tetrazolyl, 2H-tetrazolyl), triazolyl (e.g., 2-triazolyl, 5-triazolyl, 4H-1,2,4-triazolyl, 1H-1,2,4-triazolyl, 1,2,3-triazolyl), 2-thienyl, 3-thienyl, pyrazolyl (e.g., 2-pyrazolyl and 3-pyrazolyl), isothiazolyl, 1,2,3-oxadiazolyl, 1,2,5-oxadiazolyl, 1,2,4-oxadiazolyl, 1,3,4-oxadiazolyl, 1,2,3-thiodiazolyl, 1,3,4-thiodiazolyl, 1,2,5-thiodiazolyl, pyrazinyl, 1,3,5-triazinyl, and the following bi- or tricyclic groups: indolinyl, 1,2,3,4-tetrahydroisoquinolinyl, benzimidazolyl, benzofuryl, benzothiophenyl, indolyl (e.g., 2-indolyl), purinyl, quinolinyl (e.g., 2-quinolinyl, 3-quinolinyl, 4-quinolinyl), isoquinolinyl (e.g., 1-isoquinolinyl, 3-isoquinolinyl or 4-isoquinolinyl), phenoxothiyl, dibenzimidazolyl, dibenzofuranyl, dibenzothienyl.

The term "heteroatom" refers to one or more of oxygen, sulfur, nitrogen, phosphorus and silicon, including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl, R is a substituent on N).

The term "nitro" refers to —NO$_2$.
The term "mercapto" refers to —SH.
The term "hydroxy" refers to —OH.
The term "amino" refers to —NH$_2$.
The term "cyano" refers to —CN.
The term "carboxylic acid" or "carboxy" refers to —C(=O)OH.
The term "carbonyl", whether used alone or in conjunction with other terms such as "aminocarbonyl" or "acyloxy", means —(C=O)—.
The term "deuterium" refers to D, i.e., $^2$H.

As described herein, "⤴" refers to a double bond, the bond-bonded structure may be "cis isomer", "trans isomer" or "mixture of cis isomer and trans isomer in any proportion"; for example, formula e represents formula e-1, formula e-2 or mixture of both (e-1 and e-2) in any proportion:

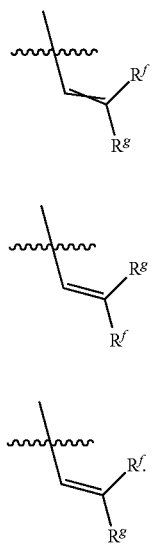

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include, but are not limited to, acetyl, benzoyl, benzyl, p-methoxybenzyl, silyl, and the like. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl) ethyl, 2-(trimethylsilyl) ethoxy-methyl, 2-(p-toluenesulfonyl) ethyl, 2-(p-nitrophenylsulfonyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

The term "leaving group" or "LG" refers to an atom or functional group that is detached from a larger molecule in a chemical reaction, and is a term used in nucleophilic substitution reactions and elimination reactions. In a nucleophilic substitution reaction, a reactant attacked by a nucleophilic reagent is called a substrate, and an atom or atomic group that breaks out with a pair of electrons from a substrate molecule is called a leaving group. Common leaving groups are, for example, but not limited to, halogen atoms, ester groups, sulfonate groups, nitro groups, azide groups, or hydroxy groups.

The phrase "pharmaceutically acceptable" refers to that the substance or composition must be chemically and/or toxicologically compatible with the other ingredients comprising a formulation, and/or the mammal being treated therewith. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" includes any solvents, dispersion media, coating agents, surfactants, antioxidants, preservatives (e.g., antibacterial agents, antifungal agents), isotonic agents, salt, drug stabilizers, binders, excipients, dispersants, lubricants, sweetening agents, flavoring agents, coloring agents, or a combination thereof, all of which are well known to the skilled in the art. (e.g., Remington's Pharmaceutical Sciences, 18th Ed. Mack Printing Company, 1990, pp. 1289-1329, all of which are incorporated herein by reference). Except any conventional carrier is incompatible with the active ingredient, the pharmaceutically acceptable carriers are effectively used in the treatment or pharmaceutical compositions.

The term "pharmaceutical composition" refers to a mixture of one or more of the compounds described herein, or physiologically/pharmaceutically acceptable salts or prodrugs thereof, and other chemical components, such as physiologically/pharmaceutically acceptable carriers, excipients, diluents, binders, fillers, and other additional therapeutic agents, such as anti-diabetic agents, antihyperglycemic agents, antiadipositas agents, antihypertensive agents, antiplatelet agents, antiatherosclerotic agents, lipid-lowering agents, etc. The purpose of the pharmaceutical composition is to facilitate administration of a compound to an organism.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic (C$_{1-24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in Higuchi et al., Pro-drugs as Novel Delivery Systems, Vol. 14, A.C.S. Symposium Series; Roche, et al. ed., Bioreversible Carriers in Drug Design, American Pharmaceutical Association and Pergamon Press, 1987; Rautio et al., Prodrugs: Design and Clinical Applications, Nature Reviews Drug Discovery, 2008, 7, 255-270, and Hecker et al., Prodrugs of Phosphates and Phosphonates, J. Med. Chem., 2008, 51, 2328-2345, all of which are incorporated herein by reference in their entireties.

The term "metabolite" refers to a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

The term "pharmaceutically acceptable salt" refers to organic or inorganic salts of a compound disclosed herein. Pharmaceutically acceptable salts are well known in the art. For example, the pharmaceutically acceptable salts are described in detail in Berge et al., J. Pharmacol Sci, 1977, 66: 1-19, which is incorporated herein by reference in its entirety.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine. The term "hydrate" refers to the complex where the solvent molecule is water.

The term "N-oxide" refers to one or more than one nitrogen atoms oxidised to form an N-oxide, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g. a peroxycarboxylic acid) (See, Advanced Organic Chemistry, by Jerry March, 4th Edition, Wiley Interscience, pages). More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. If possible, the substituent on the atom having an unsaturated double bond may exist in the form of cis-(Z)— or trans-(E)-.

Therefore, as the invention described, the compound disclosed herein may exist in the form of any possible isomer, rotamer, atropisomer, tautomer, or a mixture thereof, e.g., substantially pure geometric (cis- or trans-) isomer, diastereoisomer, optical isomer (enantiomer), racemate or a mixture thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); Principles of Asymmetric Synthesis (2nd Ed. Robert E. Gawley, Jeffrey Aubé, Elsevier, Oxford, UK, 2012); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, IN 1972);

The present invention also includes isotopically-labeled compounds of the present invention, which are the same as those described in the present invention except for the fact that one or more atoms are replaced by atoms whose atomic mass or mass number is different from the atomic mass or mass number commonly found in nature. Examples of isotopes that can be incorporated into compounds of the invention include isotopes of hydrogen, carbon, nitrogen, oxygen, phosphorous, sulfur, fluorine, and chlorine, such as $^{2}H$, $^{3}H$, $^{13}C$, $^{14}C$, $^{15}N$, $^{16}O$, $^{17}O$, $^{31}P$, $^{32}P$, $^{36}S$, $^{18}F$ and $^{37}Cl$, respectively.

The compounds disclosed herein containing isotopes described above or other atom isotopes and pharmaceutical salts thereof are included within the scope of the present invention. Certain isotopically-labeled compounds of the present invention, for example those into which radioactive isotopes such as $^{3}H$ or $^{14}C$ are incorporated, are useful in drug and/or substrate tissue distribution assays. Because of easy preparation and detection, isotopes such as tritiated, i.e., $^{3}H$, and carbon-14, i.e., $^{14}C$ are preferred. Further, substitution with heavier isotopes, particularly deuterium (i.e., $^{2}H$ or D) may afford certain therapeutic advantages resulting from greater metabolic stability, for example increased in vivo half-life or reduced dosage requirements. Therefore, the heavier isotopes may be preferred in somewhere.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, different optically active compounds are called stereoisomers and are identical except that they are mirror images of one another. A specific stereoisomer is referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

The compounds disclosed herein may contain asymmetric or chiral centers, and therefore exist in different stereoisomeric forms. It is intended that all stereoisomeric forms of the compounds disclosed herein, including, but not limited to, diastereomers, enantiomers, atropisomers, geometric (or conformational) isomers, as well as mixtures thereof such as racemic mixtures, form part of the present invention.

Unless otherwise specified, the formula described herein also contains all the isomers thereof (such as, enantiomers, diastereomers, atropisomers and geometric (conformational) isomers; such as all (R)- and (S)-isomers, (Z) and (E) isomers around the double bond, (Z) and (E) conformational isomers. Therefore, single stereochemical isomers as well as enantiomeric, diastereomeric, or geometric mixtures (or conformers) of the present compounds are within the scope disclosed herein.

The term "tautomer" or "tautomeric form" refers to structural isomers of different energies which are interconvertible via a low energy barrier. Where tautomerization is possible (e.g. in solution), a chemical equilibrium of tautomers can be reached. For example, protontautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. The specific example of phenol-keto tautomerisms is pyridin-4-ol and pyridin-4(1H)-one tautomerism. Unless otherwise stated, all tautomeric forms of the compounds disclosed herein are within the scope of the invention.

The term "geometric isomer" is also known as "cis-trans isomer", which is caused by the double bond (including the double bond of olefin, C=N double bond and N=N double bond) or the single bond of ring carbon atom that cannot rotate freely.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

The term "subject" can be used interchangeably with "patient" in the invention. The term "subject" and "patient" refer to animals (e.g., birds such as chicken, quail or turkey, or mammals), specially mammals including non-primates (e.g., cattle, pigs, horses, sheep, rabbits, guinea pigs, rats, dogs, cats and mice) and primates (e.g., monkeys, chimpanzees and humans), more specially humans. In one embodiment, the subject is a non-human animal, such as a domestic animal (e.g., horse, cow, pig, or sheep) or a pet (e.g., dog, cat, guinea pig or rabbit). In some embodiments, "patient" refers to a human.

The term "syndrome X", also known as conditions, diseases of metabolic syndrome, the disorders are detailed in Johannsson et al., J. Clin. Endocrinol. Metab., 1997; 82, 727-734, which is incorporated herein by reference.

"Inflammation disorder/disease" as used herein can refer to any disease, disorder, or syndrome in which an excessive or unregulated inflammatory response leads to excessive inflammatory symptoms, host tissue damage, or loss of tissue function. "Inflammation disease" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with the compounds disclosed herein encompass disorders associated with reactions of the specific defense system as well as with reactions of the nonspecific defense system.

"Allergy" as used herein refers to any symptom, tissue damage or loss of tissue function causing allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

Additionally, unless otherwise stated, structures depicted herein are also meant to include compounds that differ only in the presence of one or more isotopically enriched atoms.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

Description of Compounds of the Invention

The present invention provides an isoquinolinone compound having a good inhibition of SSAO/VAP-1 activity, which is used in the manufacture of a medicament for treating inflammation and/or a disease related to inflammation, diabetes and/or a disease related to diabetes, a mental disorder, an ischemic disease, a vascular disease, fibrosis or tissue transplant rejection, in particular for treating non-alcoholic steatohepatitis in a patient. The present invention also provides methods of preparing these compounds, pharmaceutical compositions comprising these compounds, and methods of using these compounds and compositions to prepare medicaments for the above-mentioned diseases in mammals, especially humans. Compared with the existing similar compounds, the compound of the present invention not only has good pharmacological activity, but also has excellent in vivo metabolic kinetic properties and in vivo pharmacodynamic properties. At the same time, the compound of the present invention has high selectivity to SSAO/VAP-1. The preparation method of the compound of the present invention is simple and easy, and the technological method is stable, which is suitable for industrial production. Therefore, the compound provided by the present invention has better druggability compared with the existing similar compounds.

Specifically:

In one aspect, provided herein is a compound having Formula (I) or a stereoisomer, a geometric isomer, a tautomer, an N-oxide, a solvate, a metabolite, a pharmaceutically acceptable salt or a prodrug thereof,

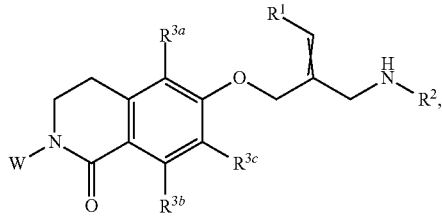

(I)

wherein, W, $R^1$, $R^2$, $R^{3a}$, $R^{3b}$ and $R^{3c}$ have the definition as described in the present invention.

In some embodiments, $R^1$ is F, Cl, Br or I.

In some embodiments, $R^2$ is H, deuterium, $C_{1-6}$ alkyl, $C_{1-6}$ haloalkyl, $C_{3-6}$ cycloalkyl, 3-6 membered heterocyclyl, $C_{6-10}$ aryl, 5-6 membered heteroaryl or

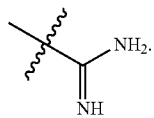

In some embodiments, each of $R^{3a}$, $R^{3b}$ and $R^{3c}$ is independently H, deuterium, F, Cl, Br, I, CN, $NO_2$, —COOH, OH, $NH_2$, —C(=O)—$C_{1-6}$ alkyl, —C(=O)—$C_{1-6}$ alkoxy, $C_{1-6}$ alkyl, $C_{1-6}$ alkoxy, $C_{1-6}$ haloalkyl, $C_{1-6}$ haloalkoxy, hydroxy $C_{1-6}$ alkyl, amino $C_{1-6}$ alkyl, cyano $C_{1-6}$ alkyl, carboxy $C_{1-6}$ alkyl, $C_{3-6}$ cycloalkyl, 5-6 membered heterocyclyl, $C_{6-10}$ aryl or 5-6 membered heteroaryl.

In some embodiments, W is -L-$R^4$ or —$(CR^aR^b)_t$P(=O)($R^5$)($R^6$); wherein the L, $R^4$, $R^a$, $R^b$, $R^5$, $R^6$ and t are as defined herein.

In some embodiments, L is —$(CR^aR^b)_p$—C(=O)—$NR^c$—, —$(CR^aR^b)_q$—S—, —$(CR^aR^b)_q$—S(=O)—, —$(CR^aR^b)_s$—S(=O)$_2$—, —$(CR^aR^b)_q$—S(=O)$_2$—$NR^c$— or —$(CR^aR^b)_q$—S(=O)—$NR^c$—; wherein each of $R^a$, $R^b$, p, q and s is as defined herein.

In some embodiments, each of q, p, s, and t is independently 0, 1, 2, 3, 4, or 5.

In some embodiments, each of $R^a$, $R^b$ and $R^c$ is independently H, deuterium, F, Cl, Br, I, CN, $NO_2$, —COOH, OH, $NH_2$, $C_{1-6}$ alkyl, $C_{1-6}$ alkoxy, $C_{1-6}$ haloalkyl, $C_{1-6}$ haloalkoxy, hydroxy $C_{1-6}$ alkyl, amino $C_{1-6}$ alkyl, cyano $C_{1-6}$ alkyl, carboxyl $C_{1-6}$ alkyl, $C_{3-6}$ cycloalkyl, 3-6 membered heterocyclyl, $C_{6-10}$ aryl or 5-6 membered heteroaryl.

In some embodiments, $R^4$ is H, deuterium, $C_{1-8}$ alkyl, $C_{2-6}$ alkenyl, $C_{2-6}$ alkynyl, $C_{1-6}$ haloalkyl, $C_{3-6}$ cycloalkyl, 3-6 membered heterocyclyl, $C_{6-10}$ aryl or 5-6 membered heteroaryl, wherein each of the $C_{1-8}$ alkyl, $C_{2-6}$ alkenyl, $C_{2-6}$ alkynyl, $C_{1-6}$ haloalkyl, $C_{3-6}$ cycloalkyl, 3-6 membered heterocyclyl, $C_{6-10}$ aryl and 5-6 membered heteroaryl is independently unsubstituted or substituted with 1, 2, 3 or 4 BY;

or $R^c$ and $R^4$ together with the nitrogen atom to which they are attached, form 3-6 membered heterocyclyl or 5-6 membered heteroaryl, wherein each of 3-6 membered heterocyclyl and 5-6 membered heteroaryl is independently unsubstituted or substituted with 1, 2, 3 or 4 $R^y$; wherein each $R^y$ is as defined herein.

In some other embodiments, each of $R^5$ and $R^6$ is independently OH, $NH_2$, $C_{1-6}$ alkyl, $C_{1-6}$ alkoxy, $C_{1-6}$ alkylamino, $C_{3-6}$ cycloalkyl, $C_{3-6}$ cycloalkyloxy, $C_{3-6}$ cycloalkylamino, 5-6 membered heterocyclyl, 3-6 membered heterocyclyloxy, 3-6 membered heterocyclylamino, $C_{6-10}$ aryl, $C_{6-10}$ aryloxy, $C_{6-10}$ arylamino, 3-6 membered heteroaryl, 5-6 membered heteroaryloxy or 5-6 membered heteroarylamino, wherein each of the $C_{1-6}$ alkyl, $C_{1-6}$ alkoxy, $C_{1-6}$ alkylamino, $C_{3-6}$ cycloalkyl, $C_{3-6}$ cycloalkyloxy, $C_{3-6}$ cycloalkylamino, 5-6 membered heterocyclyl, 3-6 membered heterocyclyloxy, 3-6 membered heterocyclylamino, $C_{6-10}$ aryl, $C_{6-10}$ aryloxy, $C_{6-10}$ arylamino, 3-6 membered heteroaryl, 5-6 membered heteroaryloxy or 5-6 membered heteroarylamino is independently unsubstituted or substituted with 1, 2, 3 or 4 $R^y$;

or $R^5$ and $R^6$ together with the phosphorus atom to which they are attached, form 3-6 membered heterocyclyl or 5-6 membered heteroaryl, wherein each of 3-6 membered heterocyclyl and 5-6 membered heteroaryl is independently unsubstituted or substituted with 1, 2, 3 or 4 $R^y$; wherein each $R^y$ is as defined herein.

In some embodiments, each $R^y$ is independently deuterium, F, Cl, Br, I, CN, $NO_2$, —COOH, OH, $NH_2$, —SH, —C(=O)—$C_{1-6}$ alkyl, —C(=O)—$C_{1-6}$ alkoxy, —S(=O)$_2$—$C_{1-6}$ alkyl, —S(=O)$_2$—$C_{1-6}$ alkylamino, $C_{1-6}$ alkyl, $C_{1-6}$ alkoxy, $C_{1-6}$ haloalkyl, $C_{1-6}$ haloalkoxy, hydroxy $C_{1-6}$ alkyl, amino $C_{1-6}$ alkyl, cyano $C_{1-6}$ alkyl, carboxy $C_{1-6}$ alkyl, $C_{3-6}$ cycloalkyl, 5-6 membered heterocyclyl, $C_{6-10}$ aryl or 5-6 membered heteroaryl.

In some other embodiments, $R^4$ is H, deuterium, $C_{1-6}$ alkyl, $C_{2-4}$ alkenyl, $C_{2-4}$ alkynyl, $C_{1-4}$ haloalkyl, $C_{3-6}$ cycloalkyl, 5-6 membered heterocyclyl, $C_{6-10}$ aryl or 5-6 membered heteroaryl, wherein each of the $C_{1-6}$ alkyl, $C_{2-4}$ alkenyl, $C_{2-4}$ alkynyl, $C_{1-4}$ haloalkyl, $C_{3-6}$ cycloalkyl, 5-6 membered heterocyclyl, $C_{6-10}$ aryl and 5-6 membered heteroaryl is independently unsubstituted or substituted with 1, 2, 3 or 4 BY;

or $R^c$ and $R^4$ together with the nitrogen atom to which they are attached, form 5-6 membered heterocyclyl or 5-6 membered heteroaryl, wherein each of 5-6 membered heterocyclyl and 5-6 membered heteroaryl is independently unsubstituted or substituted with 1, 2, 3 or 4 $R^y$; wherein each $R^y$ is as defined herein.

In still other embodiments, $R^4$ is H, deuterium, methyl, ethyl, n-propyl, isopropyl, n-butyl, isobutyl, tert-butyl, n-pentyl, n-hexyl, vinyl, allyl, propenyl, ethynyl, —$CHF_2$, —$CF_3$, —$CH_2CHF_2$, —$CH_2CF_3$, cyclopropyl, cyclobutyl, cyclopentyl, cyclohexyl, pyrrolidinyl, pyrazolidinyl, tetrahydrofuranyl, tetrahydrothienyl, tetrahydropyranyl, piperidinyl, morpholinyl, thiomorpholinyl, piperazinyl, phenyl, naphthyl, furanyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the methyl, ethyl, n-propyl, isopropyl, n-butyl, isobutyl, tert-butyl, n-pentyl, n-hexyl, vinyl, allyl, propenyl, ethynyl, —$CHF_2$, —$CF_3$, —$CH_2CHF_2$, —$CH_2CF_3$, cyclopropyl, cyclobutyl, cyclopentyl, cyclohexyl, pyrrolidinyl, pyrazolidinyl, tetrahydrofuranyl, tetrahydrothienyl, tetrahydropyranyl, piperidinyl, morpholinyl, thiomorpholinyl, piperazinyl, phenyl, naphthyl, furanyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3 or 4 $R^y$;

or $R^c$ and $R^4$ together with the nitrogen atom to which they are attached, form pyrrolidinyl, pyrazolidinyl, imidazolidinyl, piperidinyl, morpholinyl, piperazinyl, pyrrolyl, pyridyl, pyrazolyl, imidazolyl, triazolyl, tetrazolyl, oxazolyl, isoxazolyl, oxadiazolyl, 1,3,5-triazinyl, pyrazinyl, thiazolyl or pyrimidinyl, wherein each of the pyrrolidinyl, pyrazolidinyl, imidazolidinyl, piperidinyl, morpholinyl, piperazinyl, pyrrolyl, pyridyl, pyrazolyl, imidazolyl, triazolyl, tetrazolyl, oxazolyl, isoxazolyl, oxadiazolyl, 1,3,5-triazinyl, pyrazinyl, thiazolyl and pyrimidinyl is independently unsubstituted or substituted with 1, 2, 3 or 4 $R^y$; wherein each $R^y$ is as defined herein.

In other embodiments, each of $R^5$ and $R^6$ is independently OH, $NH_2$, $C_{1-4}$ alkyl, $C_{1-4}$ alkoxy, $C_{1-4}$ alkylamino, $C_{3-6}$ cycloalkyl, $C_{3-6}$ cycloalkyloxy, $C_{3-6}$ cycloalkylamino, 5-6 membered heterocyclyl, 5-6 membered heterocyclyloxy, 5-6 membered heterocyclylamino, $C_{6-10}$ aryl, $C_{6-10}$ aryloxy, $C_{6-10}$ arylamino, 5-6 membered heteroaryl, 5-6 membered heteroaryloxy or 5-6 membered heteroarylamino, wherein each of the $C_{1-4}$ alkyl, $C_{1-4}$ alkoxy, $C_{1-4}$ alkylamino, $C_{3-6}$ cycloalkyl, $C_{3-6}$ cycloalkyloxy, $C_{3-6}$ cycloalkylamino, 5-6 membered heterocyclyl, 5-6 membered heterocyclyloxy, 5-6 membered heterocyclylamino, $C_{6-10}$ aryl, $C_{6-10}$ aryloxy, $C_{6-10}$ arylamino, 5-6 membered heteroaryl, 5-6 membered heteroaryloxy and 5-6 membered heteroarylamino is independently unsubstituted or substituted with 1, 2, 3 or 4 BY;
or $R^5$ and $R^6$ together with the phosphorus atom to which they are attached, form 5-6 membered heterocyclyl or 5-6 membered heteroaryl, wherein each of 5-6 membered heterocyclyl and 5-6 membered heteroaryl is independently unsubstituted or substituted with 1, 2, 3 or 4 $R^y$; wherein each $R^y$ is as defined herein.

In still other embodiments, each of $R^5$ and $R^6$ is independently OH, $NH_2$, methyl, ethyl, n-propyl, isopropyl, n-butyl, isobutyl, tert-butyl, methoxy, ethoxy, n-propyloxy, isopropyloxy, N-methylamino, N,N-dimethylamino, N-ethylamino, N,N-diethylamino, N-n-propylamino, N-isopropylamino, cyclopropyl, cyclobutyl, cyclopentyl, cyclohexyl, cyclopropyloxy, cyclobutyloxy, cyclopentyloxy, cyclohexyloxy, N-cyclopropylamino, N,N-dicyclopropylamino, N-cyclobutylamino, N-cyclopentylamino, N-cyclohexylamino, 5-6 membered heterocyclyl, 5-6 membered heterocyclyloxy, 5-6 membered heterocyclylamino, phenyl, phenyloxy, N-phenylamino, 5-6 membered heteroaryl, 5-6 membered heteroaryloxy or 5-6 membered heteroarylamino, wherein each of the methyl, ethyl, n-propyl, isopropyl, n-butyl, isobutyl, tert-butyl, methoxy, ethoxy, n-propyloxy, isopropyloxy, N-methylamino, N,N-dimethylamino, N-ethylamino, N,N-diethylamino, N-n-propylamino, N-isopropylamino, cyclopropyl, cyclobutyl, cyclopentyl, cyclohexyl, cyclopropyloxy, cyclobutyloxy, cyclopentyloxy, cyclohexyloxy, N-cyclopropylamino, N,N-dicyclopropylamino, N-cyclobutylamino, N-cyclopentylamino, N-cyclohexylamino, 5-6 membered heterocyclyl, 5-6 membered heterocyclyloxy, 5-6 membered heterocyclylamino, phenyl, phenyloxy, N-phenylamino, 5-6 membered heteroaryl, 5-6 membered heteroaryloxy and 5-6 membered heteroarylamino is independently unsubstituted or substituted with 1, 2, 3 or 4 $R^y$;
or $R^5$ and $R^6$ together with the phosphorus atom to which they are attached, form 5-6 membered heterocyclyl or 5-6 membered heteroaryl, wherein each of 5-6 membered heterocyclyl and 5-6 membered heteroaryl is independently unsubstituted or substituted with 1, 2, 3 or 4 $R^y$; wherein each $R^y$ is as defined herein.

In some other embodiments, each $R^y$ is independently deuterium, F, Cl, Br, I, CN, $NO_2$, —COOH, OH, $NH_2$, —SH, —C(=O)—$C_{1-4}$ alkyl, —C(=O)—$C_{1-4}$ alkoxy, —S(=O)$_2$—$C_{1-4}$ alkyl, —S(=O)$_2$—$C_{1-4}$ alkylamino, $C_{1-4}$ alkyl, $C_{1-4}$ alkoxy, $C_{1-4}$ haloalkyl, $C_{1-4}$ haloalkoxy, hydroxy $C_{1-4}$ alkyl, amino $C_{1-4}$ alkyl, cyano $C_{1-4}$ alkyl, carboxy $C_{1-4}$ alkyl, $C_{3-6}$ cycloalkyl, 5-6 membered heterocyclyl, $C_{6-10}$ aryl or 5-6 membered heteroaryl.

In still other embodiments, each $R^y$ is independently deuterium, F, Cl, Br, I, CN, $NO_2$, —COOH, OH, $NH_2$, —SH, —C(=O)-methyl, —C(=O)-ethyl, —C(=O)-methoxy, —C(=O)-ethoxy, —S(=O)$_2$-methyl, —S(=O)$_2$-ethyl, —S(=O)$_2$-n-propyl, —S(=O)$_2$-isopropyl, —S(=O)$_2$-n-butyl, —S(=O)$_2$-tert-butyl, —S(=O)$_2$-methylamino, —S(=O)$_2$-ethylamino, —S(=O)$_2$-n-propylamino, —S(=O)$_2$-isopropylamino, —S(=O)$_2$-tert-butylamino, methyl, ethyl, n-propyl, isopropyl, n-butyl, isobutyl, tert-butyl, methoxy, ethoxy, n-propyloxy, isopropyloxy, —$CHF_2$, —$CF_3$, —$CH_2CHF_2$, —$CH_2CF_3$, trifluoromethoxy, hydroxymethyl, hydroxyethyl, aminomethyl, aminoethyl, cyanomethyl, cyanoethyl, carboxymethyl, cyclopropyl, cyclobutyl, cyclopentyl, cyclohexyl, 5-6 membered heterocyclyl, phenyl or 5-6 membered heteroaryl.

In some other embodiments, each of $R^a$, $R^b$ and $R^c$ is independently H, deuterium, F, Cl, Br, I, CN, $NO_2$, —COOH, OH, $NH_2$, $C_{1-4}$ alkyl, $C_{1-4}$ alkoxy, $C_{1-4}$ haloalkyl, $C_{1-4}$ haloalkoxy, hydroxy $C_{1-4}$ alkyl, amino $C_{1-4}$ alkyl, cyano $C_{1-4}$ alkyl, carboxyl $C_{1-4}$ alkyl, $C_{3-6}$ cycloalkyl, 5-6 membered heterocyclyl, $C_{6-10}$ aryl or 5-6 membered heteroaryl.

In still other embodiments, each of $R^a$, $R^b$ and $R^c$ is independently H, deuterium, F, Cl, Br, I, CN, $NO_2$, —COOH, OH, $NH_2$, methyl, ethyl, n-propyl, isopropyl, methoxy, ethoxy, —$CHF_2$, —$CF_3$, —$CH_2CHF_2$, —$CH_2CF_3$, trifluoromethoxy, hydroxymethyl, hydroxyethyl, aminomethyl, aminoethyl, cyanomethyl, carboxymethyl, cyclopropyl, cyclobutyl, cyclopentyl, cyclohexyl, 5-6 membered heterocyclyl, phenyl or 5-6 membered heteroaryl.

In some other embodiments, $R^2$ is H, deuterium, $C_{1-4}$ alkyl, $C_{1-4}$ haloalkyl, $C_{3-6}$ cycloalkyl, 5-6 membered heterocyclyl, $C_{6-10}$ aryl, 5-6 membered heteroaryl or

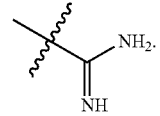

In still other embodiments, $R^2$ is H, deuterium, methyl, ethyl, n-propyl, isopropyl, n-butyl, isobutyl, tert-butyl, —$CHF_2$, —$CF_3$, —$CH_2CHF_2$, —$CH_2CF_3$, cyclopropyl, cyclobutyl, cyclopentyl, cyclohexyl, 5-6 membered heterocyclyl, phenyl, 5-6 membered heteroaryl or

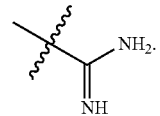

In some other embodiments, each of $R^{3a}$, $R^{3b}$, and $R^{3c}$ is independently H, deuterium, F, Cl, Br, I, CN, $NO_2$, —COOH, OH, $NH_2$, —C(=O)—$C_{1-4}$ alkyl, —C(=O)—$C_{1-4}$ alkoxy, $C_{1-4}$ alkyl, $C_{1-4}$ alkoxy, $C_{1-4}$ haloalkyl, $C_{1-4}$ haloalkoxy, hydroxy $C_{1-4}$ alkyl, amino $C_{1-4}$ alkyl, cyano $C_{1-4}$ alkyl, carboxyl $C_{1-4}$ alkyl, $C_{3-6}$ cycloalkyl, 5-6 membered heterocyclyl, $C_{6-10}$ aryl or 5-6 membered heteroaryl.

In still other embodiments, each of $R^{3a}$, $R^{3b}$, and $R^{3c}$ is independently H, deuterium, F, Cl, Br, I, CN, $NO_2$, —COOH, OH, $NH_2$, —C(=O)-methyl, —C(=O)-ethyl, —C(=O)-methoxy, —C(=O)-ethoxy, methyl, ethyl, n-propyl, isopropyl, n-butyl, isobutyl, tert-butyl, methoxy, ethoxy, —CHF₂, —CF₃, —CH₂CHF₂, —CH₂CF₃, trifluoromethoxy, hydroxymethyl, hydroxyethyl, aminomethyl, aminoethyl, cyanomethyl, carboxymethyl, cyclopropyl, cyclobutyl, cyclopentyl, cyclohexyl, 5-6 membered heterocyclyl, phenyl or 5-6 membered heteroaryl.

In another aspect, the present invention relates to one of the following structures, or a stereoisomer, a geometric isomer, a tautomer, an N-oxide, a solvate, a metabolite, a pharmaceutically acceptable salt or a prodrug thereof,

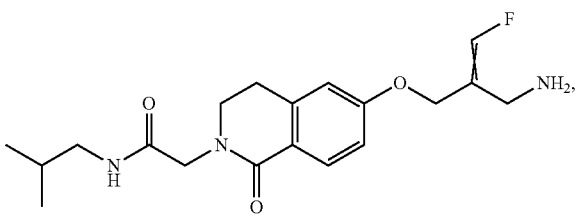
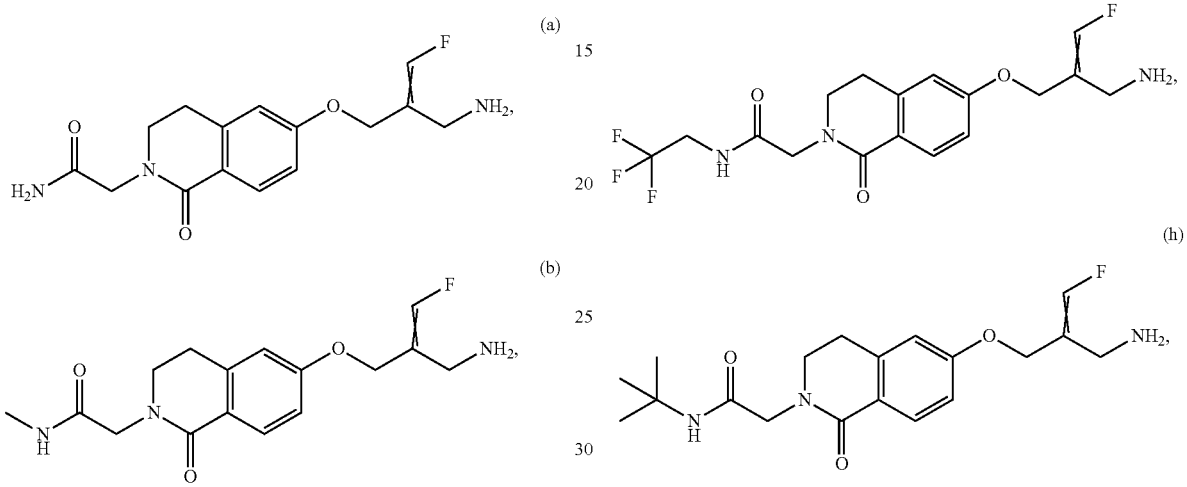
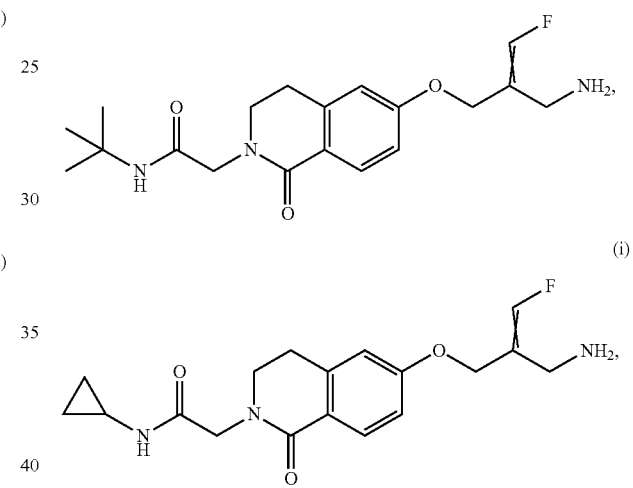
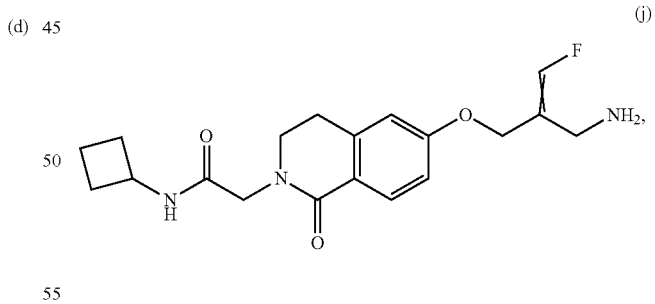
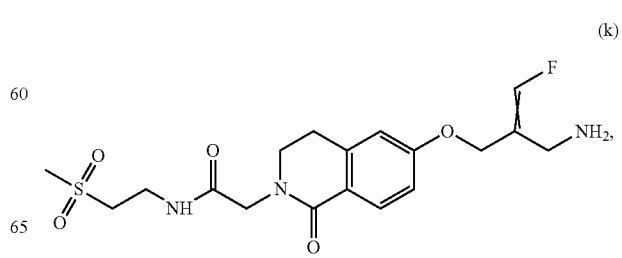

In another aspect, the present invention relates to one of the following structures, or a stereoisomer, a geometric isomer, a tautomer, an N-oxide, a solvate, a metabolite, a pharmaceutically acceptable salt or a prodrug thereof, -continued
(2)
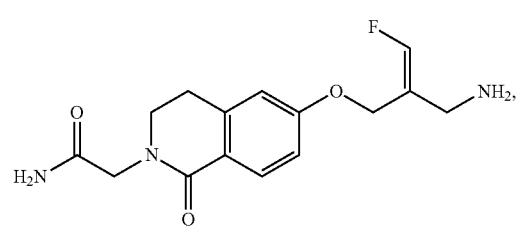
(3)
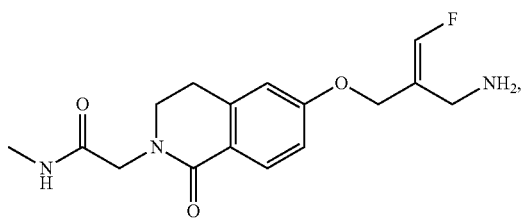
(4)
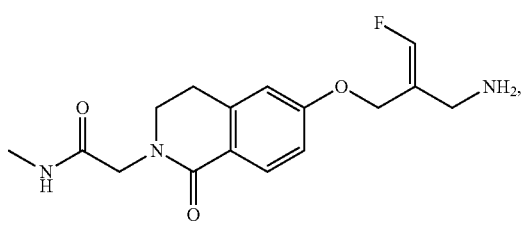
(5)
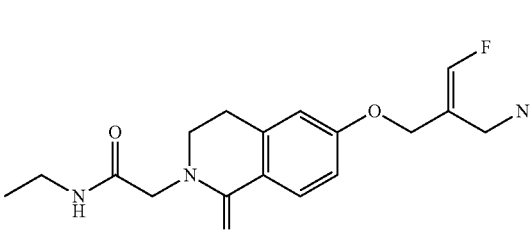
(6)
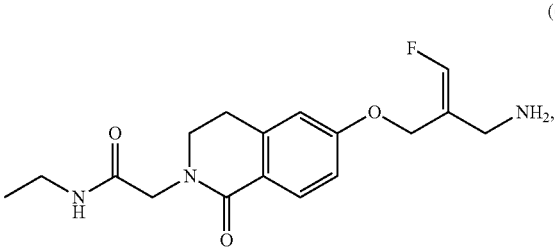
(7)
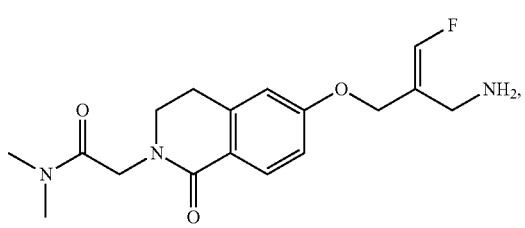
-continued
(8)
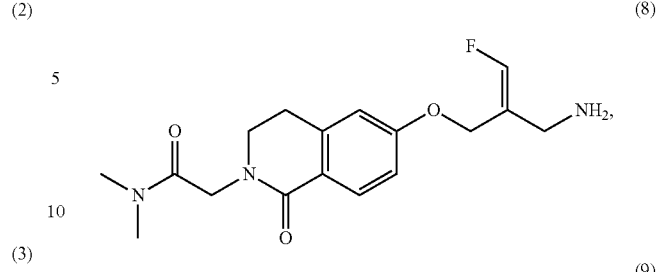
(9)
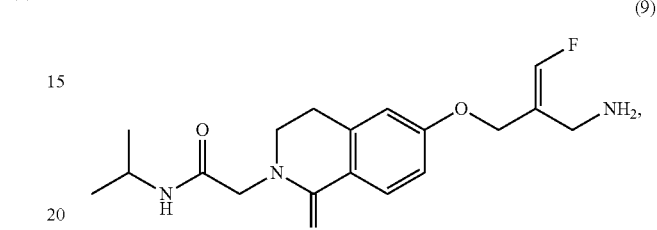
(10)
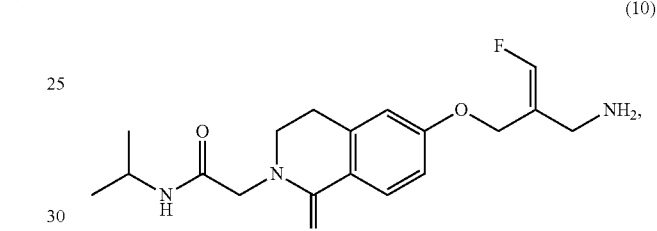
(11)
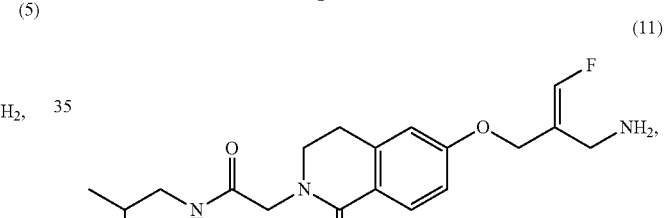
(12)
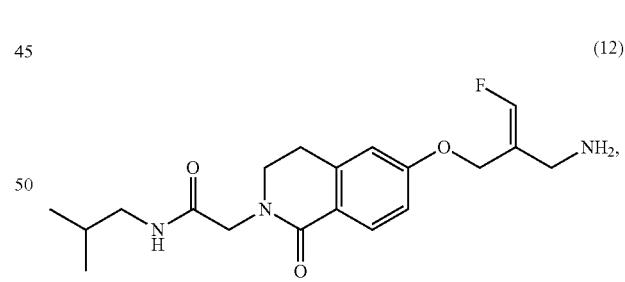
(13)
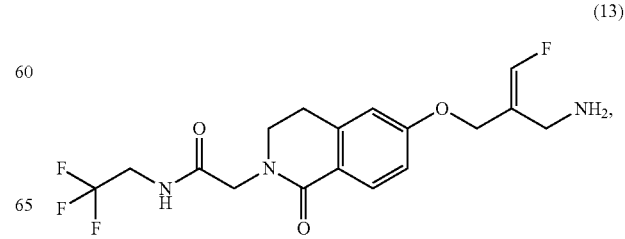

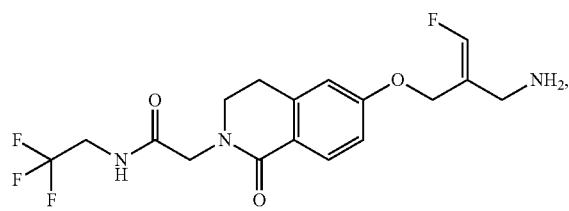
(14)
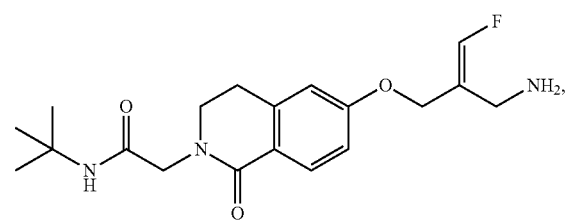
(15)
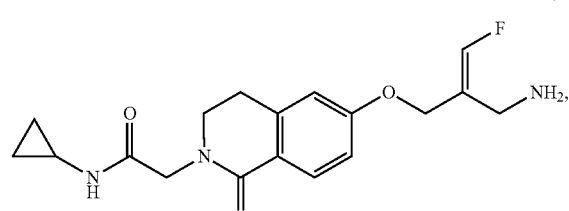
(16)
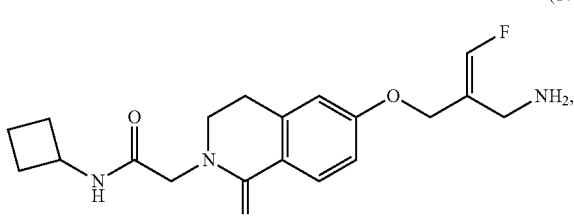
(17)
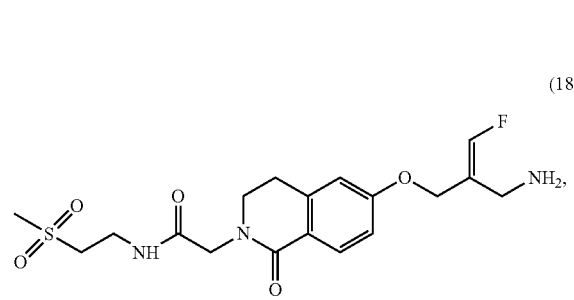
(18)
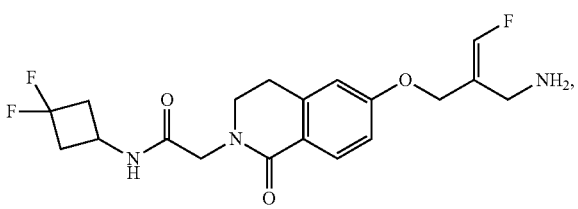
(19)
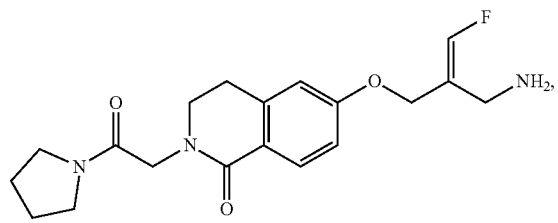
(20)
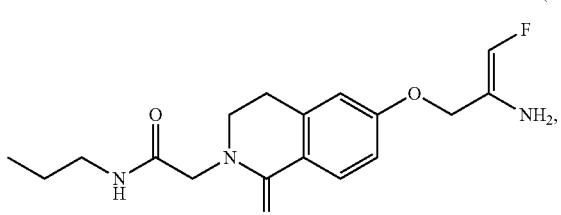
(21)
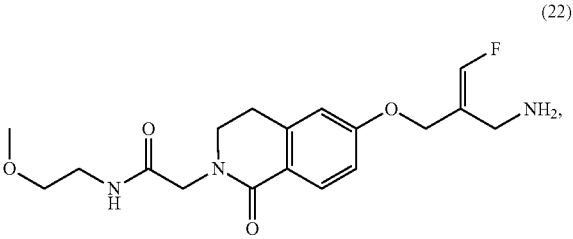
(22)
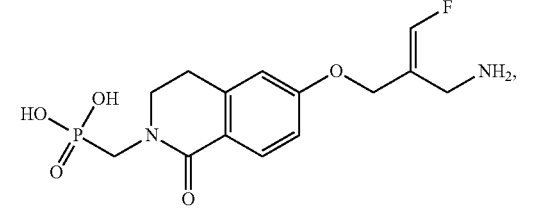
(23)
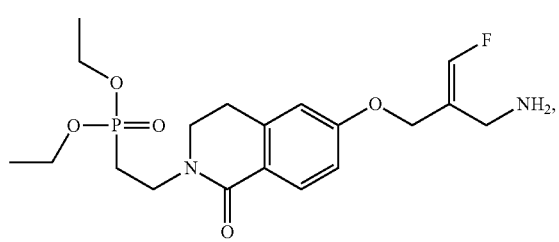
(24)
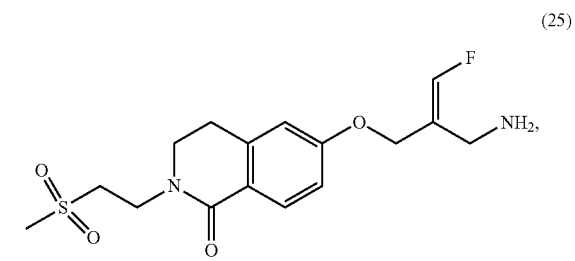
(25)

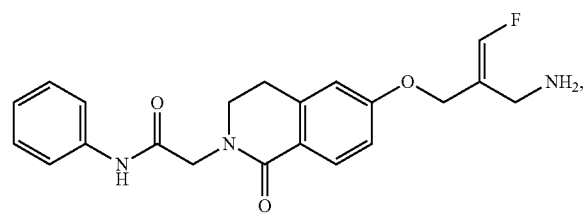
(26)
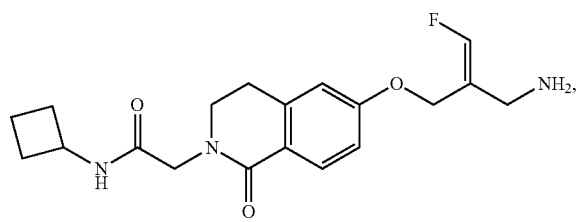
(32)
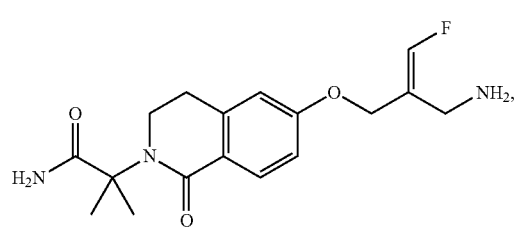
(27)
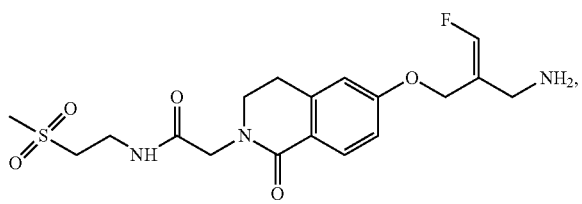
(33)
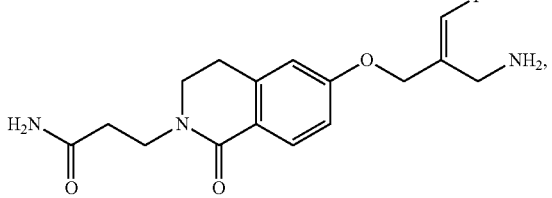
(28)
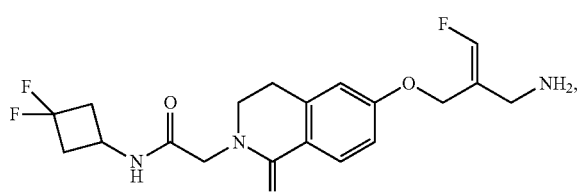
(34)
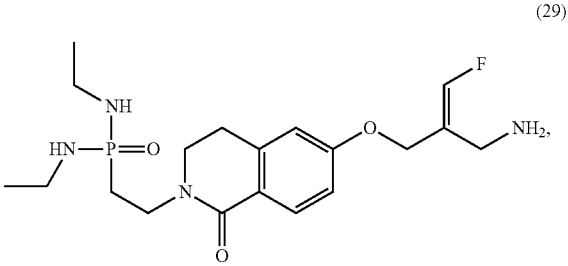 [SMILES: CCNP(=O)(CCN1CCc2cc(OCC(=CF)CN)ccc2C1=O)NCC]
(29)
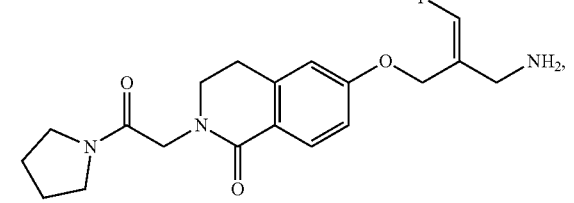
(35)
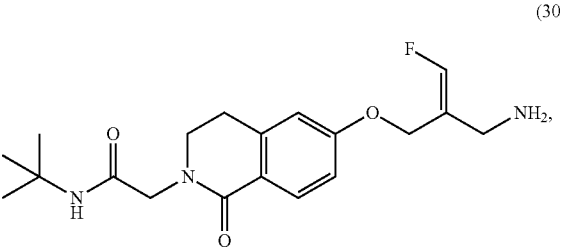
(30)
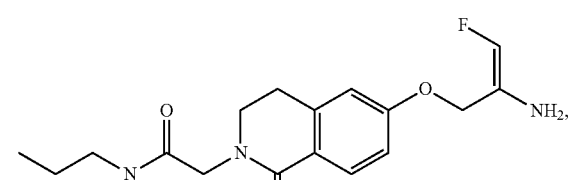
(36)
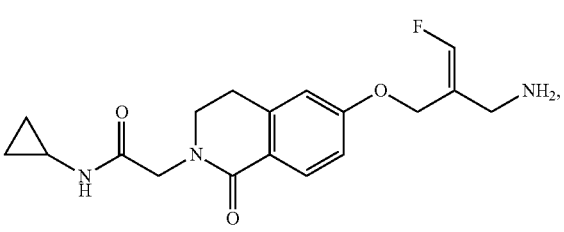
(31)
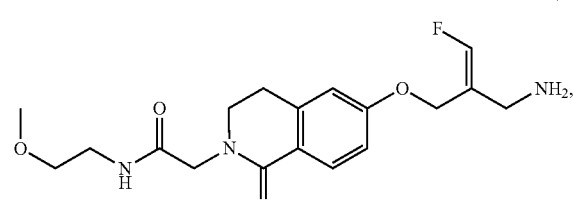
(37)
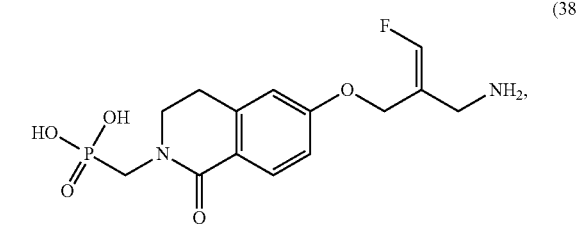
(38)

-continued

(39)
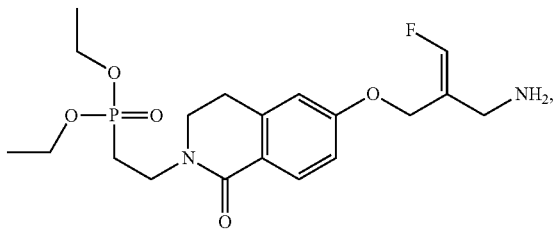

(40)
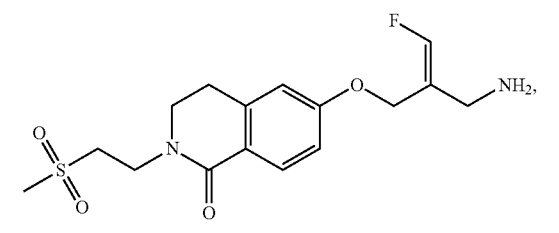

(41)
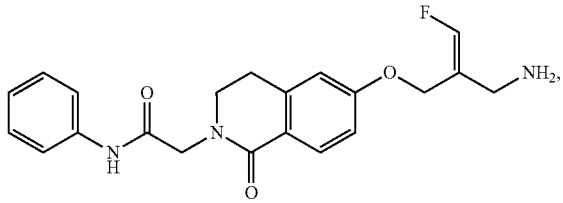

(42)
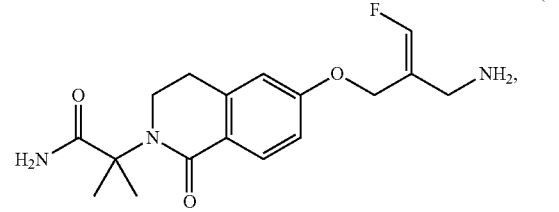

(43)
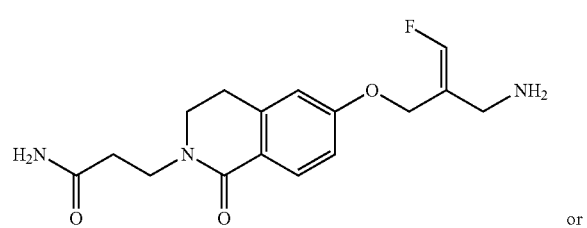

or

(44)
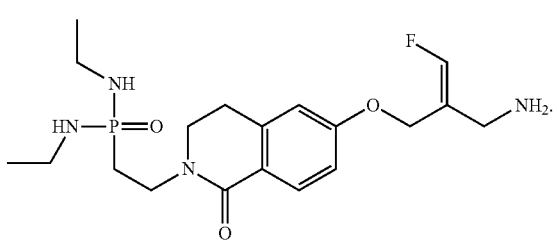

In some embodiments, the pharmaceutically acceptable salt is hydrochloride, hydrobromide, phosphate, oxalate, maleate, tartrate, citrate, malate or methanesulfonate.

In other aspect, provided herein is a pharmaceutical composition comprising the compound disclosed herein.

In some embodiments, the pharmaceutical composition disclosed herein further comprises any one of pharmaceutically acceptable carriers, excipients, adjuvants, vehicles or combinations thereof.

In some embodiments, the pharmaceutical compositions disclosed herein further comprise one or more therapeutic agents.

In other embodiments, the therapeutic agent disclosed herein is a SSAO/VAP-1 inhibitor.

In other embodiments, the pharmaceutical composition of the invention is in the form of liquid, solid, semi-solid, gel or spray.

In other embodiments of the pharmaceutical composition, the therapeutic agent involved is Vapaliximab, PRX-167700, BTT-1023, ASP-8232, PXS-4728A or RTU-1096.

In other aspect, provided herein is use of the compound or the pharmaceutical composition disclosed herein in the manufacture of a medicament for inhibiting SSAO/VAP-1.

In other aspect, provided herein is use of the compound or the pharmaceutical composition disclosed herein in the manufacture of a medicament for preventing, treating or ameliorating a disease related to SSAO/VAP-1 protein or regulated by SSAO/VAP-1 in a subject.

In some embodiments, the disease disclosed herein related to SSAO/VAP-1 protein or regulated by SSAO/VAP-1 is inflammation and/or a disease related to inflammation, diabetes and/or a disease related to diabetes, a mental disorder, an ischemic disease, a vascular disease, fibrosis or tissue transplant rejection.

In other embodiments, the inflammation and/or a disease related to inflammation disclosed herein is arthritis, systemic inflammatory response syndrome, pyemia, synovitis, a Crohn's disease, ulcerative colitis, an inflammatory bowel disease, hepatopathy, a respiratory disease, an eye disease, a skin disease or neuritis.

In still other embodiments, the diabetes and/or a disease related to diabetes disclosed herein is type I diabetes, type II diabetes, X syndrome, diabetic retinopathy, diabetic nephropathy, diabetic neuropathy or diabetic macular edema.

In still other embodiments, the mental disorder disclosed herein is severe depression, bipolar depression or attention deficit hyperactivity disorder.

In still other embodiments, the ischemic disease disclosed herein is apoplexia and/or a complication thereof, myocardial infarction and/or a complication thereof or damage of inflammatory cells to tissues after apoplexia.

In still other embodiments, the fibrosis disclosed herein is hepatic fibrosis, cystic fibrosis, renal fibrosis, idiopathic pulmonary fibrosis or radiation-induced fibrosis.

In still other embodiments, the vascular disease disclosed herein is atherosclerosis, chronic heart failure or congestive heart failure.

In still other embodiments, the arthritis disclosed herein is osteoarthritis, rheumarthritis, rheumatoid arthritis or juvenile rheumatoid arthritis.

In still other embodiments, the systemic inflammatory response syndrome disclosed herein is systemic inflammatory sepsis.

In still other embodiments, the inflammatory bowel disease disclosed herein is irritable bowel syndrome.

In still other embodiments, the hepatopathy disclosed herein is a liver autoimmune disease, autoimmune hepatitis, primary biliary cirrhosis, sclerosing cholangitis, autoimmune cholangitis, an alcoholic liver disease or a non-alcoholic fatty liver disease.

In still some embodiments, the non-alcoholic fatty liver disease is non-alcoholic simple fatty liver, non-alcoholic steatohepatitis, non-alcoholic fatty liver disease-related cryptogenic cirrhosis or primary liver cancer.

In still other embodiments, the respiratory disease disclosed herein is asthma, acute lung injury, acute respiratory distress syndrome, lung inflammation, a chronic obstructive pulmonary disease, bronchitis or bronchiectasis.

In still other embodiments, the eye disease disclosed herein is uveitis, iritis, retinitis, autoimmune ophthalmia, inflammation driven by angiogenesis and/or lymphogenesis, macular degeneration.

In still other embodiments, the skin disease disclosed herein is contact dermatitis, skin inflammation, psoriasis or eczema.

In still other embodiments, the neuritis disclosed herein is Parkinson's disease, Alzheimer's disease, vascular dementia, multiple sclerosis, chronic multiple sclerosis.

In some embodiments, the disease disclosed herein is cancer.

In other aspect, the invention relates to a method for inhibiting SSAO/VAP-1 activity by using the compound or pharmaceutical composition of the invention, the method comprises administering an effective therapeutic amount of the compound or pharmaceutical composition to a subject in need.

In other aspect, the invention relates to a method for preventing or treating the following diseases by using the compound or pharmaceutical composition of the invention, the method comprises administering an effective therapeutic amount of the compound or pharmaceutical composition to an subject, wherein the disease is inflammation and/or a disease related to inflammation, diabetes and/or a disease related to diabetes, a mental disorder, an ischemic disease, a vascular disease, fibrosis or tissue transplant rejection. Moreover, the compound provided by the present invention or the pharmaceutical composition thereof can be co-administered with other therapies or therapeutic agents. The mode of administration can be simultaneous, sequential or at certain time intervals.

The dosage of the compound or pharmaceutical composition required for the implementation of treatment, prevention or delay is usually dependent on the specific compound administered, the patient, the specific disease or condition and its severity, the route and frequency of administration, etc., and needs to be determined by the attending physician based on the specific situation. For example, when the compound or pharmaceutical composition provided by the present invention is administered by an intravenous route, it can be administered once a week or even at longer intervals.

In other aspect, provided herein is the compound or the pharmaceutical composition disclosed herein for use in inhibiting SSAO/VAP-1 activity.

In other aspect, the invention relates to the compound or the pharmaceutical composition disclosed herein for use in preventing, treating the following diseases, ameliorating the development or seizure of the following diseases, wherein the disease is inflammation and/or a disease related to inflammation, diabetes and/or a disease related to diabetes, a mental disorder, an ischemic disease, a vascular disease, fibrosis or tissue transplant rejection.

In some embodiments, the salt refers to a pharmaceutically acceptable salt. The phrase "pharmaceutically acceptable" refers to that the substance or composition must be chemically and/or toxicologically compatible with the other ingredients comprising a formulation, and/or the mammal being treated therewith.

The compounds of the present invention also include other salts of such compounds, which are not necessarily pharmaceutically acceptable salts, and can be used for preparing and/or purifying the compounds of the present invention and/or for isolating intermediates of the enantiomers of the compounds of the present invention.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have the structure depicted by the general formula given in the present invention, except that one or more atoms are replaced by an atom having a selected atomic mass or mass number. Examples of isotopes that can be incorporated into compounds of the invention include isotopes of hydrogen, carbon, nitrogen, oxygen, phosphorous, sulfur, fluorine, and chlorine, such as $_2$H, $^3$H, $^{11}$C, $^{13}$C, $^{14}$C, $^{15}$N, $^{18}$F, $^{31}$P, $^{32}$P, $^{36}$S, $^{37}$Cl, $^{125}$I, respectively.

Composition of the Compound of the Invention and Preparations and Administration The invention relates to a pharmaceutical composition comprising the compound of the present invention or the compound of the structure shown in the examples, or a stereoisomer, a geometric isomer, a tautomer, an N-oxide, a solvate, a metabolite, a pharmaceutically acceptable salt or a prodrug thereof. The pharmaceutical composition further comprises at least one pharmaceutically acceptable carrier, excipient, adjuvant, vehicle or a combination thereof, and optionally, other therapeutic and/or prophylactic ingredients. In some embodiments, the pharmaceutical composition comprises an effective amount of at least one pharmaceutically acceptable carrier, excipient, adjuvant or vehicle. The amount of the compound in the compositions disclosed herein is an effective and detectable amount for inhibiting SSAO/VAP-1 activity in biological samples or patients.

Pharmaceutically acceptable carriers may contain inert ingredients that do not unduly inhibit the biological activity of the compound. The pharmaceutically acceptable carrier should be biocompatible, for example, non-toxic, non-inflammatory, non-immunogenic or once administered to the patient without other adverse reactions or side effects. Standard pharmaceutical technology can be used.

As described above, the pharmaceutical composition or pharmaceutically acceptable composition of the present invention further comprises a pharmaceutically acceptable carrier, excipient, adjuvant or vehicle, which, as used herein, includes any solvents, diluents, liquid excipients, dispersants, suspending agents, surfactants, isotonic agents, thickeners, emulsifiers, preservatives, solid binders, lubricants and the like, as suited to the particular dosage form desired. Remington: The Science and Practice of Pharmacy, 21st ed., 2005, Lippincott Williams & Wilkins, Philadelphia, and Swarbrick et al., Encyclopedia of Pharmaceutical Technology, eds. 1988-1999, Marcel Dekker, New York, both of which are herein incorporated by reference in their entireties, discloses various carriers used in formulating pharmaceutically acceptable compositions and known techniques for the preparation thereof. Except insofar as any conventional carrier medium incompatible with the compounds disclosed herein, such as by producing any undesirable biological effect or otherwise interacting in a deleterious manner with any other components of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as Tween 80, phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, methyl cellulose, hydroxypropyl methyl cellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical composition of the present invention can be administered directly or in a pharmaceutical composition or pharmaceutical form along with a suitable carrier or excipient, which is well known in the art. The treatment method of the present invention may comprise administering an effective compound of the present invention to an individual in need. In some embodiments, the individual is a mammalian individual, and in other embodiments, the individual is a human individual.

The effective amount of the compound, pharmaceutical composition or drug of the present invention can be easily determined by routine test, and the most effective and convenient route of administration and the most suitable formulation can also be determined by routine test.

The compound or composition of the present invention may be administered by any suitable means, and the above-mentioned compounds and pharmaceutically acceptable compositions can be administered to humans or other animals orally, rectally, parenterally, intracisternally, intravaginally, intraperitoneally, topically (as by powder, ointment or drops) or by nasal sprays, etc., according to the severity of the disease.

Liquid dosage forms for oral administration include, but are not limited to, pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular cottonseed, groundnut, corn, germ, olive, castor and sesame oils), glycerol, tetrahydrofuryl alcohol, polyethylene glycols and fatty acid esters of sorbitan, and mixtures thereof. In addition to the inert diluent, the oral compositions may also contain adjuvants such as wetting agents, emulsifying or suspending agents, sweetening agents, flavoring agents and fragrances.

Injectable formulations can be formulated according to known techniques using suitable dispersing or wetting agents and suspending agents, for example, sterile injectable water or oil suspensions. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound or a composition described herein, it is often desirable to slow the absorption of the compound from subcutaneous or intramuscular injection. This may be accomplished by the use of a liquid suspension of crystalline or amorphous material having poor water solubility. The rate of absorption of the drug depends upon its rate of dissolution which, in turn, may depend upon crystal size and crystalline form. Alternatively, delayed absorption of a parenterally administered compound form is accomplished by dissolving or suspending the compound in an oil vehicle. Alternatively, injectable depot forms are made by forming microencapsule matrices of the compound in biodegradable polymers such as polylactide-polyglycolic acid. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders and granules. In such solid dosage forms, the active compounds are mixed with at least one pharmaceutically acceptable inert excipients or carriers, such as sodium citrate or dicalcium phosphate and/or (a) fillers or swelling agents such as starch, lactose, sucrose, glucose, mannitol and silicic acid, (b) adhesives such as carboxymethylcellulose, alginates, gelatin, polyethylene pyrrole ketone, sucrose and gum arabic, (c) moisturizing agents such as glycerol, (d) disintegrating agents such as agar, calcium carbonate, potato starch or tapioca starch, alginic acid, certain silicates and sodium carbonate, (e) blocker solution, such as paraffin, (f) absorption promoter such as quaternary ammonium compounds, (g) wetting agents such as cetyl alcohol and glycerol monostearate, (h)

absorbents such as kaolin and bentonite, (i) lubricants such as talc, calcium stearate, magnesium stearate, solid polyethylene glycol, laurylsodium sulfate, and mixtures thereof. In the case of capsules, tablets and pills, the pharmaceutical compositions may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compound may also take the form of a microseal with one or more of the above-mentioned excipients. In such solid dosage forms, the active compound may be mixed with at least one inert diluent, such as sucrose, lactose or starch. Generally, this dosage form may also contain additional substances in addition to inert diluents, such as tableting lubricants and other tableting aids, such as magnesium stearate and microcrystalline cellulose. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of the compounds of the present invention include ointments, ointments, creams, lotions, gels, powders, solutions, sprays, inhalants, or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with an non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carrier compounds for topical administration of the present invention include, but are not limited to, mineral oil, petrolatum oil, white petrolatum, propylene glycol, polyoxyethylene, polyoxypropylene compounds, emulsified waxes and water. Alternatively, the pharmaceutical composition may be formulated as a suitable lotion or cream containing the active components suspended or dissolved in one or more pharmaceutically acceptable carriers. Suitable carriers include, but are not limited to, mineral oil, sorbitan monostearate, polysorbate 60, cetyl ester wax, cetearyl alcohol, 2-octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Use of the Compounds and Pharmaceutical Compositions

The compound or the pharmaceutical composition disclosed herein can be used in the manufacture of a medicament for inhibiting SSAO/VAP-1.

The compound or the pharmaceutical composition disclosed herein can be used in preventing, treating or ameliorating a disease related to SSAO/VAP-1 protein or regulated by SSAO/VAP-1, the disease is inflammation and/or a disease related to inflammation, diabetes and/or a disease related to diabetes, a mental disorder, an ischemic disease, a vascular disease, fibrosis or tissue transplant rejection.

The compound or the pharmaceutical composition disclosed herein can be used in the manufacture of a medicament for preventing, treating or ameliorating a disease related to SSAO/VAP-1 protein or regulated by SSAO/VAP-1, the disease is inflammation and/or a disease related to inflammation, diabetes and/or a disease related to diabetes, a mental disorder, an ischemic disease, a vascular disease, fibrosis or tissue transplant rejection.

Provided herein is a method of treating, preventing or ameliorating a disease related to SSAO/VAP-1 protein or regulated by SSAO/VAP-1, and wherein the method comprises administering to the patent a therapeutically effective amount of the compound or the pharmaceutical composition described herein to a patient in need of treatment. The disease is inflammation and/or a disease related to inflammation, diabetes and/or a disease related to diabetes, a mental disorder, an ischemic disease, a vascular disease, fibrosis or tissue transplant rejection. Moreover, the compound provided by the present invention or the pharmaceutical composition thereof can be co-administered with other therapies or therapeutic agents. The mode of administration can be simultaneous, sequential or at certain time intervals.

Besides being useful for human treatment, these compounds are also useful for veterinary treatment of animals such as companion animals, exotic animals and farm animals, including mammals, rodents, and the like. In other embodiments, the animals disclosed herein include horses, dogs, and cats. As used herein, the compounds disclosed herein include the pharmaceutically acceptable derivatives thereof.

An "effective amount" or "effective dose" of the compound or pharmaceutically acceptable composition is an amount that is effective in treating or ameliorating the severity of one or more of the aforementioned disorders. The compounds and pharmaceutically acceptable compositions are effective administered in a fairly wide dose range. For example, the daily dose is from about 0.1 mg to 1000 mg per person, the compounds or pharmaceutically acceptable compositions can be administered in a single dose or in several divided doses a day. The compounds and compositions, according to the method disclosed herein, may be administered using any amount and any route of administration which is effective for treating or ameliorating the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents as discussed above.

General Synthesis and Determination Methods

To describe the invention, the following examples are listed. However, it should be understood that the present invention is not limited to these embodiments, but merely provides a method for practicing the present invention.

In the present invention, if the chemical name of the compound doesn't match the corresponding structure, the compound is characterized by the corresponding structure.

In the specification, the compound number in the examples, the compound number in the claims or the compound number in other positions in the specification are independent of each other. Wherein the compound in the activity test examples is the compound in the preparation examples with the same compound number.

Generally, the compounds disclosed herein may be prepared by methods described herein, wherein the substituents are as defined for Formula (I) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

The structures of the compounds were identified by nuclear magnetic resonance (e.g., $^1$H-NMR, $^{13}$C-NMR and/or $^{19}$F-NMR). $^1$H-NMR, $^{13}$C-NMR and 19F-NMR chemical shifts (6) were recorded as ppm ($10^{-6}$). Measure of $^1$H-NMR, $^{13}$C-NMR, $^{19}$F-NMR are performed, respectively, on Bruker Ultrashield-400 nuclear magnetic resonance spectrometer and Bruker Avance III HD 600 nuclear magnetic resonance spectrometer using deuterated chloroform ($CDCl_3$), deuterated methanol ($CD_3OD$ and MeOH-$d_4$) or deuterated DMSO (DMSO-$d_6$) as a solvent. TMS (0 ppm) or chloroform (7.25 ppm) is as the reference standard. When peak multiplicities were reported, the following abbreviations were used: s (singlet), d (doublet), t (triplet), m (multiplet), br (broadened), dd (doublet of doublets), dt (doublet of triplets), td (triplet of doublets), brs (broadened singlet). Coupling constants J, when given, were reported in Hertz (Hz).

Novasep pump 250 high performance liquid chromatography is generally used for preparation, purification or separation.

LC-MS spectra were determined on Agilen-6120 Quadrupole LC/MS mass spectrometer.

The silica gel used in column chromatography generally was Qingdao Ocean Chemical Factory 300 to 400 mesh silica gel.

The staring materials of the present invention were known or purchased from Shanghai Accela Company, Energy Company, J&K, Alfa Company and the like, or they could be prepared by the conventional synthesis methods in the prior art.

The term "nitrogen atmosphere" refers to such an atmosphere that a reaction flask was equipped with a balloon or a stainless steel autoclave filled with about 1 L nitrogen.

The term "hydrogen atmosphere" refers to such an atmosphere that a reaction flask was equipped with a balloon or a stainless steel autoclave filled with about 1 L hydrogen.

Unless otherwise stated, the solution used in the examples disclosed herein was an aqueous solution.

Unless otherwise stated, the reaction temperature was room temperature.

Unless otherwise stated, the room temperature was from 20° C. to 40° C.

The reaction process in the examples was monitored by thin layer chromatography (TLC). The solvent system for development of a TLC plate comprised dichloromethane and methanol, dichloromethane and ethyl acetate, petroleum ether and ethyl acetate. The volume ratio of the solvents in the solvent system was adjusted according to the polarity of the compounds.

The elution system of column chromatography comprised: A: petroleum ether and ethyl acetate, B: dichloromethane and ethyl acetate, C: dichloromethane and methanol. The volume ratio of the solvents in the elution system was adjusted according to the polarity of the compounds, and sometimes it was also adjusted by adding a basic agent such as aqueous ammonia or an acidic agent such as acetic acid.

HPLC refers to High Performance Liquid Chromatography; HPLC was determined on Agilent 1200DAD high pressure liquid chromatography spectrometer (Zorbax Eclipse Plus C18 150×4.6 mm chromatographic column).

The test condition of HPLC: the run time was 15-20 minutes (min); the column temperature was 35° C.; the detection was carried out at the wavelength of 210 nm and 254 nm using PDA detector;

Mobile phase: phase A: pH 2.5 potassium dihydrogen phosphate phase B: acetonitrile flow rate: 1.0 mL/min the gradient of mobile phase was shown in the Table A.

TABLE A

| Time | Gradient of Mobile Phase A | Gradient of Mobile Phase B |
|---|---|---|
| 0 min | 90% | 10% |
| 15 min | 30% | 70% |

The LC/MS/MS system used in biological analysis test comprises Agilent 1200 series vacuum degassing furnace, binary pumps, well-plate autosampler, thermostatted column compartment, the Agilent G6430 Triple Quadru pole Mass Spectrometer with an electrosprayionization (ESI) source. Quantitative analysis was carried out using MRM mode. The parameters for MRM transitions are in the Table B.

TABLE B

| Full scan | 50~1400 |
|---|---|
| Fragmentor | 230 V |
| Capillary voltage | 55 V |
| Temperature of dryer | 350° C. |
| Nebulizer | 0.28 MPa |
| Flow rate of dryer | 10 L/min |

An Agilent XDB-C18, 2.1×30 mm, 3.5 µM column was used for the analysis. 5 µL of the samples were injected. Analysis conditions: The mobile phase was 0.1% formic acid in water (A) and 0.1% formic acid in methanol (B). The flow rate was 0.4 mL/min. And the gradient of mobile phase was shown in the Table C.

TABLE C

| Time | Gradient of Mobile Phase B |
|---|---|
| 0.5 min | 5% |
| 1.0 min | 95% |
| 2.2 min | 95% |
| 2.3 min | 5% |
| 5.0 min | Stop |

Alternatively, an Agilent 6330 series LC/MS/MS spectrometer equipped with G1312A binary pumps, a G1367A autosampler and a G1314C UV detector were used in the analysis. An ESI source was used on the LC/MS/MS spectrometer. Standard solutions were used to perform appropriate cation model processing and MRM conversion for each analyte for optimal analysis. A Capcell MP-C18 100× 4.6 mm I.D., 5 µM column (Phenomenex, Torrance, California, USA) was used during the analysis. The mobile phase was 5 mM ammonia acetate, 0.1% MeOH in water (A): 5 mM ammonia acetate, 0.1% MeOH in acetonitrile (B) (70:30, v/v). The flow rate was 0.6 mL/min. Column was maintained at ambient temperature. 20 µL of the samples were injected.

The following abbreviations are used throughout the specification:

| DMSO-$d_6$: | dimethylsulfoxide-d6; | Boc: | tert-butoxycarbonyl; |
|---|---|---|---|
| $CDCl_3$: | chloroform-d; | % wt, mass %: | weight percent; |
| $CD_3OD$: | methanol-d; | mL: | milliliter |
| µL: | microliter; | mol/L: | mole per liter; |
| mol: | mole; | mmol: | millimoles; |
| g: | gram; | h: | hour; |
| $H_2$: | hydrogen; | $N_2$: | nitrogen; |
| min: | minute; | MPa : | megapascal; |
| HATU: | 2-(7-aza-1H-benzotriazole-1-yl)-1,1,3,3-tetramethyluronium hexafluorophosphate. | | |

General Synthetic Procedures

Typical synthetic steps for preparing the disclosed compounds of the present invention are shown in the following synthetic schemes 1. Unless otherwise stated, each R4, Rc, R5 and $R^6$ has the definition as described in the present invention.

Synthetic scheme 1

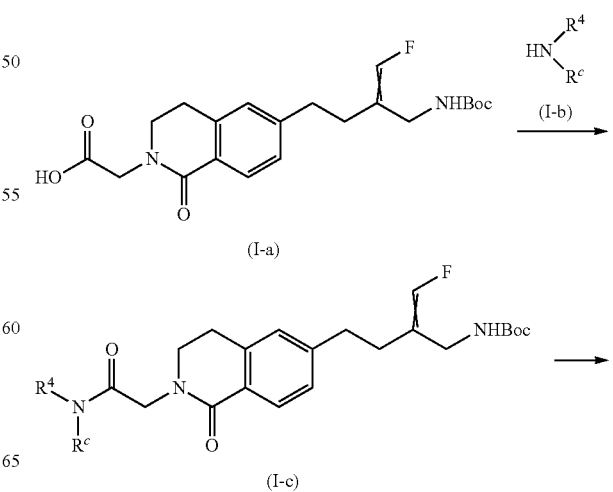

-continued

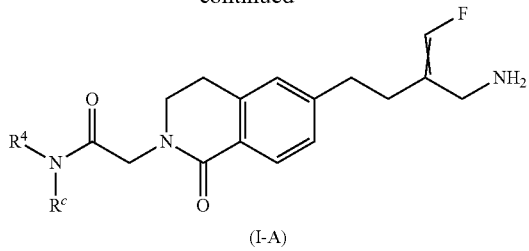

(I-A)

The compound having Formula (I-A) can be prepared by the general synthesis method described in synthesis scheme 1. First, compound (I-a) undergoes condensation reaction with compound (I-b) in the presence of a condensing agent (such as N,N-carbonyldiimidazole, HATU, etc.) to obtain compound (I-c); then, the amino protecting group -Boc of compound (I-c) can be removed to obtain the target compound having Formula (I-A). In general, free amino compounds, i.e. the target compounds having Formula (I-A), are converted into acid addition salts for facilitate treatment and improvement of chemical stability. Some non-limited examples of the acid addition salts include hydrochloride, hydrobromate, phosphate, oxalate, maleate, tartrate, citrate, malate and methanesulfonate.

Synthetic scheme 2

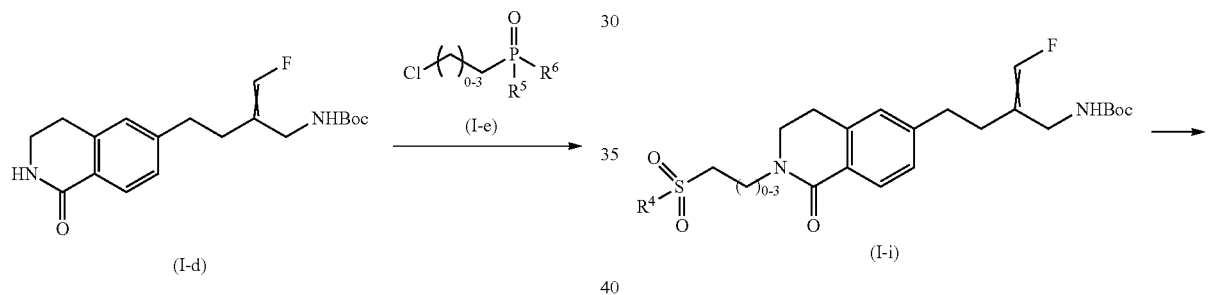

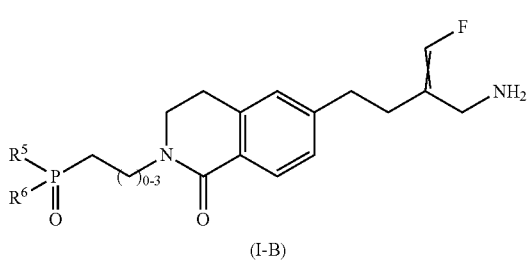

(I-B)

The compound having Formula (I-B) can be prepared by the general synthesis method described in synthesis scheme 2, wherein R5 and R6 are not OH. First, compound (I-d) undergoes substitution reaction with compound (I-e) under basic conditions (such as sodium hydride) to obtain compound (I-f); then, the amino protecting group -Boc of compound (I-f) can be removed to obtain the target compound having Formula (I-B). In general, free amino compounds, i.e. the target compounds having Formula (I-B), are converted into acid addition salts for facilitate treatment and improvement of chemical stability. Some non-limited examples of the acid addition salts include hydrochloride, hydrobromate, phosphate, oxalate, maleate, tartrate, citrate, malate, and methanesulfonate.

Synthetic scheme 3

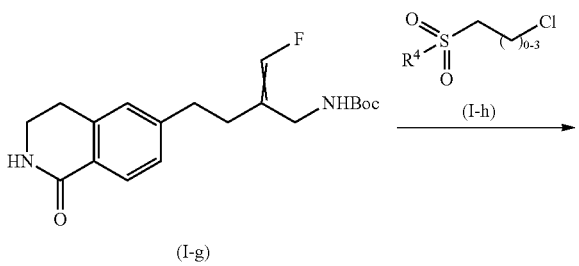

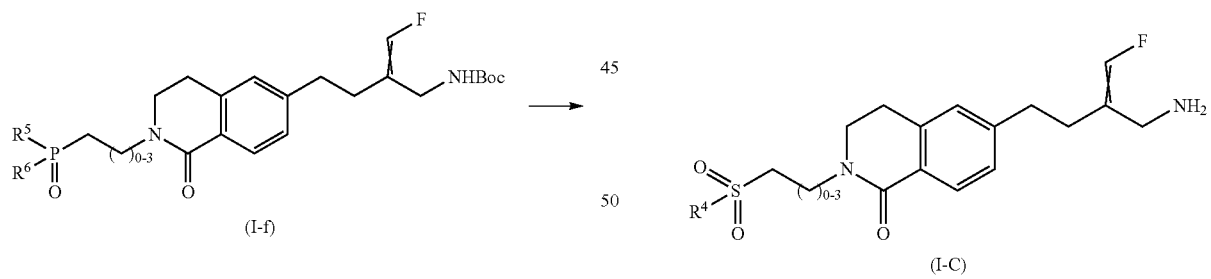

The compound having Formula (I-C) can be prepared by the general synthesis method described in synthesis scheme 3. First, compound (I-g) undergoes substitution reaction with compound (I-h) under basic conditions (such as sodium hydride) to obtain compound (I-i); then, the amino protecting group -Boc of compound (I-i) can be removed to obtain the target compound having Formula (I-C). In general, free amino compounds, i.e. the target compounds having Formula (I-C), are converted into acid addition salts for facilitate treatment and improvement of chemical stability. Some non-limited examples of the acid addition salts include hydrochloride, hydrobromate, phosphate, oxalate, maleate, tartrate, citrate, malate, and methanesulfonate.

EXAMPLES

Preparation Example

Example 1  2-[6-[(E)-2-(aminomethyl)-3-fluoro-allyloxy]-1-oxo-3,4-dihydroisoquinolin-2-yl] acetamide hydrochloride

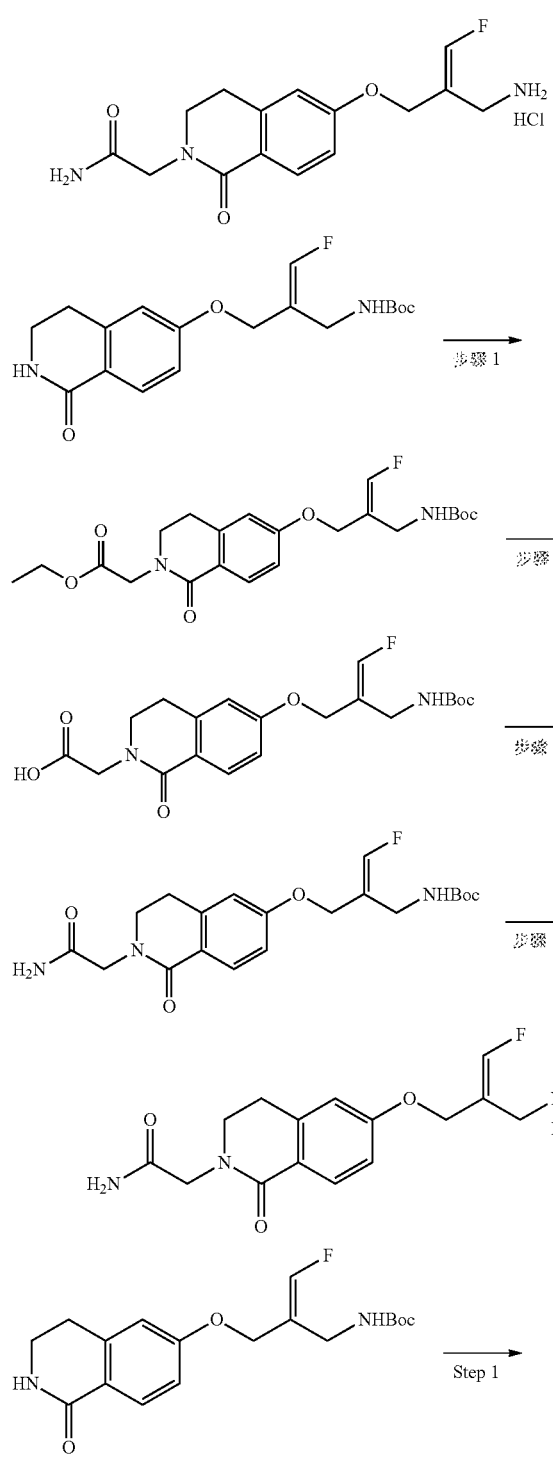

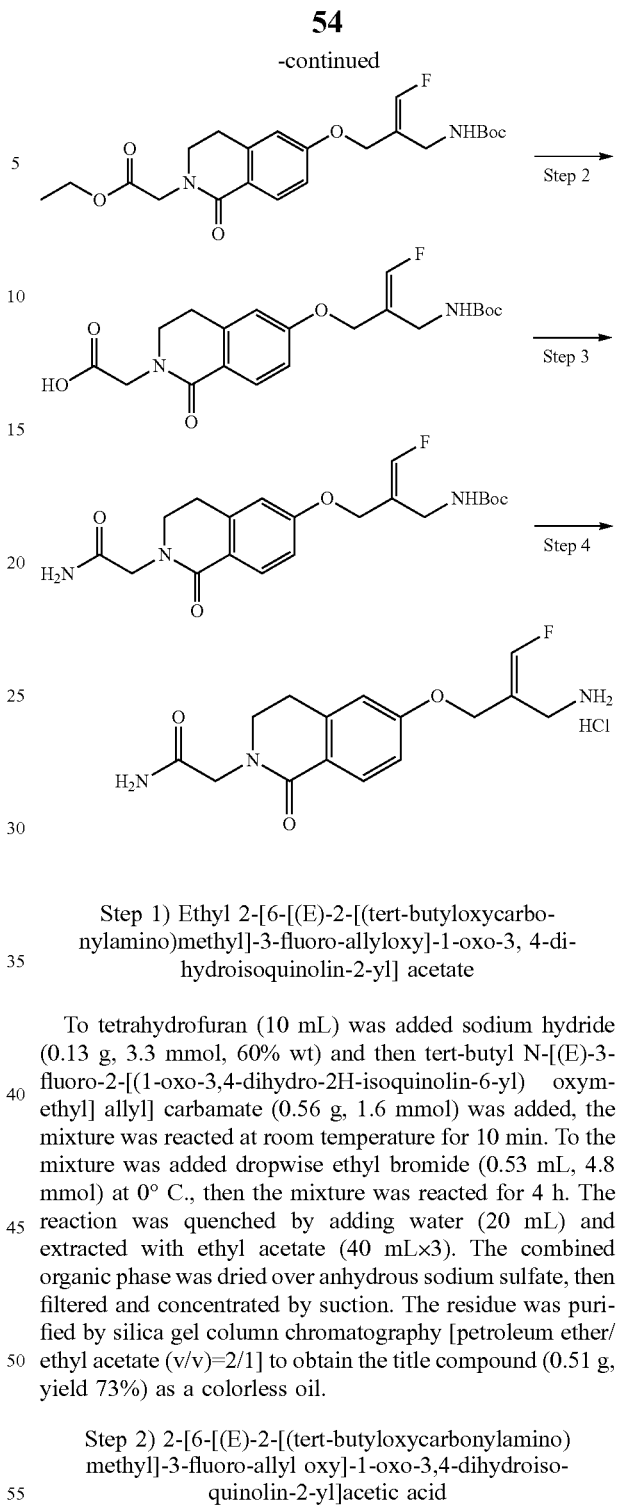

Step 1) Ethyl 2-[6-[(E)-2-[(tert-butyloxycarbonylamino)methyl]-3-fluoro-allyloxy]-1-oxo-3, 4-dihydroisoquinolin-2-yl] acetate To tetrahydrofuran (10 mL) was added sodium hydride (0.13 g, 3.3 mmol, 60% wt) and then tert-butyl N-[(E)-3-fluoro-2-[(1-oxo-3,4-dihydro-2H-isoquinolin-6-yl) oxymethyl] allyl] carbamate (0.56 g, 1.6 mmol) was added, the mixture was reacted at room temperature for 10 min. To the mixture was added dropwise ethyl bromide (0.53 mL, 4.8 mmol) at 0° C., then the mixture was reacted for 4 h. The reaction was quenched by adding water (20 mL) and extracted with ethyl acetate (40 mL×3). The combined organic phase was dried over anhydrous sodium sulfate, then filtered and concentrated by suction. The residue was purified by silica gel column chromatography [petroleum ether/ethyl acetate (v/v)=2/1] to obtain the title compound (0.51 g, yield 73%) as a colorless oil.

Step 2) 2-[6-[(E)-2-[(tert-butyloxycarbonylamino)methyl]-3-fluoro-allyl oxy]-1-oxo-3,4-dihydroisoquinolin-2-yl]acetic acid Ethyl 2-[6-[(E)-2-[(tert-butyl oxycarbonyl amino) methyl]-3-fluoro-allyloxy]-1-oxo-3,4-dihydroisoquinoline-2-yl] acetate (0.86 g, 2.0 mmol) was dissolved in a mixed solution of 1,4-dioxane (15 mL) and water (15 mL), then lithium hydroxide monohydrate (0.84 g, 20 mmol) was added into the solution. The mixture was reacted at room temperature for 4 h. Water (15 mL) was added to the reaction mixture, the pH was adjusted by acetic acid at 4, and then the mixture was extracted with ethyl acetate (50 mL×3). The combined organic phase was washed with saturated sodium chloride solution (20 mL). The resulting product was dried over anhydrous sodium sulfate, filtered and concentrated by suction to obtain the title compound (0.80 g, yield 99%) as a white solid.

Step 3) Tert-butyl N-[(E)-2-[[2-(2-amino-2-oxo-ethyl)-1-oxo-3,4-dihydroisoquinolin-6-yl]oxymethyl]-3-fluoro-allyl] carbamate 2-[6-[(E)-2-[(tert-butyloxycarbonylamino)methyl]-3-fluoro-allyloxy]-1-oxo-3,4-dihydroisoquinoline-2-yl]acetic acid (140 mg, 0.34 mmol) was dissolved in anhydrous tetrahydrofuran (6 mL), and then carbonyldiimidazole (147 mg, 0.89 mmol) was added, and the reaction was carried out at room temperature for 2 h. To the mixture were added ammonia (0.3 mL, 2 mmol) and triethylamine (0.3 mL, 2 mmol) and the reaction was carried out at room temperature for 15 h. Water (10 mL) was added to the reaction solution, and the mixture was extracted with ethyl acetate (30 mL×3). The combined organic phase was washed with water (30 mL×3) and saturated sodium chloride solution (10 mL×3) successively. The resulting product was dried with anhydrous sodium sulfate, filtered and concentrated by suction. The obtained residue was purified by silica gel column chromatography [dichloromethane/methanol (v/v)=20/1] to obtain the title compound (121 mg, yield 87%) as a white solid.

MS (ESI, pos. ion) m/z: 430.3[M+Na]$^+$.

Step 4) 2-[6-[(E)-2-(aminomethyl)-3-fluoro-allyloxy]-1-oxo-3,4-dihydroisoquinolin-2-yl] acetamide hydrochloride Tert-Butyl N-[(E)-2-[[2-(2-amino-2-oxo-ethyl)-1-oxo-3,4-dihydroisoquinolin-6-yl]oxymethyl]-3-fluoro-allyl]carbamate (121 mg, 0.30 mmol) was dissolved in ethyl acetate (1 mL), then a solution of hydrogen chloride in ethyl acetate (6 mL, 3 mol/L) was added. The mixture was reacted at room temperature for 1 h. The reaction solution was concentrated to obtain the title compound (102 mg, yield 99%, HPLC purity 97.17%) as a white solid.

MS (ESI, pos. ion) m/z: 308.0 [M-Cl]$^+$;

$^1$H NMR (400 MHz, DMSO-d$_6$) δ (ppm) 8.34 (s, 3H), 7.80 (d, J=7.4 Hz, 1H), 7.33 (d, J=90.8 Hz, 2H), 7.15-6.57 (m, 3H), 4.70 (s, 2H), 4.05 (s, 2H), 3.57 (s, 4H), 2.96 (s, 2H).

Example 2 2-[6-[(Z)-2-(aminomethyl)-3-fluoro-allyloxy]-1-oxo-3,4-dihydroisoquinolin-2-yl] acetamide hydrochloride

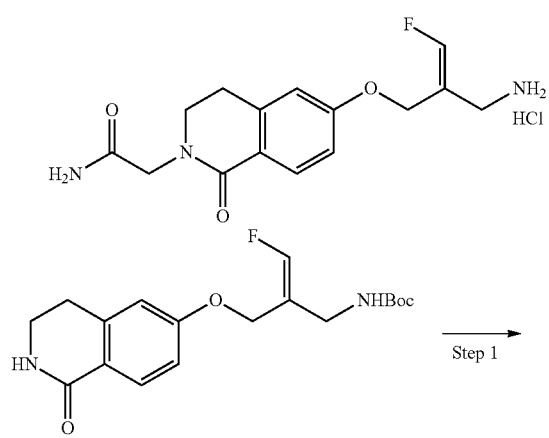

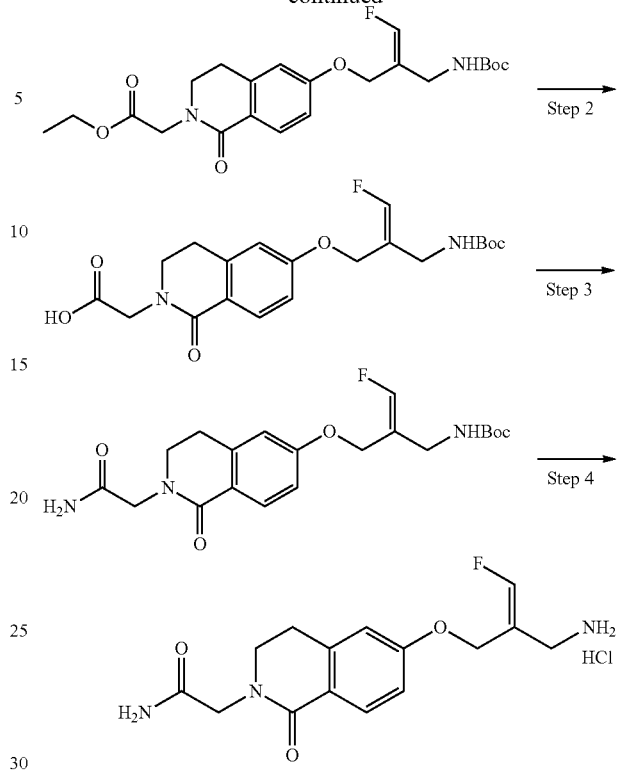

Step 1) Ethyl 2-[6-[(Z)-2-[(tert-butyloxycarbonylamino)methyl]-3-fluoro-allyloxy]-1-oxo-3,4-dihydroisoquinolin-2-yl] acetate To tetrahydrofuran (20 mL) was added sodium hydride (0.26 g, 6.6 mmol, 60% wt) and then tert-butyl N—[(Z)-3-fluoro-2-[(1-oxo-3,4-dihydro-2H-isoquinolin-6-yl)oxymethyl]allyl] carbamate (1.12 g, 3.2 mmol) was added, the mixture was reacted at room temperature for 10 min. To the mixture was added ethyl bromide (1.1 mL, 9.6 mmol) dropwise at 0° C., then the mixture was reacted for 4 h. The reaction was quenched by adding water (20 mL) and extracted with ethyl acetate (40 mL×3). The combined organic phase was dried over anhydrous sodium sulfate, then filtered and concentrated by suction. The residue was purified by silica gel column chromatography [petroleum ether/ethyl acetate (v/v)=2/1] to obtain the title compound (1.0 g, yield 72%) as a colorless oil.

Step 2) 2-[6-[(Z)-2-[(tert-butyloxycarbonylamino) methyl]-3-fluoro-allyloxy]-1-oxo-3,4-dihydroisoquinoline-2-yl]acetic acid Ethyl 2-[6-[(Z)-2-[(tert-butyloxycarbonylamino)methyl]-3-fluoro-allyl oxy]-1-oxo-3,4-dihydroisoquinolin e-2-yl] acetate (1.0 g, 2.3 mmol) was dissolved in a mixed solution of 1,4-dioxane (15 mL) and water (15 mL), and then lithium hydroxide monohydrate (0.84 g, 20 mmol) was added, the mixture was reacted at room temperature for 4 hours. Water (15 mL) was added to the reaction mixture, the pH was adjusted by acetic acid at 4, and then the mixture was extracted with ethyl acetate (50 mL×3). The combined organic phase was washed with saturated sodium chloride solution (20 mL). The resulting product was dried over anhydrous sodium sulfate, then filtered and concentrated by suction to obtain the title compound (0.94 g, yield 99%) as a white solid.

Step 3) Tert-butyl N—[(Z)-2-[[2-(2-amino-2-oxo-ethyl)-1-oxo-3,4-dihydroisoquinolin-6-yl]oxymethyl]-3-fluoro-allyl] carbamate 2-[6-[(Z)-2-[(tert-butyloxycarbonylamino)methyl]-3-fluoro-allyl oxy]-1-oxo-3,4-dihydroisoquinoline-2-yl]acetic acid (140 mg, 0.34 mmol) was dissolved in anhydrous tetrahydrofuran (6 mL), and then carbonyldiimidazole (147 mg, 0.89 mmol) was added. The reaction was carried out at room temperature for 2 hours. To the mixture were added ammonia (0.3 mL, 2 mmol) and triethylamine (0.3 mL, 2 mmol), and the reaction was carried out at room temperature for 15 h. Water (10 mL) was added to the reaction solution, and the mixture was extracted with ethyl acetate (30 mL×3). The combined organic phase was washed with water (30 mL×3) and saturated sodium chloride solution (10 mL×3) successively. The resulting product was dried with anhydrous sodium sulfate, then filtered and concentrated by suction. The obtained residue was purified by silica gel column chromatography [dichloromethane/methanol (v/v)=20/1] to obtain the title compound (110 mg, yield 79%) as a white solid.

MS (ESI, pos. ion) m/z: 430.2 [M+Na]$^+$.

Step 4) 2-[6-[(Z)-2-(aminomethyl)-3-fluoro-allyloxy]-1-oxo-3,4-dihydroisoquinolin-2-yl]acetamide hydrochloride Tert-Butyl N—[(Z)-2-[[2-(2-amino-2-oxo-ethyl)-1-oxo-3,4-dihydroisoquinolin-6-yl] oxymethyl]-3-fluoro-allyl] carbamate (148 mg, 0.36 mmol) was dissolved in ethyl acetate (1 mL), a solution of hydrogen chloride in ethyl acetate (6 mL, 3 mol/L) was added. The mixture was reacted at room temperature for 1 h. The reaction solution was concentrated to obtain the title compound (124 mg, yield 99%, HPLC purity 85.46%) as a white solid.

MS (ESI, pos. ion) m/z: 308.0 [M−Cl]$^+$;

$^1$H NMR (400 MHz, DMSO-d$_6$) δ (ppm) 8.30 (s, 3H), 7.81 (d, J=7.9 Hz, 1H), 7.39 (d, J=44.0 Hz, 2H), 7.15-6.86 (m, 3H), 4.80 (s, 2H), 4.05 (s, 2H), 3.54 (s, 4H), 2.96 (s, 2H).

Example 3 2-[6-[(E)-2-(aminomethyl)-3-fluoro-allyloxy]-1-oxo-3,4-dihydroisoquinolin-2-yl]-N-methyl-acetamide hydrochloride

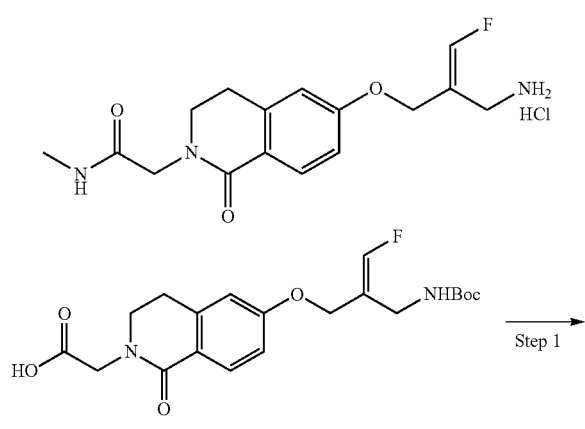

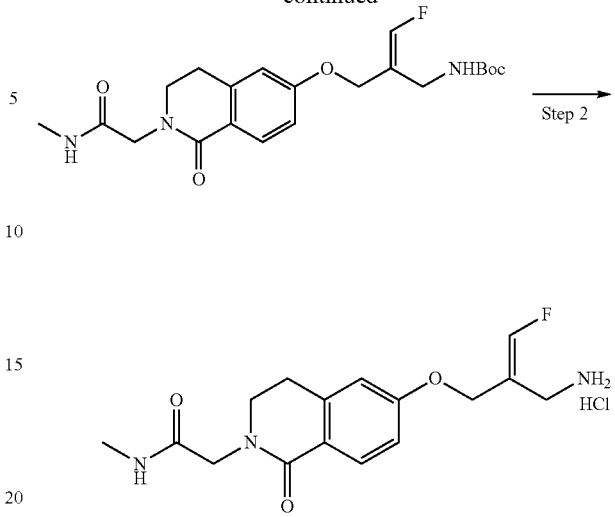

Step 1) Tert-butyl N-[(E)-3-fluoro-2-[[2-[2-(methyl amino)-2-oxo-ethyl]-1-oxo-3,4-dihydroisoquinoline-6-yl]oxymethyl]allyl] carbamate 2-[6-[(E)-2-[(tert-butyloxycarbonylamino)methyl]-3-fluoro-allyl oxy]-1-oxo-3,4-dihydroisoquinoline-2-yl]acetic acid (93 mg, 0.23 mmol) was dissolved in anhydrous tetrahydrofuran (6 mL), and then carbonyldiimidazole (97 mg, 0.59 mmol) was added, and the mixture was reacted at room temperature for 2 hours. To the mixture were added methylamine (0.2 mL, 2 mmol) and triethylamine (0.2 mL, 1 mmol) dropwise, the reaction was carried out at room temperature for 15 hours. Water (10 mL) was added to the reaction solution, and the mixture was extracted with ethyl acetate (30 mL×3). The combined organic phase was washed with water (30 mL×3) and saturated sodium chloride solution (10 mL×3) successively. The resulting product was dried with anhydrous sodium sulfate, then filtered and concentrated by suction. The obtained residue was purified by silica gel column chromatography [dichloromethane/methanol (v/v)=20/1] to obtain the title compound (70 mg, yield 73%) as a white solid.

MS (ESI, pos. ion) m/z: 444.1[M+Na]+.

Step 2) 2-[6-[(E)-2-(aminomethyl)-3-fluoro-allyloxy]-1-oxo-3,4-dihydroisoquinolin-2-yl]-N-methyl-acetamide hydrochloride Tert-Butyl N-[(E)-3-fluoro-2-[[2-[2-(methylamino)-2-oxo-ethyl]-1-oxo-3,4-dihydroisoquinoline-6-yl]oxymethyl] allyl] carbamate (70 mg, 0.17 mmol) was dissolved in ethyl acetate (1 mL), and then a solution of hydrogen chloride in ethyl acetate (6 mL, 3 mol/L) was added. The mixture was reacted at room temperature for 1 hour. The reaction solution was concentrated to obtain the title compound (59 mg, yield 99%, HPLC purity 98.09%) as a white solid.

MS (ESI, pos. ion) m/z: 322.1 [M−Cl]$^+$;

$^1$H NMR (400 MHz, DMSO-d$_6$) δ (ppm) 8.40 (s, 3H), 7.93 (s, 1H), 7.79 (d, J=7.2 Hz, 1H), 7.31 (d, J=82.1 Hz, 1H), 7.05-6.81 (m, 2H), 4.71 (s, 2H), 4.05 (s, 2H), 3.57 (m, 4H), 2.96 (s, 2H), 2.59 (s, 3H).

Example 4 2-[6-[(Z)-2-(aminomethyl)-3-fluoro-allyloxy]-1-oxo-3,4-dihydroisoquinolin-2-yl]-N-methyl-acetamide hydrochloride

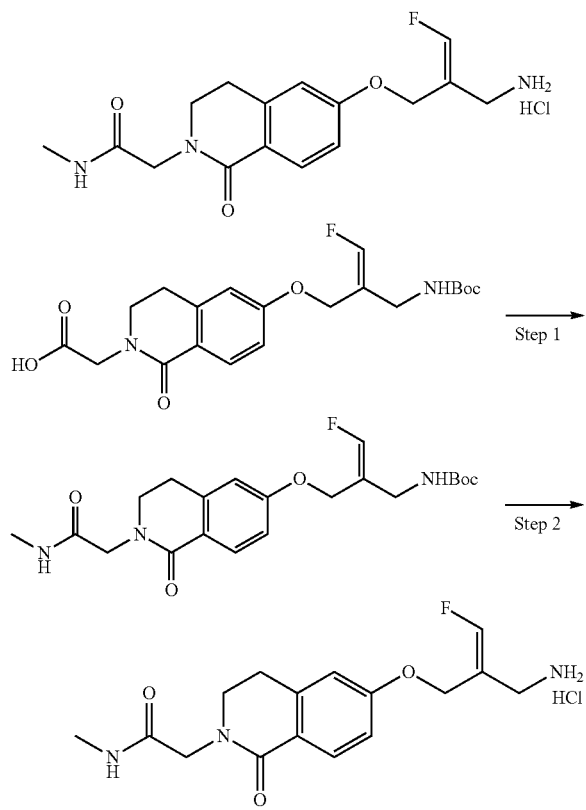

Step 1) Tert-butyl N-[(E)-3-fluoro-2-[[2-[2-(methyl-amino)-2-oxo-ethyl]-1-oxo-3,4-dihydroisoquinoline-6-yl]oxymethyl]allyl] carbamate 2-[6-[(Z)-2-[(tert-butyloxycarbonylamino)methyl]-3-fluoro-allyl oxy]-1-oxo-3,4-dihydroisoquinoline-2-yl]acetic acid (93 mg, 0.23 mmol) was dissolved in anhydrous tetrahydrofuran (6 mL), and then carbonyldiimidazole (97 mg, 0.59 mmol) was added, and the mixture was reacted at room temperature for 2 hours. To the mixture were added methylamine (0.2 mL, 2 mmol) and triethylamine (0.2 mL, 1 mmol) dropwise, the reaction was carried out at room temperature for 15 hours. Water (10 mL) was added to the reaction solution, and the mixture was extracted with ethyl acetate (30 mL×3). The combined organic phase was washed with water (30 mL×3) and saturated sodium chloride solution (10 mL×3) successively. The resulting product was dried with anhydrous sodium sulfate, then filtered and concentrated by suction. The obtained residue was purified by silica gel column chromatography [dichloromethane/methanol (v/v)=20/1] to obtain the title compound (80 mg, yield 83%) as a white solid.

MS (ESI, pos. ion) m/z: 422.0 [M+H]⁺.

Step 2) 2-[6-[(Z)-2-(aminomethyl)-3-fluoro-ally-loxy]-1-oxo-3,4-dihydroisoquinolin-2-yl]-N-methyl-acetamide hydrochloride Tert-Butyl N—[(Z)-3-fluoro-2-[[2-[2-(methylamino)-2-oxo-ethyl]-1-oxo-3,4-dihydroisoquinoline-6-yl]oxymethyl] allyl] carbamate (116 mg, 0.28 mmol) was dissolved in ethyl acetate (1 mL), and then a solution of hydrogen chloride in ethyl acetate (6 mL, 3 mol/L) was added. The mixture was reacted at room temperature for 1 hour. The reaction solution was concentrated to obtain the title compound (98 mg, yield 99%, HPLC purity 97.54%) as a white solid.

MS (ESI, pos. ion) m/z: 322.1 [M−Cl]⁺;

¹H NMR (400 MHz, DMSO-d₆) δ (ppm) 8.39 (s, 3H), 7.94 (s, 1H), 7.79 (d, J=7.7 Hz, 1H), 7.24 (d, J=81.9 Hz, 1H), 7.07-6.79 (m, 2H), 4.81 (s, 2H), 4.05 (s, 2H), 3.70 (m, 4H), 2.96 (s, 2H), 2.59 (s, 3H).

Example 5 2-[6-[(E)-2-(aminomethyl)-3-fluoro-allyloxy]-1-oxo-3,4-dihydroisoquinolin-2-yl]-N-ethyl-acetamide hydrochloride

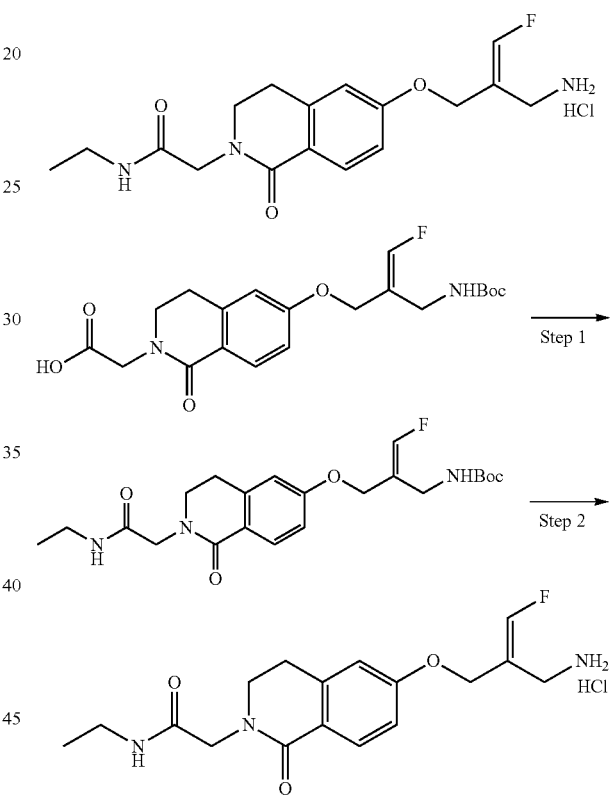

Step 1) Tert-butyl N-[(E)-3-fluoro-2-[[2-[2-(ethyl amino)-2-oxo-ethyl]-1-oxo-3,4-dihydroisoquinoline-6-yl]oxymethyl]allyl] carbamate 2-[6-[(E)-2-[(tert-butyloxycarbonylamino)methyl]-3-fluoro-allyl oxy]-1-oxo-3,4-dihydroisoquinoline-2-yl]acetic acid (93 mg, 0.23 mmol) was dissolved in anhydrous tetrahydrofuran (6 mL), and then carbonyldiimidazole (97 mg, 0.59 mmol) was added, and the mixture was reacted at room temperature for 2 hours. To the mixture were added methylamine (0.11 mL, 1.4 mmol) and triethylamine (0.2 mL, 1 mmol) dropwise, the reaction was carried out at room temperature for 15 hours. Water (10 mL) was added to the reaction solution, and the mixture was extracted with ethyl acetate (30 mL×3). The combined organic phase was washed with water (30 mL×3) and saturated sodium chloride solution (10 mL×3) successively. The resulting product was dried with anhydrous sodium sulfate, then filtered and concentrated by suction. The obtained residue was purified by silica gel column chromatography [dichloromethane/methanol (v/v)=20/1] to obtain the title compound (90 mg, yield 90%) as a white solid.

MS (ESI, pos. ion) m/z: 458.1[M+Na]+.

Step 2) 2-[6-[(E)-2-(aminomethyl)-3-fluoro-allyloxy]-1-oxo-3,4-dihydroisoquinolin-2-yl]-N-ethyl-acetamide hydrochloride Tert-Butyl N-[(E)-3-fluoro-2-[[2-[2-(ethylamino)-2-oxo-ethyl]-1-oxo-3,4-dihydroisoquinoline-6-yl]oxymethyl]allyl] carbamate (90 mg, 0.21 mmol) was dissolved in ethyl acetate (1 mL), and then a solution of hydrogen chloride in ethyl acetate (6 mL, 3 mol/L) was added. The mixture was reacted at room temperature for 1 hour. The reaction solution was concentrated to obtain the title compound (71 mg, yield 92%, HPLC purity 98.07%) as a white solid.

MS (ESI, pos. ion) m/z: 336.3 [M−Cl]+;
$^1$H NMR (400 MHz, DMSO-$d_6$) δ (ppm) 8.41 (s, 3H), 8.18-7.72 (m, 2H), 7.33 (d, J=82.1 Hz, 1H), 7.18-6.61 (m, 2H), 4.72 (s, 2H), 4.06 (s, 2H), 3.56 (s, 4H), 3.09 (s, 2H), 2.97 (s, 2H), 1.02 (s, 3H).

Example 6 2-[6-[(Z)-2-(aminomethyl)-3-fluoro-allyloxy]-1-oxo-3,4-dihydroisoquinolin-2-yl]-N-ethyl-acetamide hydrochloride

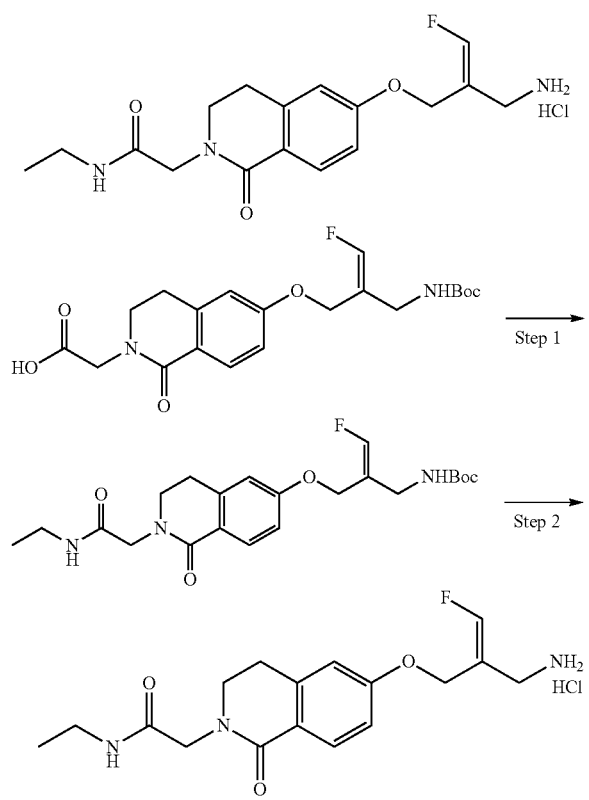

Step 1) Tert-butyl N—[(Z)-3-fluoro-2-[[2-[2-(ethyl amino)-2-oxo-ethyl]-1-oxo-3,4-dihydroisoquinoline-6-yl]oxymethyl]allyl] carbamate 2-[6-[(Z)-2-[(tert-butyloxycarbonylamino)methyl]-3-fluoro-allyl oxy]-1-oxo-3,4-dihydroisoquinoline-2-yl]acetic acid (93 mg, 0.23 mmol) was dissolved in anhydrous tetrahydrofuran (6 mL), and then carbonyldiimidazole (97 mg, 0.59 mmol) was added, and the mixture was reacted at room temperature for 2 hours. To the mixture were added methylamine (0.11 mL, 1.4 mmol) and triethylamine (0.2 mL, 1 mmol) dropwise, the reaction was carried out at room temperature for 15 hours. Water (10 mL) was added to the reaction solution, and the mixture was extracted with ethyl acetate (30 mL×3). The combined organic phase was washed with water (30 mL×3) and saturated sodium chloride solution (10 mL×3) successively. The resulting product was dried with anhydrous sodium sulfate, then filtered and concentrated by suction. The obtained residue was purified by silica gel column chromatography [dichloromethane/methanol (v/v)=20/1] to obtain the title compound (98 mg, yield 98%) as a white solid.

MS (ESI, pos. ion) m/z: 436.3 [M+H]+.

Step 2) 2-[6-[(Z)-2-(aminomethyl)-3-fluoro-allyloxy]-1-oxo-3,4-dihydroisoquinolin-2-yl]-N-ethyl-acetamide hydrochloride Tert-Butyl N—[(Z)-3-fluoro-2-[[2-[2-(ethylamino)-2-oxo-ethyl]-1-oxo-3,4-dihydroisoquinoline-6-yl]oxymethyl]allyl] carbamate (146 mg, 0.34 mmol) was dissolved in ethyl acetate (1 mL), and then a solution of hydrogen chloride in ethyl acetate (6 mL, 3 mol/L) was added. The mixture was reacted at room temperature for 1 hour. The reaction solution was concentrated to obtain the title compound (120 mg, yield 96%, HPLC purity 96.77%) as a white solid.

MS (ESI, pos. ion) m/z: 336.2 [M−Cl]+;
$^1$H NMR (400 MHz, DMSO-$d_6$) δ (ppm) 8.40 (s, 3H), 8.15-7.69 (m, 2H), 7.25 (d, J=82.0 Hz, 1H), 7.10-6.65 (m, 2H), 4.82 (s, 2H), 4.06 (s, 2H), 3.55 (s, 4H), 3.09 (s, 2H), 2.97 (s, 2H), 1.02 (s, 3H).

Example 7 2-[6-[(E)-2-(aminomethyl)-3-fluoro-allyloxy]-1-oxo-3,4-dihydroisoquinolin-2-yl]-N,N-dimethyl-acetamide hydrochloride

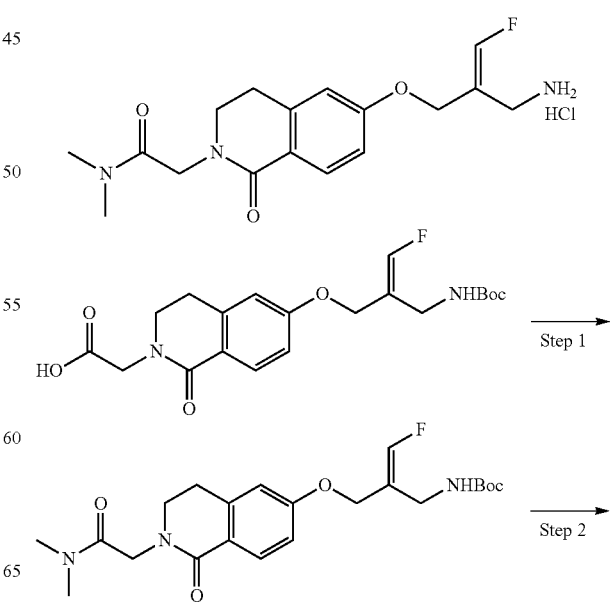

-continued

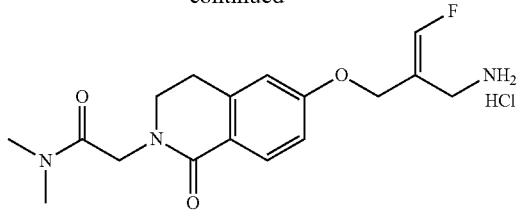

Step 1) Tert-butyl N-[(E)-2-[[2-[2-(dimethylamino)-2-oxo-ethyl]-1-oxo-3,4-dihydroisoquinolin-6-yl]oxymethyl]-3-fluoro-allyl]carbamate 2-[6-[(E)-2-[(tert-butyloxycarbonylamino)methyl]-3-fluoro-allyl oxy]-1-oxo-3,4-dihydroisoquinoline-2-yl]acetic acid (93 mg, 0.23 mmol) was dissolved in anhydrous tetrahydrofuran (6 mL), and then carbonyldiimidazole (97 mg, 0.59 mmol) was added, and the mixture was reacted at room temperature for 2 hours. To the mixture were added dimethylamine (0.11 mL, 1.4 mmol) and triethylamine (0.2 mL, 1 mmol) dropwise, the reaction was carried out at room temperature for 15 hours. Water (10 mL) was added to the reaction solution, and the mixture was extracted with ethyl acetate (30 mL×3). The combined organic phase was washed with water (30 mL×3) and saturated sodium chloride solution (10 mL×3) successively. The resulting product was dried with anhydrous sodium sulfate, then filtered and concentrated by suction. The obtained residue was purified by silica gel column chromatography [dichloromethane/methanol (v/v)=20/1] to obtain the title compound (91 mg, yield 92%) as a white solid.

MS (ESI, pos. ion) m/z: 458.1[M+Na]+.

Step 2) 2-[6-[(E)-2-(aminomethyl)-3-fluoro-allyloxy]-1-oxo-3,4-dihydroisoquinolin-2-yl]-N, N-dimethyl-acetamide hydrochloride Tert-Butyl N-[(E)-2-[[2-[2-(dimethylamino)-2-oxo-ethyl]-1-oxo-3,4-dihydroisoquinolin-6-yl]oxymethyl]-3-fluoro-allyl]carbamate (117 mg, 0.27 mmol) was dissolved in ethyl acetate (1 mL), and then a solution of hydrogen chloride in ethyl acetate (6 mL, 3 mol/L) was added. The mixture was reacted at room temperature for 1 hour. The reaction solution was concentrated to obtain the title compound (96 mg, yield 96%, HPLC purity 91.86%) as a white solid.

MS (ESI, pos. ion) m/z: 336.1 [M−Cl]+;

$^1$H NMR (400 MHz, DMSO-$d_6$) δ (ppm) 8.35 (s, 3H), 7.78 (s, 1H), 7.32 (d, J=81.6 Hz, 1H), 6.91 (s, 2H), 4.70 (s, 2H), 4.32 (s, 2H), 4.02 (s, 2H), 3.41-3.25 (m, 4H), 2.98 (s, 3H), 2.82 (s, 3H).

Example 8 2-[6-[(Z)-2-(aminomethyl)-3-fluoro-allyloxy]-1-oxo-3,4-dihydroisoquinolin-2-yl]-N,N-dimethyl-acetamide hydrochloride

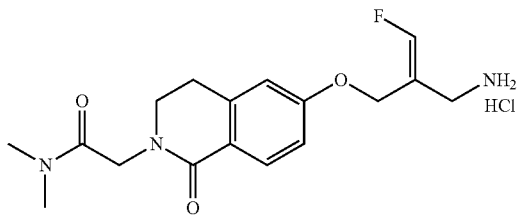

-continued

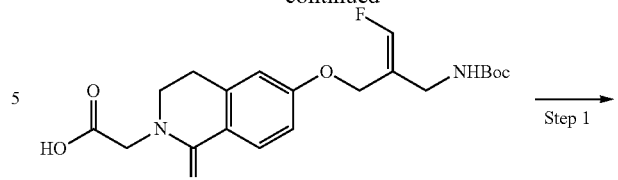

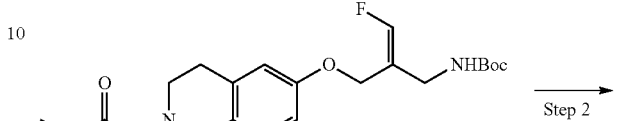

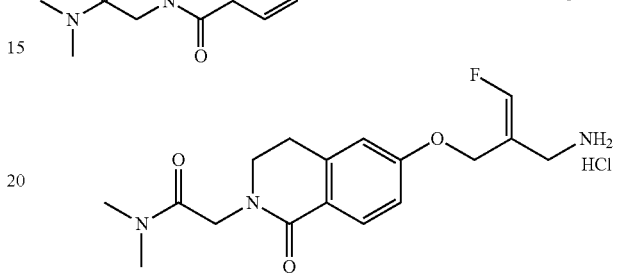

Step 1) Tert-butyl N—[(Z)-2-[[2-[2-(dimethyl-amino)-2-oxo-ethyl]-1-oxo-3,4-dihydroisoquinolin-6-yl] oxymethyl]-3-fluoro-allyl]carbamate 2-[6-[(Z)-2-[(tert-butyloxycarbonylamino)methyl]-3-fluoro-allyl oxy]-1-oxo-3,4-dihydroisoquinoline-2-yl]acetic acid (93 mg, 0.23 mmol) was dissolved in anhydrous tetrahydrofuran (6 mL), and then carbonyldiimidazole (97 mg, 0.59 mmol) was added, and the mixture was reacted at room temperature for 2 hours. To the mixture were added dimethylamine (0.1 mL, 2 mmol) and triethylamine (0.2 mL, 1 mmol) dropwise, the reaction was carried out at room temperature for 15 hours. Water (10 mL) was added to the reaction solution, and the mixture was extracted with ethyl acetate (30 mL×3). The combined organic phase was washed with water (30 mL×3) and saturated sodium chloride solution (10 mL×3) successively. The resulting product was dried with anhydrous sodium sulfate, then filtered and concentrated by suction. The obtained residue was purified by silica gel column chromatography [dichloromethane/methanol (v/v)=20/1] to obtain the title compound (91 mg, yield 92%) as a white solid.

MS (ESI, pos. ion) m/z: 458.1[M+Na]+.

Step 2) 2-[6-[(Z)-2-(aminomethyl)-3-fluoro-allyl oxy]-1-oxo-3,4-dihydroisoquinolin-2-yl]-N, N-dimethyl-acetamide hydrochloride Tert-Butyl N—[(Z)-2-[[2-[2-(dimethylamino)-2-oxo-ethyl]-1-oxo-3,4-dihydroisoquinolin-6-yl]oxymethyl]-3-fluoro-allyl]carbamate (117 mg, 0.27 mmol) was dissolved in ethyl acetate (1 mL), and then a solution of hydrogen chloride in ethyl acetate (6 mL, 3 mol/L) was added. The mixture was reacted at room temperature for 1 hour. The reaction solution was concentrated to obtain the title compound (96 mg, yield 96%, HPLC purity 91.86%) as a white solid.

MS (ESI, pos. ion) m/z: 336.1 [M−Cl]+;

$^1$H NMR (400 MHz, DMSO-$d_6$) δ (ppm) 8.35 (s, 3H), 7.78 (s, 1H), 7.32 (d, J=81.6 Hz, 1H), 6.91 (s, 2H), 4.70 (s, 2H), 4.32 (s, 2H), 4.02 (s, 2H), 3.41-3.25 (m, 4H), 2.98 (s, 3H), 2.82 (s, 3H).

Example 9 2-[6-[(E)-2-(aminomethyl)-3-fluoro-allyloxy]-1-oxo-3,4-dihydroisoquinolin-2-yl]-N-isopropyl-acetamide hydrochloride

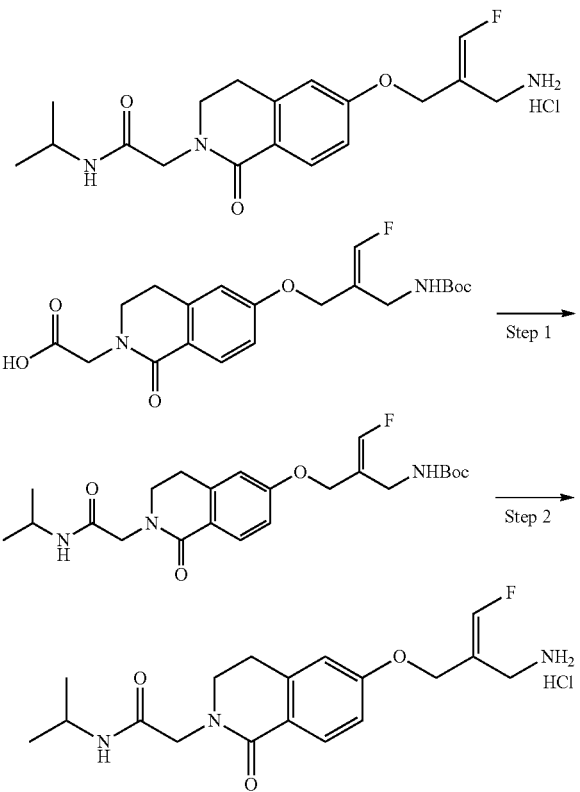

Step 1) Tert-butyl N-[(E)-3-fluoro-2-[[2-[2-(isopropylamino)-2-oxo-ethyl]-1-oxo-3,4-dihydroisoquinoline-6-yl]oxymethyl]allyl]carbamate 2-[6-[(E)-2-[(tert-butyloxycarbonylamino)methyl]-3-fluoro-allyloxy]-1-oxo-3,4-dihydroisoquinoline-2-yl]acetic acid (93 mg, 0.23 mmol) was dissolved in anhydrous tetrahydrofuran (6 mL), then carbonyldiimidazole (97 mg, 0.59 mmol) was added, and the mixture was stirred at room temperature for 2 hours. To the mixture were added isopropylamine (0.12 mL, 1.4 mmol) and triethylamine (0.2 mL, 1 mmol) dropwise. The resulting mixture was stirred at room temperature for 14 hours. Water (10 mL) was added to the reaction solution, and the solution was extracted with ethyl acetate (30 mL×3). The combined organic phase was washed with water (30 mL×3) and saturated sodium chloride solution (10 mL×3) successively. The resulting product was dried with anhydrous sodium sulfate, then filtered and concentrated by suction. The obtained residue was purified by silica gel column chromatography [dichloromethane/methanol (v/v)=20/1] to obtain the title compound (91 mg, yield 89%) as a white solid.

MS (ESI, pos. ion) m/z: 450.2 [M+H]$^+$.

Step 2) 2-[6-[(E)-2-(aminomethyl)-3-fluoro-allyloxy]-1-oxo-3,4-dihydroisoquinolin-2-yl]-N-isopropyl-acetamide hydrochloride Tert-Butyl N-[(E)-3-fluoro-2-[[2-[2-(isopropylamino)-2-oxo-ethyl]-1-oxo-3,4-dihydroisoquinoline-6-yl]oxymethyl] allyl]carbamate (91 mg, 0.20 mmol) was dissolved in ethyl acetate (1 mL), and then a solution of hydrogen chloride in ethyl acetate (6 mL, 3 mol/L) was added. The mixture was reacted at room temperature for 1 hour. The reaction solution was concentrated to obtain the title compound (78 mg, yield 99%, HPLC purity 97.41%) as a white solid.

MS (ESI, pos. ion) m/z: 350.1 [M−Cl]$^+$;

$^1$H NMR (400 MHz, DMSO-d$_6$) δ (ppm) 8.23 (s, 3H), 7.84 (dd, J=21.3, 8.0 Hz, 2H), 7.34 (d, J=81.8 Hz, 1H), 6.99-6.85 (m, 2H), 4.69 (s, 2H), 4.05 (s, 2H), 3.85 (td, J=13.5, 6.8 Hz, 1H), 3.61 (d, J=4.0 Hz, 2H), 3.55 (t, J=6.5 Hz, 2H), 2.96 (t, J=6.4 Hz, 2H), 1.06 (d, J=6.6 Hz, 6H).

Example 10 2-[6-[(Z)-2-(aminomethyl)-3-fluoro-allyloxy]-1-oxo-3,4-dihydroisoquinolin-2-yl]-N-isopropyl-acetamide hydrochloride

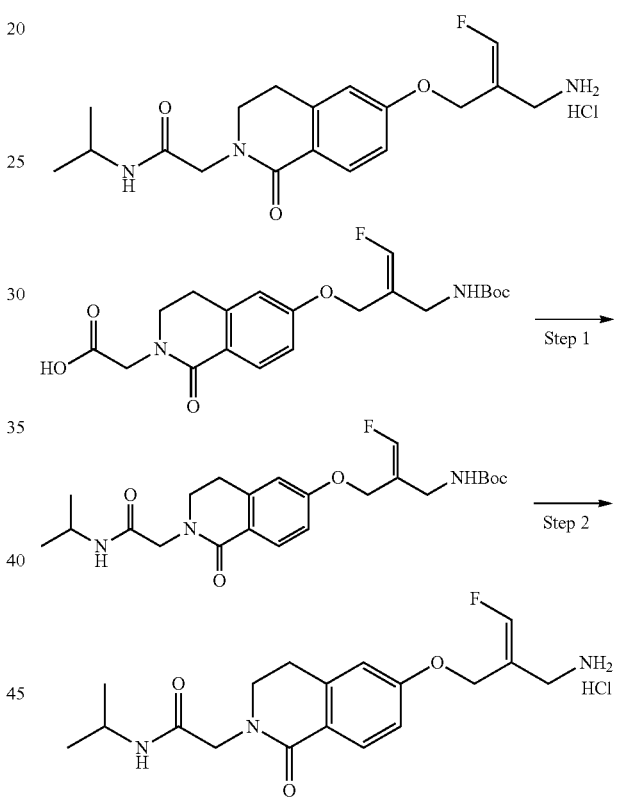

Step 1) Tert-butyl N—[(Z)-3-fluoro-2-[[2-[2-(isopropylamino)-2-oxo-ethyl]-1-oxo-3,4-dihydroisoquinoline-6-yl]oxymethyl]allyl]carbamate 2-[6-[(Z)-2-[(tert-butyloxycarbonylamino)methyl]-3-fluoro-allyloxy]-1-oxo-3,4-dihydroisoquinoline-2-yl]acetic acid (93 mg, 0.23 mmol) was dissolved in anhydrous tetrahydrofuran (6 mL), then carbonyldiimidazole (97 mg, 0.59 mmol) was added, and then the mixture was stirred at room temperature for 2 hours. To the mixture were added isopropylamine (0.12 mL, 1.4 mmol) and triethylamine (0.2 mL, 1 mmol) dropwise. The resulting mixture was stirred at room temperature for 14 hours. Water (10 mL) was added to the reaction solution, and the solution was extracted with ethyl acetate (30 mL×3). The combined organic phase was washed with water (30 mL×3) and saturated sodium chloride solution (10 mL×3) successively. The resulting product was dried with anhydrous sodium sulfate, then filtered and concentrated by suction. The obtained residue was purified by silica gel column chromatography [dichloromethane/methanol (v/v)=20/1] to obtain the title compound (102 mg, yield 99%) as a white solid.

MS (ESI, pos. ion) m/z: 450.2 [M+H]+

Step 2) 2-[6-[(Z)-2-(aminomethyl)-3-fluoro-allyloxy]-1-oxo-3,4-dihydroisoquinolin-2-yl]-N-isopropyl-acetamide hydrochloride Tert-Butyl N—[(Z)-3-fluoro-2-[[2-[2-(isopropylamino)-2-oxo-ethyl]-1-oxo-3,4-dihydroisoquinoline-6-yl]oxymethyl]allyl]carbamate (152 mg, 0.34 mmol) was dissolved in ethyl acetate (1 mL), and then a solution of hydrogen chloride in ethyl acetate (6 mL, 3 mol/L) was added. The mixture was reacted at room temperature for 1 hour. The reaction solution was concentrated to obtain the title compound (129 mg, yield 99%, HPLC purity 96.91%) as a white solid.

MS (ESI, pos. ion) m/z: 350.2 [M−Cl]+;

$^1$H NMR (400 MHz, DMSO-d$_6$) δ (ppm) 8.28 (s, 3H), 7.84 (d, J=21.9 Hz, 2H), 7.24 (d, J=82.9 Hz, 1H), 6.92 (s, 2H), 4.80 (s, 2H), 4.05 (s, 2H), 3.83 (s, 2H), 3.58 (s, 3H), 2.95 (s, 2H), 1.06 (s, 6H).

Example 11 2-[6-[(E)-2-(aminomethyl)-3-fluoroallyloxy]-1-oxo-3,4-dihydroisoquinolin-2-yl]-N-isobutyl-acetamide hydrochloride

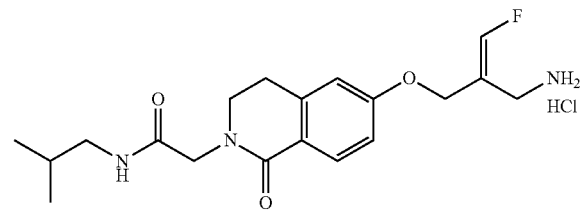

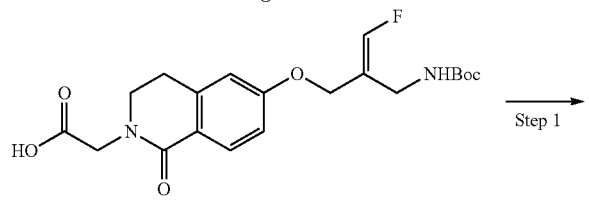

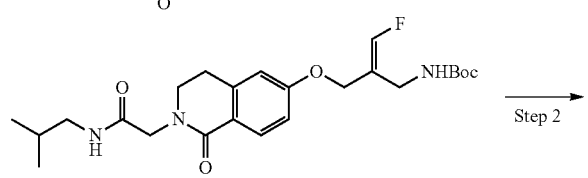

Step 1) Tert-butyl N-[(E)-3-fluoro-2-[[2-[2-(isobutylamino)-2-oxo-ethyl]-1-oxo-3,4-dihydroisoquinoline-6-yl]oxymethyl]allyl]carbamate 2-[6-[(E)-2-[(tert-butyloxycarbonylamino)methyl]-3-fluoro-allyloxy]-1-oxo-3,4-dihydroisoquinoline-2-yl]acetic acid (93 mg, 0.23 mmol) was dissolved in anhydrous tetrahydrofuran (6 mL), then carbonyldiimidazole (97 mg, 0.59 mmol) was added, and the mixture was stirred at room temperature for 2 hours. To the mixture were added isobutylamine (0.14 mL, 1.4 mmol) and triethylamine (0.2 mL, 1 mmol) dropwise. The resulting mixture was reacted at room temperature for 14 hours. Water (10 mL) was added to the reaction solution, and the solution was extracted with ethyl acetate (30 mL×3). The combined organic phase was washed with water (30 mL×3) and saturated sodium chloride solution (10 mL×3) successively. The resulting product was dried with anhydrous sodium sulfate, then filtered and concentrated by suction. The obtained residue was purified by silica gel column chromatography [dichloromethane/methanol (v/v)=20/1] to obtain the title compound (96 mg, yield 91%) as a white solid.

MS (ESI, pos. ion) m/z: 464.2 [M+H]+.

Step 2) 2-[6-[(E)-2-(aminomethyl)-3-fluoro-allyloxy]-1-oxo-3,4-dihydroisoquinolin-2-yl]-N-isobutyl-acetamide hydrochloride Tert-Butyl N-[(E)-3-fluoro-2-[[2-[2-(isobutylamino)-2-oxo-ethyl]-1-oxo-3,4-dihydroisoquinoline-6-yl]oxymethyl]allyl]carbamate (96 mg, 0.21 mmol) was dissolved in ethyl acetate (1 mL), and then a solution of hydrogen chloride in ethyl acetate (6 mL, 3 mol/L) was added. The mixture was reacted at room temperature for 1 hour. The reaction solution was concentrated to obtain the title compound (82 mg, yield 99%, HPLC purity 97.14%) as a white solid.

MS (ESI, pos. ion) m/z: 364.2 [M−Cl]+;

$^1$H NMR (400 MHz, DMSO-d$_6$) δ (ppm) 8.40 (s, 3H), 7.99 (t, J=5.5 Hz, 1H), 7.80 (d, J=8.5 Hz, 1H), 7.33 (d, J=81.9 Hz, 1H), 7.02-6.85 (m, 2H), 4.72 (s, 2H), 4.10 (s, 2H), 3.65-3.51 (m, 4H), 2.97 (t, J=6.2 Hz, 2H), 2.90 (t, J=6.2 Hz, 2H), 1.68 (td, J=13.3, 6.6 Hz, 1H), 0.84 (d, J=6.6 Hz, 6H).

Example 12 2-[6-[(Z)-2-(aminomethyl)-3-fluoro-allyloxy]-1-oxo-3,4-dihydroisoquinolin-2-yl]-N-isobutyl-acetamide hydrochloride

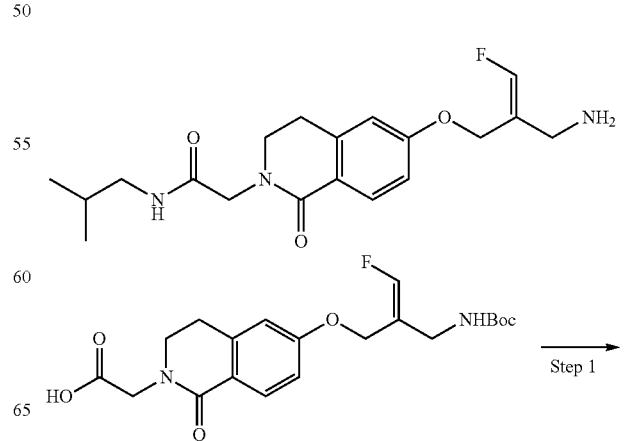

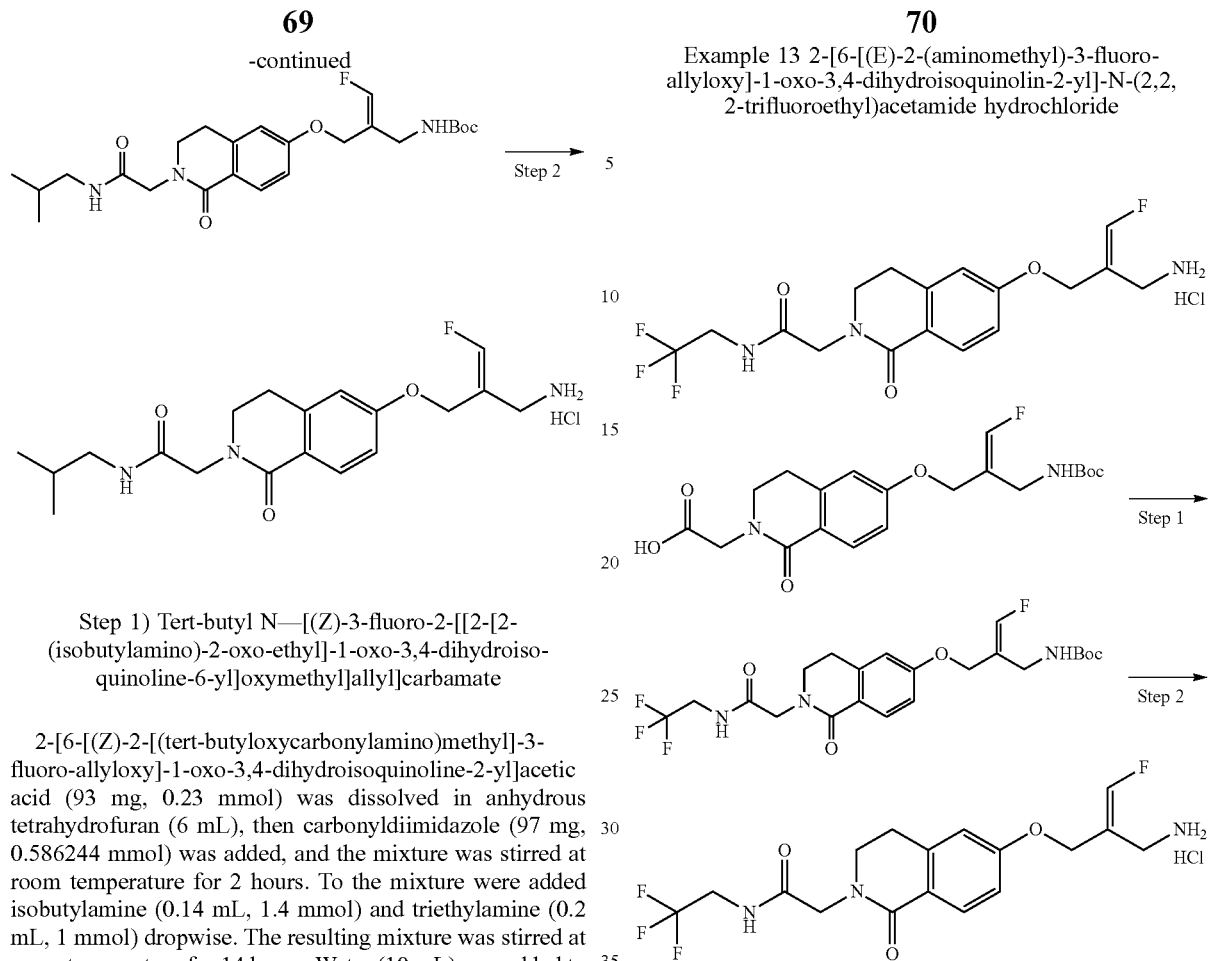

Example 13 2-[6-[(E)-2-(aminomethyl)-3-fluoro-allyloxy]-1-oxo-3,4-dihydroisoquinolin-2-yl]-N-(2,2,2-trifluoroethyl)acetamide hydrochloride

Step 1) Tert-butyl N—[(Z)-3-fluoro-2-[[2-[2-(isobutylamino)-2-oxo-ethyl]-1-oxo-3,4-dihydroiso-quinoline-6-yl]oxymethyl]allyl]carbamate 2-[6-[(Z)-2-[(tert-butyloxycarbonylamino)methyl]-3-fluoro-allyloxy]-1-oxo-3,4-dihydroisoquinoline-2-yl]acetic acid (93 mg, 0.23 mmol) was dissolved in anhydrous tetrahydrofuran (6 mL), then carbonyldiimidazole (97 mg, 0.586244 mmol) was added, and the mixture was stirred at room temperature for 2 hours. To the mixture were added isobutylamine (0.14 mL, 1.4 mmol) and triethylamine (0.2 mL, 1 mmol) dropwise. The resulting mixture was stirred at room temperature for 14 hours. Water (10 mL) was added to the reaction solution, and the solution was extracted with ethyl acetate (30 mL×3). The combined organic phase was washed with water (30 mL×3) and saturated sodium chloride solution (10 mL×3) successively. The resulting product was dried with anhydrous sodium sulfate, then filtered and concentrated by suction. The obtained residue was purified by silica gel column chromatography [dichloromethane/methanol (v/v)=20/1] to obtain the title compound (92 mg, yield 87%) as a white solid.

MS (ESI, pos. ion) m/z: 464.3 [M+H]+.

Step 2) 2-[6-[(Z)-2-(aminomethyl)-3-fluoro-ally-loxy]-1-oxo-3,4-dihydroisoquinolin-2-yl]-N-isobutyl-acetamide hydrochloride Tert-Butyl N—[(Z)-3-fluoro-2-[[2-[2-(isobutylamino)-2-oxo-ethyl]-1-oxo-3,4-dihydroisoquinoline-6-yl]oxymethyl]allyl]carbamate (132 mg, 0.28 mmol) was dissolved in ethyl acetate (1 mL), and then a solution of hydrogen chloride in ethyl acetate (6 mL, 3 mol/L) was added. The mixture was reacted at room temperature for 1 hour. The reaction solution was concentrated to obtain the title compound (113 mg, yield 99%, HPLC purity 97.09%) as a white solid. MS (ESI, pos. ion) m/z: 364.2 [M−Cl]+;

1H NMR (400 MHz, DMSO-d6) δ (ppm) 8.23 (s, 3H), 7.97 (s, 1H), 7.81 (d, J=8.5 Hz, 1H), 7.24 (d, J=82.1 Hz, 1H), 7.03-6.89 (m, 2H), 4.80 (s, 2H), 4.10 (s, 2H), 3.55 (d, J=6.3 Hz, 4H), 2.97 (d, J=5.6 Hz, 2H), 2.90 (t, J=6.0 Hz, 2H), 1.69 (dt, J=13.2, 6.6 Hz, 1H), 0.84 (d, J=6.6 Hz, 6H).

Step 1) Tert-butyl N-[(E)-3-fluoro-2-[[1-oxo-2-[2-oxo-2-(2,2,2-trifluoroethylamino)ethyl]-3,4-dihy-droisoquinolin-6-yl]oxymethyl]allyl]carbamate 2-[6-[(E)-2-[(tert-butyloxycarbonylamino)methyl]-3-fluoro-allyl oxy]-1-oxo-3,4-dihydroisoquinoline-2-yl]acetic acid (132 mg, 0.28 mmol) was dissolved in anhydrous tetrahydrofuran (6 mL), and then carbonyldiimidazole (97 mg, 0.59 mmol) was added, the mixture was stirred at room temperature for 2 hour. To the mixture were added 2,2,2-trifluoroethane amine hydrochloride (188 mg, 1.36 mmol) and triethylamine (0.4 mL, 3 mmol). The resulting mixture was stirred at room temperature for 16 hours. Water (10 mL) was added to the reaction solution, and the mixture was extracted with ethyl acetate (30 mL×3). The combined organic phase was washed with water (30 mL×3) and saturated sodium chloride solution (10 mL×3) successively. The resulting product was dried with anhydrous sodium sulfate, then filtered and concentrated by suction. The obtained residue was purified by silica gel column chromatography [dichloromethane/methanol (v/v)=20/1] to obtain the title compound (101 mg, yield 91%) as a white solid.

MS (ESI, pos. ion) m/z: 512.2[M+Na]+.

Step 2) 2-[6-[(E)-2-(aminomethyl)-3-fluoro-ally-loxy]-1-oxo-3,4-dihydroisoquinolin-2-yl]-N-(2,2,2-trifluoroethyl)acetamide hydrochloride Tert-Butyl N-[(E)-3-fluoro-2-[[1-oxo-2-[2-oxo-2-(2,2,2-trifluoroethylamino)ethyl]-3,4-dihydroisoquinolin-6-yl]

oxymethyl]allyl]carbamate (101 mg, 0.21 mmol) was dissolved in ethyl acetate (1 mL), and then a solution of hydrogen chloride in ethyl acetate (6 mL, 3 mol/L) was added. The mixture was reacted at room temperature for 1 hour. The reaction solution was concentrated to obtain the title compound (87 mg, yield 99%, HPLC purity 97.63%) as a white solid.

MS (ESI, pos. ion) m/z: 390.1 [M−Cl]$^+$;

$^1$H NMR (400 MHz, DMSO-d$_6$) δ (ppm) 8.70 (s, 1H), 8.20 (s, 3H), 7.81 (d, J=8.0 Hz, 1H), 7.23 (d, J=81.9 Hz, 1H), 7.04-6.85 (m, 2H), 4.79 (s, 2H), 4.19 (s, 2H), 4.03 (d, J=6.9 Hz, 2H), 3.92 (s, 2H), 3.57 (s, 2H), 2.97 (s, 2H).

Example 14 2-[6-[(Z)-2-(aminomethyl)-3-fluoro-allyloxy]-1-oxo-3,4-dihydroisoquinolin-2-yl]-N-(2,2,2-trifluoroethyl)acetamide hydrochloride

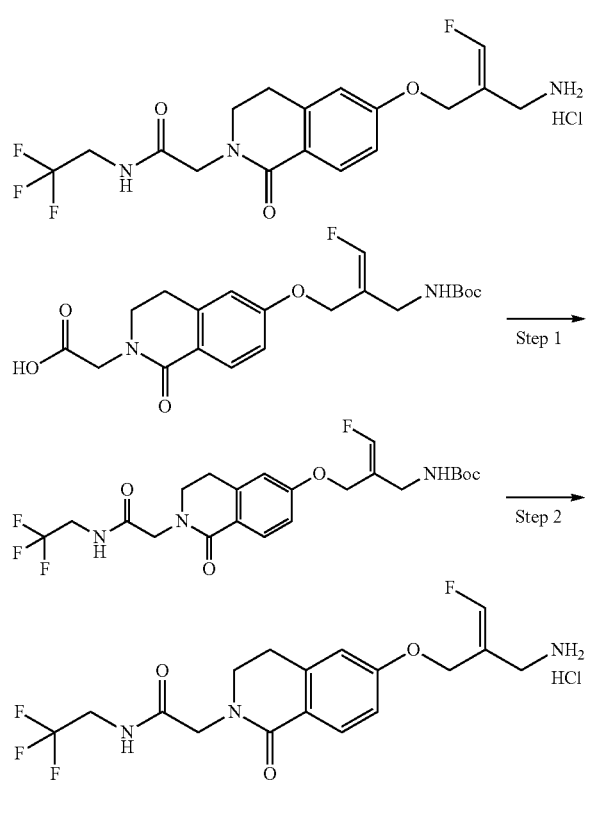

Step 1) Tert-butyl N—[(Z)-3-fluoro-2-[[1-oxo-2-[2-oxo-2-(2,2,2-trifluoroethylamino)ethyl]-3,4-dihydroisoquinolin-6-yl]oxymethyl]allyl]carbamate 2-[6-[(Z)-2-[(tert-butyloxycarbonylamino)methyl]-3-fluoro-allyl oxy]-1-oxo-3,4-dihydroisoquinoline-2-yl]acetic acid (93 mg, 0.23 mmol) was dissolved in anhydrous tetrahydrofuran (6 mL), and then carbonyldiimidazole (97 mg, 0.59 mmol) was added, the mixture was stirred at room temperature for 2 hour. To the mixture were added 2,2,2-trifluoroethane amine hydrochloride (188 mg, 1.36 mmol) and triethylamine (0.4 mL, 3 mmol). The resulting mixture was stirred at room temperature for 16 hours. Water (10 mL) was added to the reaction solution, and the mixture was extracted with ethyl acetate (30 mL×3). The combined organic phase was washed with water (30 mL×3) and saturated sodium chloride solution (10 mL×3) successively. The resulting product was dried with anhydrous sodium sulfate, then filtered and concentrated by suction. The obtained residue was purified by silica gel column chromatography [dichloromethane/methanol (v/v)=20/1] to obtain the title compound (96 mg, yield 86%) as a white solid.

MS (ESI, pos. ion) m/z: 512.1[M+Na]+.

Step 2) 2-[6-[(Z)-2-(aminomethyl)-3-fluoro-allyl oxy]-1-oxo-3,4-dihydroisoquinolin-2-yl]-N-(2,2,2-trifluoroethyl)acetamide hydrochloride Tert-Butyl N—[(Z)-3-fluoro-2-[[1-oxo-2-[2-oxo-2-(2,2,2-trifluoroethylamino)ethyl]-3,4-dihydroisoquinolin-6-yl]oxymethyl]allyl]carbamate (143 mg, 0.29 mmol) was dissolved in ethyl acetate (1 mL), and then a solution of hydrogen chloride in ethyl acetate (6 mL, 3 mol/L) was added. The mixture was reacted at room temperature for 1 hour. The reaction solution was concentrated to obtain the title compound (124 mg, yield 99%, HPLC purity 95.87%) as a white solid.

MS (ESI, pos. ion) m/z: 390.1 [M−Cl]$^+$;

$^1$H NMR (400 MHz, DMSO-d$_6$) δ (ppm) 8.70 (s, 1H), 8.20 (s, 3H), 7.81 (d, J=8.0 Hz, 1H), 7.23 (d, J=81.9 Hz, 1H), 7.04-6.85 (m, 2H), 4.79 (s, 2H), 4.19 (s, 2H), 4.03 (d, J=6.9 Hz, 2H), 3.92 (s, 2H), 3.57 (s, 2H), 2.97 (s, 2H).

Example 15 2-[6-[(E)-2-(aminomethyl)-3-fluoro-allyloxy]-1-oxo-3,4-dihydroisoquinolin-2-yl]-N-tert-butyl-acetamide hydrochloride

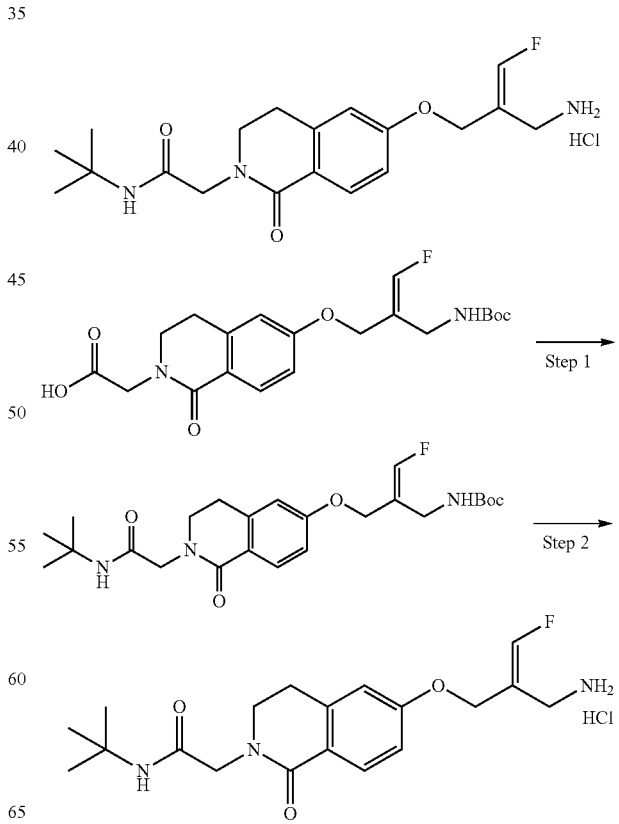

Step 1) Tert-butyl N-[(E)-2-[[2-[2-(2-tert-butylamino)-2-oxo-ethyl]-1-oxo-3,4-dihydroisoquinoline-6-yl]oxymethyl]-3-fluoro-allyl]carbamate 2-[6-[(E)-2-[(tert-butyloxycarbonylamino)methyl]-3-fluoro-allyloxy]-1-oxo-3,4-dihydroisoquinoline-2-yl]acetic acid (80 mg, 0.20 mmol) and 2-(7-azobenzotriazole)-N,N,N',N'-tetramethylurea hexafluorophosphate (90 mg, 0.23 mmol) were dissolved in dichloromethane (5 mL), then tert-butylamine (17 mg, 0.23) and triethylamine (0.031 mL, 0.22 mmol) were added to the solution, and the mixture was reacted at room temperature for 16 hours. The reaction was quenched by adding water (10 mL), extracted with dichloromethane (20 mL×3), the combined organic phase was washed with saturated sodium chloride solution (20 mL). The resulting product was dried with anhydrous sodium sulfate, then filtered and concentrated by suction. The obtained residue was purified by silica gel column chromatography [100% ethyl acetate] to obtain the title compound (91 mg, yield 99%) as a colorless oil.

Step 2) 2-[6-[(E)-2-(aminomethyl)-3-fluoro-allyloxy]-1-oxo-3,4-dihydroisoquinolin-2-yl]-N-tert-butyl-acetamide hydrochloride Tert-Butyl N-[(E)-2-[[2-[2-(2-tert-butylamino)-2-oxo-ethyl]-1-oxo-3,4-dihydroisoquinoline-6-yl]oxymethyl]-3-fluoro-allyl]carbamate (91 mg, 0.20 mmol) was dissolved in ethyl acetate (0.5 mL), and then a solution of hydrogen chloride in ethyl acetate (2 mL, 3.0 mol/L) was added. The mixture was reacted at room temperature for 1 hour. The reaction solution was concentrated to obtain the title compound (79 mg, yield 99%, HPLC purity 83.39%) as a white solid.

MS (ESI, pos. ion) m/z: 364.6 [M−Cl]$^+$;

$^1$H NMR (400 MHz, DMSO-d$_6$) δ (ppm) 8.22 (s, 3H), 7.81 (d, J=8.4 Hz, 1H), 7.59 (s, 1H), 7.34 (d, J=81.8 Hz, 1H), 6.95 (d, J=8.2 Hz, 1H), 6.91 (s, 1H), 4.68 (s, 2H), 4.04 (s, 2H), 3.62 (s, 2H), 2.95 (s, 2H), 2.69 (s, 2H), 1.26 (s, 9H).

Example 16 2-[6-[(E)-2-(aminomethyl)-3-fluoro-allyloxy]-1-oxo-3,4-dihydroisoquinolin-2-yl]-N-cyclopropyl-acetamide hydrochloride

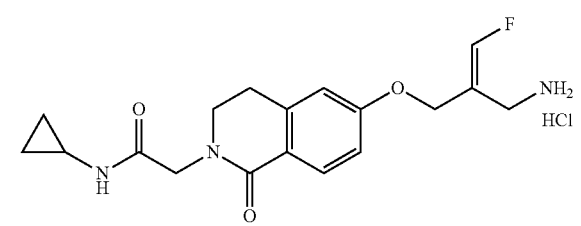

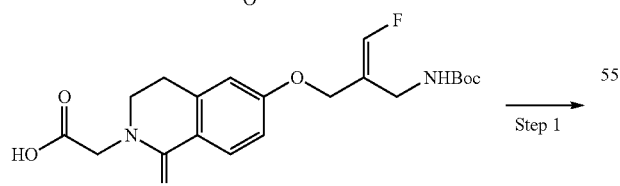
Step 1

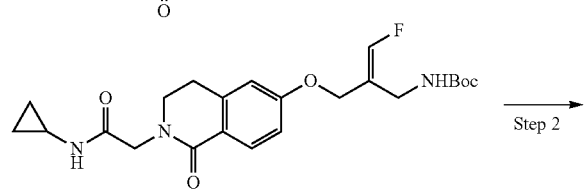
Step 2

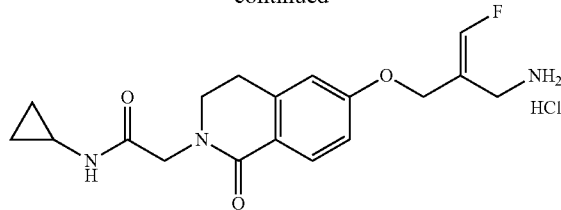

Step 1) Tert-butyl N-[(E)-2-[[2-[2-(cyclopropylamino)-2-oxo-ethyl]-1-oxo-3,4-dihydroisoquinolin-6-yl]oxymethyl]-3-fluoro-allyl]carbamate 2-[6-[(E)-2-[(tert-butyloxycarbonylamino)methyl]-3-fluoro-allyloxy]-1-oxo-3,4-dihydroisoquinoline-2-yl]acetic acid (50 mg, 0.12 mmol) was dissolved in N,N'-dimethylformamide (3 mL), N,N'-carbonyldiimidazole (50 mg, 0.31 mmol) was added to the solution, and the mixture was reacted for 3 hours. To the mixture were added cyclopropylamine (42 mg, 0.74 mmol) and triethylamine (0.11 mL, 0.79 mmol). The resulting mixture was reacted at room temperature for 17 hours. The reaction was quenched by adding water (10 mL), extracted with ethyl acetate (20 mL×3), and the combined organic phase was washed with saturated sodium chloride solution (20 mL). The resulting product was dried with anhydrous sodium sulfate, then filtered and concentrated by suction. The obtained residue was purified by silica gel column chromatography [ethyl acetate/petroleum ether (v/v)=3/1] to obtain the title compound (45 mg, yield 82%) as a white solid.

MS (ESI, pos. ion) m/z: 392.1 [M−55]$^+$;

Step 2) 2-[6-[(E)-2-(aminomethyl)-3-fluoro-allyloxy]-1-oxo-3,4-dihydroisoquinolin-2-yl]-N-cyclopropyl-acetamide hydrochloride A solution of hydrogen chloride in ethyl acetate (3 mL, 3.0 mol/L) was added into tert-butyl N-[(E)-2-[[2-[2-(cyclopropylamino)-2-oxo-ethyl]-1-oxo-3,4-dihydroisoquinolin-6-yl]oxymethyl]-3-fluoro-allyl]carbamate (45 mg, 0.12 mmol), the mixture was reacted at room temperature for 25 minutes. The reaction solution was concentrated to obtain the title compound (38 mg, yield 98%, HPLC purity 94.55%) as a pale yellow solid.

MS (ESI, pos. ion) m/z: 348.2 [M−Cl]$^+$;

$^1$H NMR (400 MHz, DMSO-d$_6$) δ (ppm) 8.29 (s, 3H), 8.09 (d, J=3.8 Hz, 1H), 7.80 (d, J=8.6 Hz, 1H), 7.34 (d, J=81.9 Hz, 1H), 6.95 (dd, J=15.1, 6.5 Hz, 2H), 4.70 (s, 2H), 4.04 (s, 2H), 3.60 (s, 2H), 3.56 (t, J=6.5 Hz, 2H), 2.96 (t, J=6.4 Hz, 2H), 2.63 (td, J=7.1, 3.6 Hz, 1H), 0.61 (q, J=6.7 Hz, 2H), 0.46-0.36 (m, 2H).

Example 17 2-[6-[(E)-2-(aminomethyl)-3-fluoro-allyloxy]-1-oxo-3,4-dihydroisoquinolin-2-yl]-N-cyclobutyl-acetamide hydrochloride

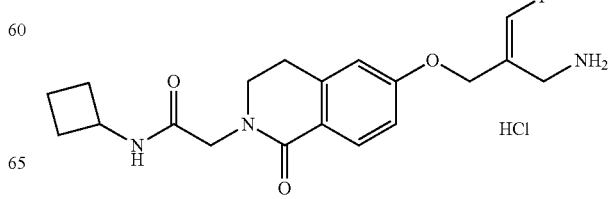

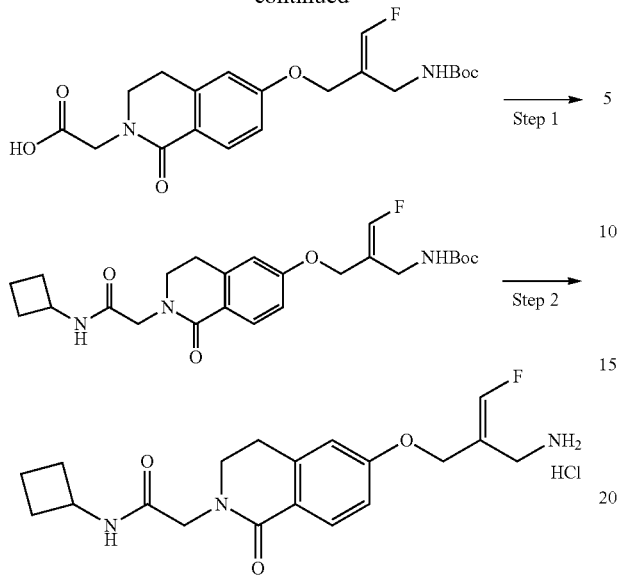

Step 1) Tert-butyl N-[(E)-2-[[2-[2-(cyclobutylamino)-2-oxo-ethyl]-1-oxo-3,4-dihydroisoquinolin-6-yl]oxymethyl]-3-fluoro-allyl]carbamate 2-[6-[(E)-2-[(tert-butyloxycarbonylamino)methyl]-3-fluoro-allyloxy]-1-oxo-3,4-dihydroisoquinoline-2-yl]acetic acid (50 mg, 0.12 mmol) was dissolved in N,N'-dimethylformamide (3 mL), and then N,N-carbonyldiimidazole (50 mg, 0.31 mmol) was added to the solution, the mixture was reacted for 3 hours. To the mixture were added cyclobutylamine (53 mg, 0.73 mmol) and triethylamine (0.11 mL, 0.79 mmol), the mixture was reacted at room temperature for 17 hours. The reaction was quenched by adding water (10 mL), extracted with ethyl acetate (20 mL×3), and the combined organic phase was washed with saturated sodium chloride solution (20 mL). The resulting product was dried with anhydrous sodium sulfate, then filtered and concentrated by suction. The obtained residue was purified by silica gel column chromatography [ethyl acetate/petroleum ether (v/v)=3/1] to obtain the title compound (55 mg, yield 97%) as a white solid.

MS (ESI, pos. ion) m/z: 406.1 [M−55]+.

Step 2) 2-[6-[(E)-2-(aminomethyl)-3-fluoro-allyloxy]-1-oxo-3,4-dihydroisoquinolin-2-yl]-N-cyclobutyl-acetamide hydrochloride A solution of hydrogen chloride in ethyl acetate (3 mL, 3.0 mol/L) was added into tert-butyl N-[(E)-2-[[2-[2-(cyclobutylamino)-2-oxo-ethyl]-1-oxo-3,4-dihydroisoquinolin-6-yl]oxymethyl]-3-fluoro-allyl]carbamate (55 mg, 0.12 mmol), the mixture was reacted at room temperature for 30 minutes. The reaction solution was concentrated to obtain the title compound (47 mg, yield 99%, HPLC purity 94.23%) as a white solid.

MS (ESI, pos. ion) m/z: 362.2 [M−Cl]+;
1H NMR (400 MHz, DMSO-d6) δ (ppm) 8.43-8.18 (m, 4H), 7.80 (d, J=8.6 Hz, 1H), 7.33 (d, J=81.9 Hz, 1H), 7.01-6.87 (m, 2H), 4.70 (d, J=2.5 Hz, 2H), 4.27-4.12 (m, 1H), 4.05 (s, 2H), 3.60 (s, 2H), 3.55 (t, J=6.5 Hz, 2H), 2.95 (t, J=6.4 Hz, 2H), 2.20-2.06 (m, 2H), 1.98-1.84 (m, 2H), 1.67-1.52 (m, 2H).

Example 18 2-[6-[(E)-2-(aminomethyl)-3-fluoro-allyloxy]-1-oxo-3,4-dihydroisoquinolin-2-yl]-N-(2-methanesulfonylethyl)acetamide hydrochloride

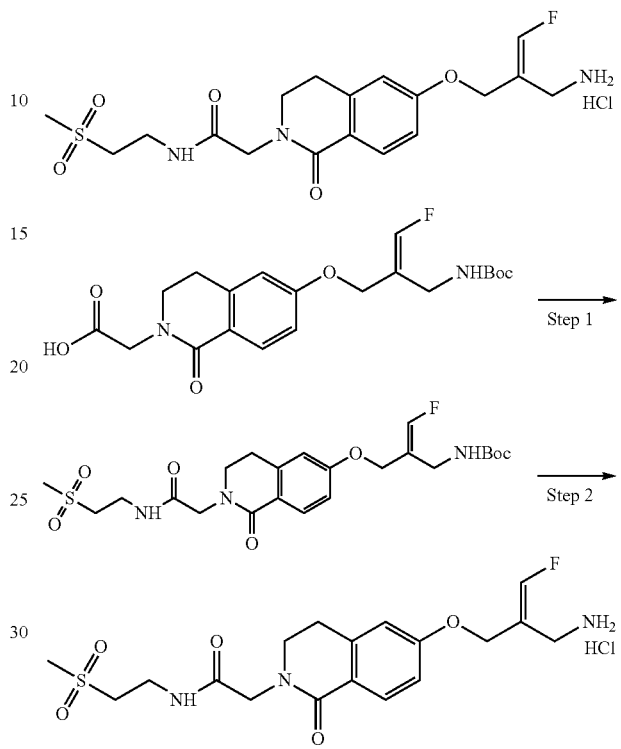

Step 1) Tert-butyl N-[(E)-3-Fluoro-2-[[2-[2-(2-methanesulfonylethylamino)-2-oxo-ethyl]-1-oxo-3,4-dihydroisoquinolin-6-yl]oxymethyl]allyl]carbamate 2-[6-[(E)-2-[(tert-butyloxycarbonylamino)methyl]-3-fluoro-allyloxy]-1-oxo-3,4-dihydroisoquinoline-2-yl]acetic acid (80 mg, 0.20 mmol) and 2-(7-azobenzotriazole)-N,N,N',N'-tetramethylurea hexafluorophosphate (90 mg, 0.23 mmol) were dissolved in dichloromethane (5 mL), then 2-(methylsulfone)ethylamine hydrochloride (38 mg, 0.24 mmol) and triethylamine (0.061 mL, 0.43 mmol) were added to the mixture, and the mixture was reacted at room temperature for 16 hours. The reaction was quenched by adding water (10 mL), extracted with dichloromethane (20 mL×3), and the combined organic phase was washed with saturated sodium chloride solution (20 mL). The resulting product was dried over anhydrous sodium sulfate, then filtered and concentrated by suction. The obtained residue was purified by silica gel column chromatography [100% ethyl acetate] to obtain the title compound (81 mg, yield 81%) as a white solid.

MS (ESI, pos. ion) m/z: 458.3 [M−55]+.

Step 2) 2-[6-[(E)-2-(aminomethyl)-3-fluoro-allyloxy]-1-oxo-3,4-dihydroisoquinolin-2-yl]-N-(2-methanesulfonylethyl)acetamide hydrochloride Tert-Butyl N-[(E)-3-Fluoro-2-[[2-[2-(2-methanesulfonylethylamino)-2-oxo-ethyl]-1-oxo-3,4-dihydroisoquinolin-6- yl]oxymethyl]allyl]carbamate (81 mg, 0.16 mmol) was dissolved in dichloromethane (0.5 mL), and a solution of hydrogen chloride in ethyl acetate (2 mL, 3.0 mol/L) was added, the mixture was reacted at room temperature for 1 hour. The reaction solution was concentrated to obtain the title compound (70 mg, yield 99%, HPLC purity 91.04%) as a pale yellow solid.

MS (ESI, pos. ion) m/z: 414.1 [M−Cl]$^+$;

1H NMR (400 MHz, DMSO-$d_6$) δ (ppm) 8.36 (s, 3H), 8.28 (s, 1H), 7.81 (d, J=8.2 Hz, 1H), 7.33 (d, J=81.9 Hz, 1H), 7.02-6.87 (m, 2H), 4.71 (s, 2H), 4.09 (s, 2H), 3.69-3.61 (m, 4H), 3.49 (d, J=5.6 Hz, 2H), 3.27 (d, J=5.9 Hz, 2H), 3.00 (d, J=11.5 Hz, 5H).

Example 19 2-[6-[(E)-2-(aminomethyl)-3-fluoro-allyloxy]-1-oxo-3,4-dihydroisoquinolin-2-yl]-N-(3, 3-difluorocyclobutyl)-acetamide hydrochloride

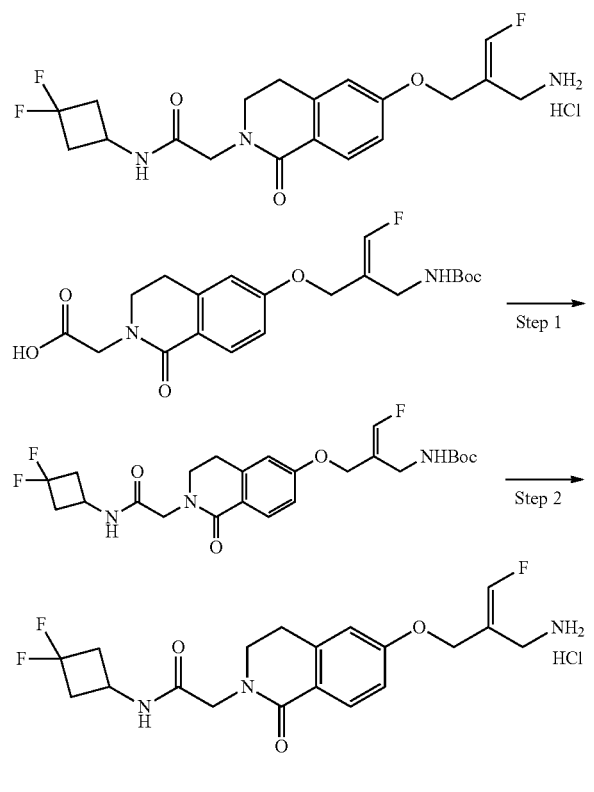

Step 1) Tert-butyl N-[(E)-2-[[2-[2-(3,3-difluorocyclobutyl)amino]-2-oxo-ethyl]-1-oxo-3,4-dihydro isoquinolin-6-yl]oxymethyl]-3-fluoro-allyl]carbamate 2-[6-[(E)-2-[(tert-butyloxycarbonylamino)methyl]-3-fluoro-allyl oxy]-1-oxo-3,4-dihydroisoquinoline-2-yl]acetic acid (50 mg, 0.12 mmol) and N,N'-carbonyldiimidazole (50 mg, 0.31 mmol) were dissolved in N,N'-dimethylformamide (3 mL), and then N,N'-carbonyl diimidazole (50 mg, 0.31 mmol) was added. The mixture was reacted at room temperature for 3 hours, then 3,3-difluorocyclobutylamine (105 mg, 0.73 mmol) and triethylamine (0.11 mL, 0.79 mmol) were added, the mixture was reacted at room temperature for 19 hours. The reaction was quenched by adding water (10 mL), extracted with dichloromethane (20 mL×3), and the combined organic phase was washed with saturated sodium chloride solution (20 mL). The resulting product was dried over anhydrous sodium sulfate, then filtered and concentrated by suction. The obtained residue was purified by silica gel column chromatography [ethyl acetate/petroleum ether (v/v)=2/1] to obtain the title compound (60 mg, yield 98%) as a white solid.

MS (ESI, pos. ion) m/z: 442.1 [M−55]$^+$.

Step 2) 2-[6-[(E)-2-(aminomethyl)-3-fluoro-allyloxy]-1-oxo-3,4-dihydroisoquinolin-2-yl]-N-(3,3-difluorocyclobutyl)-acetamide hydrochloride A solution of hydrogen chloride in ethyl acetate (2 mL, 3.0 mol/L) was added into tert-butyl N-[(E)-2-[[2-[2-(3,3-difluorocyclobutyl)amino]-2-oxo-ethyl]-1-oxo-3,4-dihydroisoquinolin-6-yl]oxymethyl]-3-fluoro-allyl]carbamate (60 mg, 0.12 mmol), the mixture was reacted at room temperature for 15 minutes. The reaction solution was concentrated to obtain the title compound (51 mg, yield 97%, HPLC purity 93.11%) as a white sticky substance.

MS (ESI, pos. ion) m/z: 398.1 [M−Cl]$^+$;

$^1$H NMR (400 MHz, DMSO-$d_6$) δ (ppm) 8.53 (d, J=6.7 Hz, 1H), 8.32 (s, 3H), 7.81 (d, J=8.6 Hz, 1H), 7.33 (d, J=81.9 Hz, 1H), 7.01-6.86 (m, 2H), 4.70 (d, J=2.6 Hz, 2H), 4.11-4.00 (m, 3H), 3.57 (dd, J=13.4, 6.7 Hz, 4H), 2.97 (t, J=6.4 Hz, 2H), 2.88 (dd, J=18.2, 9.5 Hz, 2H), 2.68-2.54 (m, 2H).

Example 20 6-[(E)-2-(aminomethyl)-3-fluoro-allyloxy]-2-(2-oxo-2-pyrrolidin-1-yl-ethyl)-3,4-dihydroisoquinoline-1-one hydrochloride

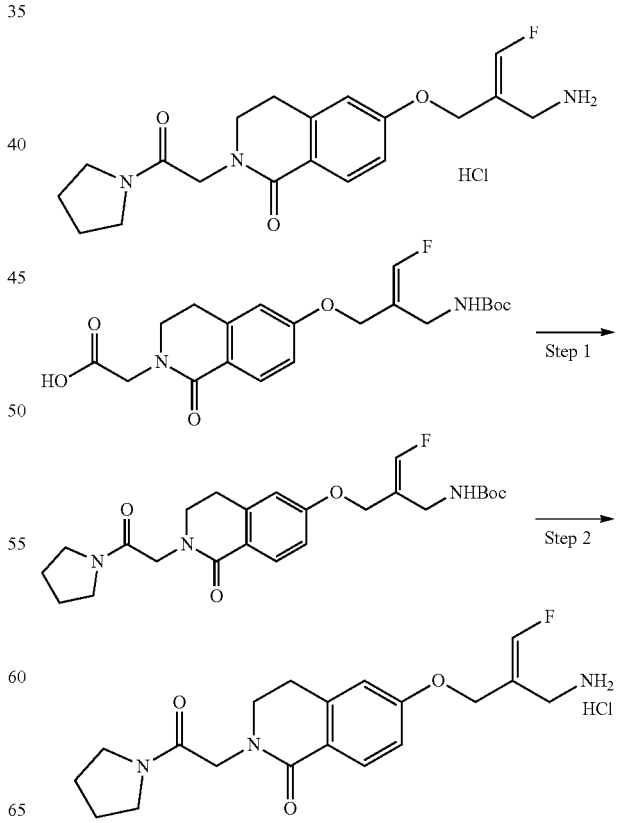

Step 1) Tert-butyl N-[(E)-3-fluoro-2-[[1-oxo-2-(2-oxo-2-pyrrolidin-1-yl-ethyl)-3,4-dihydroisoquinolin-6-yl]oxymethyl]-3-fluoro-allyl]carbamate 2-[6-[(E)-2-[(tert-butyloxycarbonylamino)methyl]-3-fluoro-allyloxy]-1-oxo-3,4-dihydroisoquinolin e-2-yl]acetic acid (50 mg, 0.12 mmol) was dissolved in N,N'-dimethyl-formamide (3 mL), and then N,N'-carbonyldiimidazole (50 mg, 0.31 mmol) was added. The mixture was stirred for 3 hours, then tetrahydropyrrole (52 mg, 0.73 mmol) and triethylamine (0.11 mL, 0.79 mmol) were added to the solution. The mixture was reacted at room temperature for 19 hours. The reaction was quenched by adding water (10 mL), extracted with dichloromethane (20 mL×3), and the combined organic phase was washed with saturated sodium chloride solution (20 mL). The resulting product was dried over anhydrous sodium sulfate, then filtered and concentrated by suction. The obtained residue was purified by silica gel column chromatography [ethyl acetate/petroleum ether (v/v)=2/1] to obtain the title compound (43 mg, yield 76%) as a white solid.

MS (ESI, pos. ion) m/z: 462.2 [M+H]$^+$;

Step 2) 6-[(E)-2-(aminomethyl)-3-fluoro-allyloxy]-2-(2-oxo-2-pyrrolidin-1-yl-ethyl)-3,4-dihydroisoquinolin-1-one hydrochloride A solution of hydrogen chloride in ethyl acetate (2 mL, 3.0 mol/L) was added into tert-butyl N-[(E)-3-fluoro-2-[[1-oxo-2-(2-oxo-2-pyrrolidin-1-yl-ethyl)-3,4-dihydroisoquinoline-6-yl]oxymethyl]-3-fluoro-allyl]carbamate (43 mg, 0.09 mmol), the mixture was reacted at room temperature for 15 minutes. The reaction solution was concentrated to obtain the title compound (37 mg, yield 100%, HPLC purity 92.29%) as a white solid.

MS (ESI, pos. ion) m/z: 362.2 [M−Cl]$^+$;

$^1$H NMR (400 MHz, DMSO-d$_6$) δ (ppm) 8.27 (s, 3H), 7.80 (d, J=8.6 Hz, 1H), 7.34 (d, J=81.9 Hz, 1H), 7.00-6.84 (m, 2H), 4.70 (d, J=2.7 Hz, 2H), 4.26 (s, 2H), 3.63-3.54 (m, 4H), 3.48-3.41 (m, 2H), 3.30 (t, J=6.8 Hz, 2H), 2.96 (t, J=6.4 Hz, 2H), 1.95-1.88 (m, 2H), 1.81-1.74 (m, 2H).

Example 21 2-[6-[(E)-2-(aminomethyl)-3-fluoro-allyloxy]-1-oxo-3,4-dihydroisoquinolin-2-yl]-N-propyl-acetamide hydrochloride

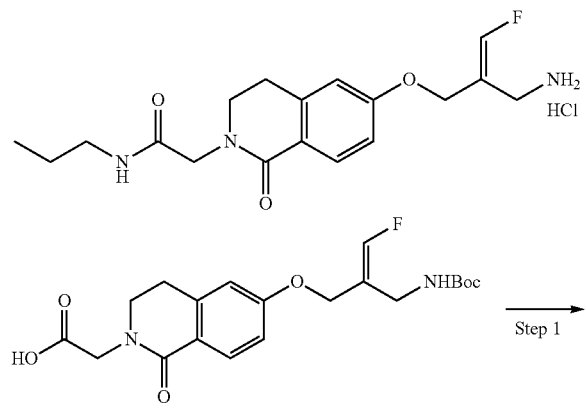

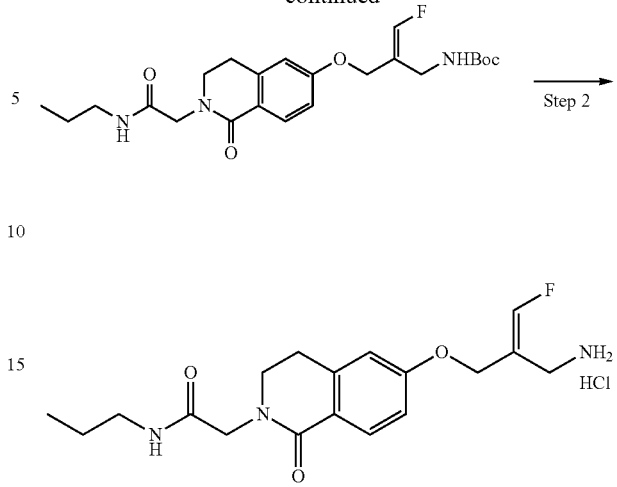

Step 1) Tert-butyl N-[(E)-3-fluoro-2-[[1-oxo-2-[2-oxo-2-(propylamine)ethyl]-3,4-dihydroisoquinolin-6-yl]oxymethyl]-3-fluoro-allyl]carbamate 2-[6-[(E)-2-[(tert-butyloxycarbonylamino)methyl]-3-fluoro-allyloxy]-1-oxo-3,4-dihydroisoquinoline-2-yl]acetic acid (50 mg, 0.12 mmol) was dissolved in N,N'-dimethyl-formamide (3 mL), then N,N'-carbonyldiimidazole (50 mg, 0.31 mmol) was added and the mixture was reacted for 3 hours. Propylamine (43 mg, 0.73 mmol) and triethylamine (0.11 mL, 0.79 mmol) were added, and the mixture was reacted at room temperature for 19 hours. The reaction was quenched by adding water (10 mL), extracted with ethyl acetate (20 mL×3), and the combined organic phase was washed with saturated sodium chloride solution (20 mL). The resulting product was dried over anhydrous sodium sulfate, then filtered and concentrated by suction. The obtained residue was purified by silica gel column chromatography [ethyl acetate/petroleum ether (v/v)=2/1] to obtain the title compound (55 mg, yield 100%) as a white solid.

MS (ESI, pos. ion) m/z: 394.1 [M−55]$^+$.

Step 2) 2-[6-[(E)-2-(aminomethyl)-3-fluoro-allyloxy]-1-oxo-3,4-dihydroisoquinolin-2-yl]-N-propyl-acetamide hydrochloride A solution of hydrogen chloride in ethyl acetate (2 mL, 3.0 mol/L) was added into tert-butyl N-[(E)-3-fluoro-2-[[1-oxo-2-[2-oxo-2-(propylamine)ethyl]-3,4-dihydroisoquinolin-6-yl]oxymethyl]-3-fluoro-allyl]carbamate (55 mg, 0.12 mmol), the mixture was reacted at room temperature for 15 minutes. The reaction solution was concentrated to obtain the title compound (45 mg, yield 95%, HPLC purity 91.28%) as a white solid.

MS (ESI, pos. ion) m/z: 350.1 [M−Cl]$^+$;

$^1$H NMR (400 MHz, DMSO-d$_6$) δ (ppm) 8.29 (s, 3H), 7.97 (d, J=5.9 Hz, 1H), 7.81 (d, J=8.6 Hz, 1H), 7.34 (d, J=81.9 Hz, 1H), 6.95 (dd, J=15.1, 6.5 Hz, 2H), 4.70 (d, J=2.6 Hz, 2H), 4.08 (s, 2H), 3.63-3.54 (m, 4H), 3.03 (d, J=6.4 Hz, 2H), 2.97 (t, J=6.4 Hz, 2H), 1.42 (dd, J=7.2, 2.6 Hz, 2H), 0.85 (s, 3H).

Example 22 2-[6-[(E)-2-(aminomethyl)-3-fluoro-allyloxy]-1-oxo-3,4-dihydroisoquinolin-2-yl]-N-(2-methoxyethyl)acetamide hydrochloride

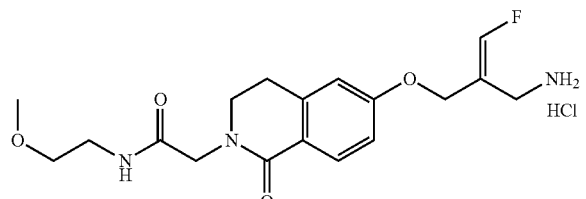

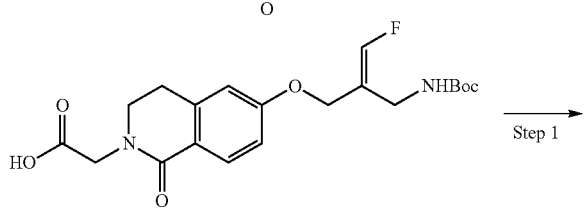

Step 1

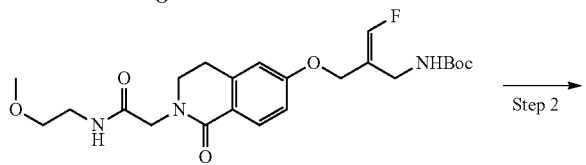

Step 2

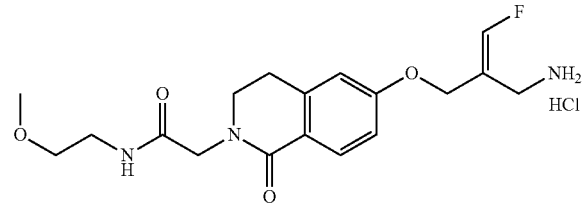

Step 1) Tert-butyl N-[(E)-3-fluoro-2-[[2-[2-(2-methoxy ethyl amino)-2-oxo-ethyl]-1-oxo-3,4-dihydroisoquinolin-6-yl]oxymethyl]allyl]carbamate 2-[6-[(E)-2-[(tert-butyloxycarbonylamino)methyl]-3-fluoro-allyloxy]-1-oxo-3,4-dihydroisoquinoline-2-yl]acetic acid (40 mg, 0.10 mmol) was dissolved in N,N'-dimethylformamide (3 mL), then N,N'-carbonyldiimidazole (41 mg, 0.25 mmol) was added to the solution, and the mixture was reacted for 3 hours. To the resulting mixture were added 2-methoxyethylamine (45 mg, 0.59 mmol) and triethylamine (0.08 mL, 0.59 mmol), and the mixture was reacted at room temperature for 15 hours. The reaction was quenched by adding water (10 mL), extracted with ethyl acetate (20 mL×3), and the combined organic phase was washed with saturated sodium chloride solution (20 mL). The resulting product was dried over anhydrous sodium sulfate, then filtered and concentrated by suction. The obtained residue was purified by silica gel column chromatography [ethyl acetate/petroleum ether (v/v)=2/1] to obtain the title compound (29 mg, yield 63%) as a colorless sticky substance.
MS (ESI, pos. ion) m/z: 466.2 [M+H]$^+$.

Step 2) 2-[6-[(E)-2-(aminomethyl)-3-fluoro-allyloxy]-1-oxo-3,4-dihydroisoquinolin-2-yl]-N-(2-methoxyethyl)acetamide hydrochloride A solution of hydrogen chloride in ethyl acetate (3 mL, 3.0 mol/L) was added into tert-butyl N-[(E)-3-fluoro-2-[[2-[2-(2-methoxyethylamino)-2-oxo-ethyl]-1-oxo-3,4-dihydroisoquinolin-6-yl]oxymethyl]allyl]carbamate (29 mg, 0.06 mmol), the mixture was reacted at room temperature for 15 minutes. The reaction solution was concentrated to obtain the title compound (25 mg, yield 100%, HPLC purity 96.52%) as a colorless sticky substance.
MS (ESI, pos. ion) m/z: 366.2 [M−Cl]$^+$;
$^1$H NMR (400 MHz, DMSO-d$_6$) δ (ppm) 8.27 (s, 3H), 8.06 (t, J=5.4 Hz, 1H), 7.81 (d, J=8.6 Hz, 1H), 7.34 (d, J=81.9 Hz, 1H), 7.00-6.88 (m, 2H), 4.69 (d, J=2.6 Hz, 2H), 4.09 (s, 2H), 3.61 (s, 2H), 3.55 (t, J=6.5 Hz, 2H), 3.34 (d, J=5.7 Hz, 2H), 3.26-3.21 (m, 5H), 2.97 (t, J=6.4 Hz, 2H).

Example 23 [6-[(E)-2-(aminomethyl)-3-fluoro-allyloxy]-1-oxo-3,4-dihydroisoquinolin-2-yl]-methylphosphonic acid hydrochloride

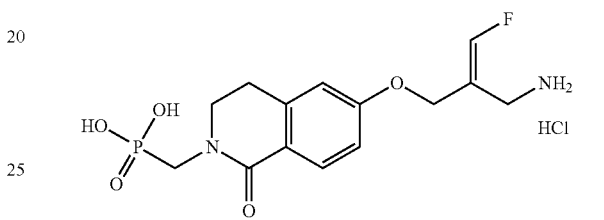

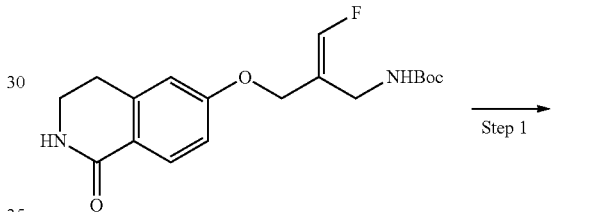

Step 1

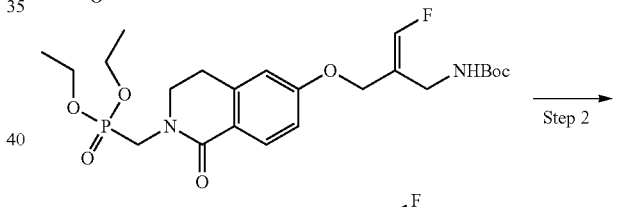

Step 2

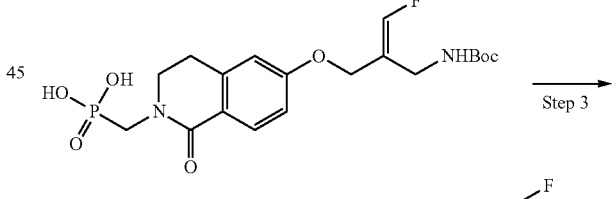

Step 3

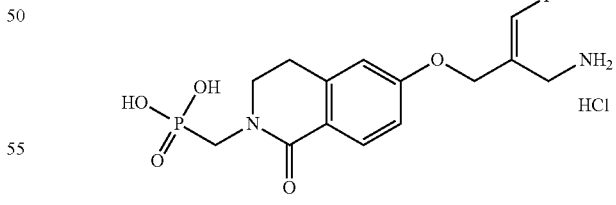

Step 1) Tert-butyl N-[(E)-2-[[2-(diethoxyphosphorylmethyl)-1-oxo-3,4-dihydroisoquinolin-6-yl]oxymethyl]-3-fluoro-allyl] carbamate At 0° C., sodium hydride (46 mg, 1.15 mmol, 60% wt) was added into anhydrous tetrahydrofuran (5 mL), then tert-butyl N-[(E)-3-fluoro-2-[(1-keto-3,4dihydro-2H-isoquinoline-6-oxy)oxymethyl]allyl]carbamate (0.20 g, 0.57 mmol) was added, the mixture was reacted at room temperature for 10 minutes. To the resulting mixture was added (chloromethyl) diethyl phosphonate (0.55 mL, 2.9 mmol) dropwise, the mixture was reacted at room temperature for 16 hours. The reaction was quenched by adding water (10 mL) and extracted with ethyl acetate (20 mL×2). The combined organic phase was dried over anhydrous sodium sulfate, then filtered and concentrated by suction. The residue was purified by silica gel column chromatography [petroleum ether/ethyl acetate (v/v)=1/1] to obtain the title compound (0.19 g, yield 67%) as a colorless oil.

Step 2) [6-[(E)-2-[(tert-butoxycarbonylamino) methyl]-3-fluoro-allyl oxy]-1-oxo-3,4-dihydroisoquinolin-2-yl]-methylphosphonic acid Tert-Butyl N-[(E)-2-[[2-(diethoxyphosphorylmethyl)-1-oxo-3,4-dihydroisoquinolin-6-yl]oxymethyl]-3-fluoro-allyl] carbamate (50 mg, 0.10 mmol) was dissolved in dichloromethane (5 mL), then trimethylbromosilane (0.11 mL, 0.82 mmol) was added to the solution, and the mixture was reacted at room temperature for 1 hour. The reaction solution was concentrated under reduced pressure to obtain the title compound (44 mg, yield 99%) as a white solid.

MS (ESI, pos. ion) m/z: 345.2 [M−99]$^+$.

Step 3) [6-[(E)-2-(aminomethyl)-3-fluoro-allyl oxy]-1-oxo-3,4-dihydroisoquinolin-2-yl]-methylphosphonic acid hydrochloride

[6-[(E)-2-[(tert-butoxycarbonylamino)methyl]-3-fluoro-allyloxy]-1-oxo-3,4-dihydroisoquinolin-2-yl]-methylphosphonic acid (44 mg, 0.099 mmol) was dissolved in ethanol (1 mL), then a solution of hydrogen chloride in ethyl acetate (3 mL, 3.0 mol/L) was added to the solution, and the mixture was reacted at room temperature for 1 hour. Dichloromethane (8 mL) was added to the reaction solution, the mixture was stirred for 20 minutes, then stood, and the supernatant was poured out. The remaining solid was concentrated in vacuum to obtain the title compound (25 mg, yield 66%, HPLC purity: 91.39%) as a white solid.

MS (ESI, pos. ion) m/z: 345.1 [M−Cl]$^+$.

$^1$H NMR (400 MHz, DMSO-d$_6$) δ (ppm) 8.31 (s, 3H), 7.82 (d, J=8.6 Hz, 1H), 7.33 (d, J=81.8 Hz, 1H), 7.03-6.87 (m, 2H), 4.70 (s, 2H), 4.38 (d, J=7.6 Hz, 2H), 3.78 (d, J=11.5 Hz, 2H), 3.60 (s, 2H), 2.95 (t, J=6.3 Hz, 2H).

Example 24 6-[(E)-2-(aminomethyl)-3-fluoro-allyloxy]-2-(2-diethoxyphosphorylethyl)-3,4-dihydroisoquinoline-1-one hydrochloride

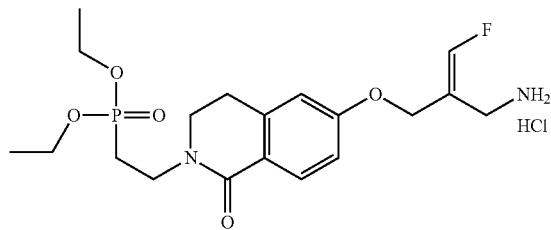

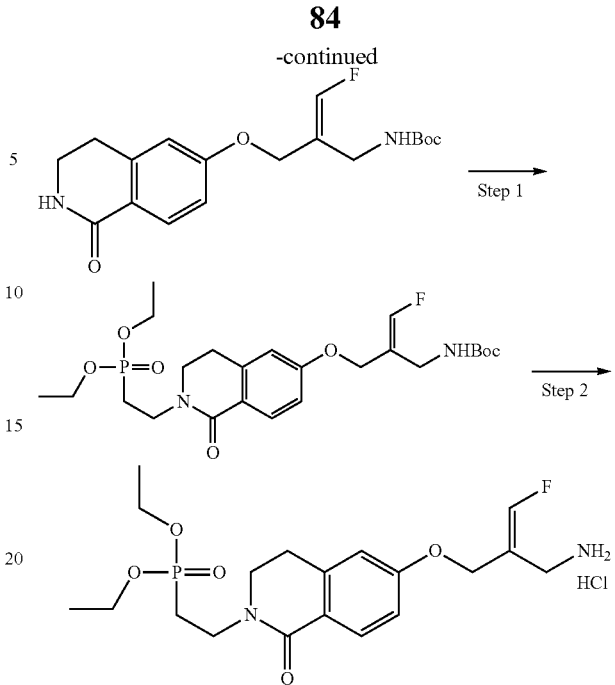

Step 1) Tert-butyl N-[(E)-2-[[2-(diethoxyphosphorylethyl)-1-oxo-3,4-dihydroisoquinolin-6-yl]oxymethyl]-3-fluoro-allyl] carbamate At 0° C., sodium hydride (23 mg, 0.58 mmol, 60% wt) was added into anhydrous tetrahydrofuran (8 mL), then tert-butyl N-[(E)-3-fluoro-2-[(1-keto-3,4dihydro-2H-isoquinoline-6-oxy)oxymethyl]allyl]carbamate (0.10 g, 0.29 mmol) was added to the solution, the mixture was reacted at room temperature for 10 minutes. To the resulting solution was added diethyl 2-bromoethylphosphonate (0.26 mL, 1.4 mmol) dropwise, the mixture was reacted at room temperature for 16 hours. The reaction was quenched by adding water (10 mL) and extracted with ethyl acetate (20 mL×3), and the combined organic phase was dried over anhydrous sodium sulfate, then filtered and concentrated by suction. The obtained residue was purified by silica gel column chromatography [methanol/ethyl acetate (v/v)=1/20] to obtain the title compound (0.10 g, yield 68%) as a colorless oil.

MS (ESI, pos. ion) m/z: 514.3 [M+H]$^+$;

$^1$H NMR (400 MHz, CDCl$_3$) δ (ppm) 7.98 (d, J=8.6 Hz, 1H), 6.87-6.83 (m, 1H), 6.73 (d, J=70.7 Hz, 1H), 6.67 (d, J=1.9 Hz, 1H), 4.76 (s, 1H), 4.47 (d, J=2.9 Hz, 2H), 4.11 (td, J=7.2, 4.9 Hz, 4H), 3.99 (d, J=4.9 Hz, 2H), 3.81-3.71 (m, 2H), 3.60 (t, J=6.6 Hz, 2H), 2.95 (dd, J=12.9, 6.3 Hz, 2H), 2.24-2.12 (m, 2H), 1.40 (s, 9H), 1.32 (t, J=7.1 Hz, 6H).

Step 2) 6-[(E)-2-(aminomethyl)-3-fluoro-allyl oxy]-2-(2-diethoxyphosphorylethyl)-3,4-dihydroisoquinoline-1-one hydrochloride Tert-Butyl N-[(E)-2-[[2-(diethoxyphosphorylethyl)-1-oxo-3,4-dihydroisoquinolin-6-yl]oxymethyl]-3-fluoro-allyl] carbamate (50 mg, 0.097 mmol) was dissolved in ethanol (1 mL), then a solution of hydrogen chloride in ethyl acetate (3 mL, 3.0 mol/L) was added to the solution, and the mixture was reacted at room temperature for 1 hour. To the reaction solution was added dichloromethane (8 mL). The resulting mixture was stirred for 20 minutes, then stood, and the supernatant was poured out. The remaining solid was concentrated in vacuum to obtain the title compound (44 mg, yield 100%, HPLC purity: 88.44%) as a white solid.

MS (ESI, pos. ion) m/z: 415.2 [M−Cl]$^+$;

$^1$H NMR (400 MHz, DMSO-d$_6$) δ (ppm) 8.23 (s, 3H), 7.81 (d, J=8.5 Hz, 1H), 7.33 (d, J=81.7 Hz, 1H), 6.95 (d, J=8.6 Hz, 1H), 6.91 (s, 1H), 4.68 (d, J=2.4 Hz, 2H), 4.10-3.95 (m, 4H), 3.62 (d, J=5.8 Hz, 4H), 3.55 (d, J=6.5 Hz, 2H), 2.95 (t, J=6.5 Hz, 2H), 2.18-2.04 (m, 2H), 1.24 (t, J=7.0 Hz, 6H).

Example 25 6-[(E)-2-(aminomethyl)-3-fluoro-allyloxy]-2-(2-methylsulfonylethyl)-3,4-dihydroisoquinoline-1-one hydrochloride

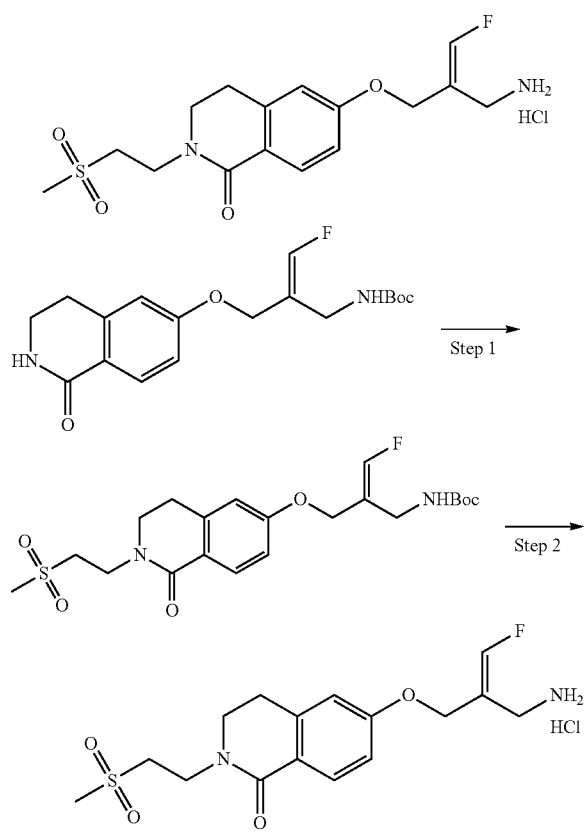

Step 1) Tert-butyl N-[(E)-3-fluoro-2-[[2-(2-methyl sulfonylethyl)-1-oxo-3,4-dihydroisoquinolin-6-yl]oxymethyl]allyl]carbamate At 0° C., sodium hydride (23 mg, 0.58 mmol, 60% wt) was added into anhydrous tetrahydrofuran (8 mL), then tert-butyl N-[(E)-3-fluoro-2-[(1-keto-3,4dihydro-2H-isoquinoline-6-oxy)oxymethyl]allyl]carbamate (0.10 g, 0.29 mmol) was added to the solution, the mixture was reacted at room temperature for 10 minutes. To the resulting mixture was added 2-bromoethyl methyl sulfone (27, 0.14 mmol) dropwise, and the mixture was reacted at room temperature for 16 hours. The reaction was quenched by adding water (10 mL) and extracted with ethyl acetate (20 mL×3). The combined organic phase was dried over anhydrous sodium sulfate, then filtered and concentrated by suction. The residue obtained was purified by silica gel column chromatography [100% ethyl acetate] to obtain the title compound (0.10 g, yield 68%) as a white solid.

MS (ESI, pos. ion) m/z: 401.1 [M−55]$^+$.

Step 2) 6-[(E)-2-(aminomethyl)-3-fluoro-allyloxy]-2-(2-methyl sulfonyl ethyl)-3,4-dihydroisoquinoline-1-one hydrochloride Tert-Butyl N-[(E)-3-fluoro-2-[[2-(2-methylsulfonylethyl)-1-oxo-3,4-dihydroisoquinolin-6-yl]oxymethyl]allyl]carbamate (0.10 g, 0.22 mmol) was dissolved in ethyl acetate (0.5 mL), then a solution of hydrogen chloride in ethyl acetate (2 mL, 3.0 mol/L) was added, and the mixture was reacted at room temperature for 1 hour. The reaction solution was concentrated under reduced pressure to obtain the title compound (79 mg, yield 92%, HPLC: 84.98%) as an off-white solid.

MS (ESI, pos. ion) m/z: 357.2 [M−Cl]$^+$;

$^1$H NMR (400 MHz, DMSO-d$_6$) δ (ppm) 8.41 (s, 3H), 7.81 (d, J=8.5 Hz, 1H), 7.32 (d, J=81.9 Hz, 1H), 6.99-6.89 (m, 2H), 4.71 (s, 2H), 3.86 (t, J=6.6 Hz, 2H), 3.58 (d, J=5.6 Hz, 4H), 3.45 (t, J=6.6 Hz, 2H), 3.04 (s, 3H), 2.96 (d, J=5.8 Hz, 2H).

Examples of Activity Tests

1. Determination of Inhibitory Activity of Human Recombinant SSAO/VAP-1

Test purpose: The following method is used to determine the inhibitory activity of the compounds in the examples of the present invention on human recombinant SSAO/VAP-1.

Test Materials:

Human recombinant SSAO/VAP-1 (VAP-1, human) was purchased from Sigma, Cat. No. SRP6241;

Amplex® Red Monoamine Oxidase Assay Kit was purchased from Invitrogen, Cat. No. A12214;

384-well plate was purchased from Corning, Cat. No. 6005174;

Amplex® Red Hydrogen PeroxidePeroxidase Assay Kit was purchased from Invitrogen, Cat. No. A22188.

Benzylamine hydrochloride was purchased from Sigma, Cat. No. B5136-25G;

DMSO (Dimethyl Sulfoxide) was purchased from Sigma, Cat. No. D2650-100ML;

Test Method:

The test compound was dissolved in DMSO and diluted 4 times to a total of 10 concentrations. In a 384-well plate, 25 μL of human recombinant SSAO/VAP-1 (1.6 μg/mL) was added into each well. 100 nL of test compounds at different concentrations were added to each well containing human recombinant SSAO/VAP-1, and the plate was incubated at room temperature for 30 min. After incubating for 30 min, 25 μL of Amplex® Red Monoamine Oxidase Assay Kit (a reaction mixture containing 200 μM Amplex Red reagent, 1 U/mL HRP and 1 mM benzylamine hydrochloride) was added into the corresponding wells, and the plate was incubated at room temperature in the dark for 60 min. After 60 min, PerkinElmer's Envision was used to read the fluorescence value (RFU) under excitation at 530-560 nm and emission at 590 nm. The graph was drawn using Graph Pad Prism 5 software to calculate the IC$_{50}$ value. Results were as shown in table 1:

TABLE 1

Inhibitory activity of the compounds provided in the embodiments of the present invention on human recombinant SSAO/VAP-1

| Example No. | SSAO/VAP-1 (Human Recombinant Protein) $IC_{50}$/nM |
|---|---|
| Example 1 | 6.29 |
| Example 2 | 2.20 |
| Example 4 | 3.70 |
| Example 6 | 4.12 |
| Example 7 | 11.10 |
| Example 8 | 1.0 |
| Example 18 | 8.661 |
| Example 19 | 4.011 |
| Example 21 | 11.75 |
| Example 24 | 3.67 |
| Example 25 | 3.375 |

The test results show that the compound of the present invention has a significant inhibitory effect on human recombinant SSAO/VAP-1.

2. Determination of Selective Inhibition of DAO (Diamine Oxidase)

Test purpose: The following method is used to determine the selective inhibitory activity of the compound of the present invention on DAO.

Test Materials:
Human recombinant DAO (Recombinant Human ABP-1/DAO) was purchased from R&D, Cat. No. 8298-AO;
Amplex® Red Hydrogen PeroxidePeroxidase Assay Kit was purchased from Invitrogen, Cat. No. A22188;
1,4-Diaminobutane dihydrochloride was purchased from Aladdin, Cat. No. D106194-25G.

Test Method:
The test compound was dissolved in DMSO and diluted 5 times to a total of 6 concentrations. In a 384-well plate, 24 μL of human recombinant DAO (1 μg/mL) was added into each well. 1 μL of test compounds at different concentrations were added to each well containing human recombinant DAO, and the plate was incubated at 37° C. for 30 min. After incubating for 30 min, 25 μL of Amplex® Red Hydrogen Peroxide Peroxidase Assay Kit (containing 100 μM Amplex® Red and 0.2 U/ml HRP) containing 1 M 1,4-butanediamine dihydrochloride was added into the corresponding wells, and the plate was incubated in the dark at 37° C. for 30 min. After 30 min, PHERAstar FSX microplate reader of BMG LABTECH was used to read the fluorescence value (RFU) under excitation at 540 nm and emission at 580 nm. The graph was drawn using Graph Pad Prism 5 software to calculate the $IC_{50}$ value. Results were as shown in table 2:

TABLE 2

The inhibitory activity of the compounds provided in the embodiments of the present invention on DAO

| Example No. | DAO $IC_{50}$/μM |
|---|---|
| Example 1 | >1 |
| Example 3 | >0.1 |
| Example 5 | >0.1 |
| Example 7 | >1 |
| Example 9 | >1 |
| Example 11 | >0.1 |
| Example 13 | >0.1 |
| Example 15 | >0.1 |
| Example 16 | >0.1 |
| Example 17 | >0.1 |
| Example 18 | >1 |
| Example 19 | >1 |
| Example 20 | >0.1 |
| Example 21 | >1 |
| Example 22 | >0.1 |
| Example 24 | >0.1 |
| Example 25 | >0.1 |

The test results show that the inhibition activity on DAO of the compounds of the present invention is far weaker than that on SSAO/VAP-1, indicating that the compounds of the present invention has high selectivity on SSAO/VAP-1.

3. Pharmacokinetic Determination of the Compounds of the Present Invention

Measurement purpose: The following method is used to determine the pharmacokinetics of the compounds of the present invention.

Test Materials:
Experimental reagents and test compounds: Propranolol (internal standard), methanol, ammonium acetate, $K_2$EDTA (potassium ethylenediamine tetraacetate), formic acid, acetonitrile, MTBE (methyl tert-butyl ether), Kollipho-rHS15 (polyethylene glycol 12 hydroxystearate), DMSO (dimethyl sulfoxide) are commercially available;
SD rat: male, 180-220 g, 7-8 weeks old, purchased from Hunan Slake Experimental Animal Co., Ltd.

Test Method:
1. Preparation of Test Compounds

Each test compound prepared was completely dissolved in a mixture of 5% DMSO+5% KolliphorHS 15+90% Saline according solubility property thereof.

2. Design of Animal Experiment

| Test compound | Compounds of examples of the invention |
|---|---|
| Animal grouping | Intravenous injection/I.V.: n = 3; blood collection time (hours/h): 0.083, 0.25, 0.5, 1, 2, 5, 7, 24 Oral/P.O.: n = 3; blood collection time (hours/h): 0.083, 0.25, 0.5, 1, 2, 5, 7, 24 |
| drug-delivery way | Intravenous: intravenous administration of hind legs and feet; oral administration: intragastric administration. |
| Blood collection method | Tail vein blood collection |
| Blood collection Anticoagulant | 200~400 μL/time point $K_2$EDTA |
| Plasma preparation | All samples were centrifuged at 10000 rpm, 4° C., for 2 minutes to separate plasma within 60 minutes. The samples were stored at −80° C. for testing. Back-up samples are stored for 1 month after the complete of the analysis. |
| Fasting situation | The SD rats were fasted for 15 hours before the administration, and they were allowed to drink freely. SD rats were fed 4 h after administration. |
| Stock solution solvent | Test compound: 20% DMSO; internal standard: Propranolol aqueous solution (100 ng/mL) |
| data processing | Pharmacokinetic parameters were calculated using a noncompartmental method by Win NonLin 6.1 software |

3. Animal Administration Dose Table

| Group | Gender | Number | Administration dose | Administration concentration | Administration volume |
|---|---|---|---|---|---|
| Intravenous injection I.V. | male | 3 | 1 mg/kg | 1 mg/mL | 1 mL/kg |
| Oral P.O. | male | 3 | 5 mg/kg | 1 mg/mL | 5 mL/kg |

4. Solution Preparation (1) Preparation of the test compound stock solution: an appropriate amount of test compound was precisely weighed, dissolved in DMSO, diluted to 1 mg/mL with acetonitrile, and shaken well to obtain the test compound stock solution, which was stored at −20° C. for use.

(2) Preparation of internal standard solution: a certain amount of 1mg/mL Propranolol stock solution was precisely drawn and diluted to 100 ng/mL with water.

5. Sample Analysis

The liquid-liquid extraction method was used to process the samples for chromatographic separation. On a triple quadrupole tandem mass spectrometer, quantitative analysis was performed using multiple reactive ion monitoring (MRM), and the concentration were calculated using instrument quantitative software.

6. Pretreatment of Plasma Samples

30 µL of plasma sample was accurately drawn, and added with 250 µL of internal standard. The mixture was mixed well by vortexing. The mixture was extracted once with 1 mL of MTBE, centrifuged at 13,000 rpm, 4° C. for 2 min, then 800 µL of supernatant was drawn, and evaporated in a 96-well nitrogen blower. The residue was re-dissolved with 150 µL of methanol/water (v/v=50/50), mixed by vortexing, and injected. The injection volume was 8 µL.

7. Preparation of Standard Samples

An appropriate amount of compound stock solution was accurately drawn, and diluted with acetonitrile to obtain standard series solution. 20 µL of each of the above standard series solutions was accurately drawn. 180 µL of blank plasma was added, and the mixture was mixed well by vortexing to prepare plasma samples equivalent to plasma concentrations of 3, 5, 10, 30, 100, 300, 1000, 3000, 5000, and 10000 ng/mL, which were all processed according to "pretreatment of plasma samples". Two samples were analyzed for each concentration to establish a standard curve.

8. Analysis Method

The content of the test compound in the plasma of rats after administration of different compounds was determined by LC/MS/MS method.

9. Data Processing

Pharmacokinetic parameters were calculated using a non-compartmental method by WinNonLin 6.1 software.

The test results show that the compounds of the present invention exhibit excellent pharmacokinetic properties when administered intravenously or orally, for example, good absorption and relatively high exposure. Specifically, the compounds of the present invention have higher $C_{max}$, $AUC_{last}$ and $AUC_{INF}$ in SD rats, indicating that the compounds of the present invention have a large exposure in rats and are well absorbed.

4. Pharmacodynamic Evaluation of the Compounds of the Present Invention

Test Materials:

Western diet: purchased from Research diet, article number: D12079B;

MCD diet: purchased from Nantong Trophy Feed Technology Co., Ltd., article number: TP3006R;

ALT, AST, ALP, TG; CHO, HDL, LDL and GLU: purchased from Roche, article numbers are: 20764957322, 20764949322, 03333701190, 20767107322, 03039773190, 04399803190, 03038866322 and 0440483190;

8-week-old male OB/OB mice: purchased from Jiangsu Jicui Yaokang Biotechnology Co., Ltd.;

8-week-old male db/db mice: purchased from Jiangsu Jicui Yaokang Biotechnology Co., Ltd.

A. Pharmacodynamic Evaluation of the Compound in the Non-Alcoholic Steatohepatitis GNASH) Model of OB/OB Mice Induced by Western Diet OB/OB mice were leptin gene-deficient mice, and the OB/OB mouse NASH model induced by Western diet is a commonly used NASH in vivo drug efficacy evaluation model. The animals experiment began after 1 week of acclimation. OB/OB mice were fed with Western diet, and the feed was changed three times a week (Monday, Wednesday, and Friday). The mice began to be administered with the drug in the fifth week after feeding, and they were administered orally once a day for 6 weeks. The entire experiment period was 10 weeks. During the experiment, the basic conditions of the animals were monitored every day, and the weight of the mice was recorded once a week. After the experiment, the rats were fasted overnight. After anesthetizing the mice, whole blood was collected from the orbit. The serum was obtained by centrifugation at 4° C., 4,000 rpm for 10 min, and stored at −80° C. The serum was used for the detection of ALT, AST, ALP, TG; CHO, HDL, LDL and GLU. The mice were dissected, and their livers were taken and weighed. The middle lobes of the livers were placed in EP tubes and stored at −80° C. for the determination of TG and CHO content in the livers. After the left lobes of livers were fixed in 10% formalin, HE staining was performed and NAS score was performed.

B. Pharmacodynamic Evaluation of the Compound in the Non-Alcoholic Steatohepatitis (NASH) Model of db/db Mice Induced by MCD Diet db/db Mice were leptin receptor gene-deficient mice, and the db/db mouse NASH model induced by MCD diet is a commonly used NASH in vivo drug efficacy evaluation model. The animals experiment began after 1 week of acclimation. db/db Mice were fed with MCD diet, and the feed was changed three times a week (Monday, Wednesday, and Friday). The mice were administered the drug while modeling, and they were administered orally once a day for 8 weeks. The entire experiment period was 8 weeks. During the experiment, the basic conditions of the animals were monitored every day, and the weight of the mice was recorded once a week. After the experiment, the rats were fasted overnight. After anesthetizing the mice, whole blood was collected from the orbit. The serum was obtained by centrifugation at 4° C., 4,000 rpm for 10 min, and stored at −80° C. The serum was used for the detection of ALT, AST, ALP, TG; CHO, HDL, LDL and GLU. The mice were dissected, and their livers were taken and weighed. The middle lobes of the livers were placed in EP tubes and stored at −80° C. for the determination of TG and CHO content in the livers. After the left lobes of livers were fixed in 10% formalin, HE staining was performed and NAS score was performed.

The test results show that the compounds of the present invention can effectively reduce the NAS score and the area of liver fibrosis.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the above terms throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I) or a stereoisomer, a geometric isomer, a tautomer, an N-oxide, a pharmaceutically acceptable salt thereof,

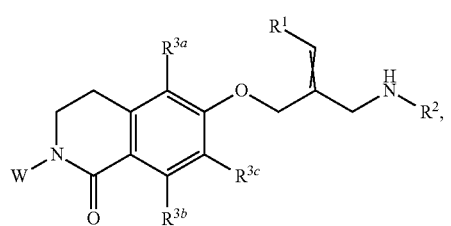

(I)

wherein, $R^1$ is F, Cl, Br or I;

$R^2$ is H, deuterium, $C_{1-6}$ alkyl, $C_{1-6}$ haloalkyl, $C_{3-6}$ cycloalkyl, 3-6 membered heterocyclyl, $C_{6-10}$ aryl, 5-6 membered heteroaryl or

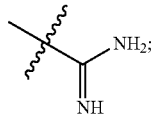

each of $R^{3a}$, $R^{3b}$ and $R^{3c}$ is independently H, deuterium, F, Cl, Br, I, CN, $NO_2$, —COOH, OH, $NH_2$, —C(=O)—$C_{1-6}$ alkyl, —C(=O)—$C_{1-6}$ alkoxy, $C_{1-6}$ alkyl, $C_{1-6}$ alkoxy, $C_{1-6}$ haloalkyl, $C_{1-6}$ haloalkoxy, hydroxy $C_{1-6}$ alkyl, amino $C_{1-6}$ alkyl, cyano $C_{1-6}$ alkyl, carboxy $C_{1-6}$ alkyl, $C_{3-6}$ cycloalkyl, 5-6 membered heterocyclyl, $C_{6-10}$ aryl or 5-6 membered heteroaryl;

W is -L-$R^4$ or —$(CR^aR^b)_t$—P(=O)($R^5$)($R^6$);

L is —$(CR^aR^b)_p$—C(=O)—$NR^c$—, —$(CR^aR^b)_q$—S—, —$(CR^aR^b)_q$—S(=O)—, —$(CR^aR^b)_s$—S(=O)$_2$—, —$(CR^aR^b)_q$—S(=O)$_2$—$NR^c$— or —$(CR^aR^b)_q$—S(=O)—$NR^c$—;

each of q, p, s and t is independently 0, 1, 2, 3, 4 or 5;

each of $R^a$, $R^b$ and $R^c$ is independently H, deuterium, F, Cl, Br, I, CN, $NO_2$, —COOH, OH, $NH_2$, $C_{1-6}$ alkyl, $C_{1-6}$ alkoxy, $C_{1-6}$ haloalkyl, $C_{1-6}$ haloalkoxy, hydroxy $C_{1-6}$ alkyl, amino $C_{1-6}$ alkyl, cyano $C_{1-6}$ alkyl, carboxyl $C_{1-6}$ alkyl, $C_{3-6}$ cycloalkyl, 3-6 membered heterocyclyl, $C_{6-10}$ aryl or 5-6 membered heteroaryl;

$R^4$ is H, deuterium, $C_{1-8}$ alkyl, $C_{2-6}$ alkenyl, $C_{2-6}$ alkynyl, $C_{1-6}$ haloalkyl, $C_{3-6}$ cycloalkyl, 3-6 membered heterocyclyl, $C_{6-10}$ aryl or 5-6 membered heteroaryl, wherein each of the $C_{1-8}$ alkyl, $C_{2-6}$ alkenyl, $C_{2-6}$ alkynyl, $C_{1-6}$ haloalkyl, $C_{3-6}$ cycloalkyl, 3-6 membered heterocyclyl, $C_{6-10}$ aryl and 5-6 membered heteroaryl is independently unsubstituted or substituted with 1, 2, 3 or 4 $R^y$;

or $R^c$ and $R^4$ together with the nitrogen atom to which they are attached, form 3-6 membered heterocyclyl or 5-6 membered heteroaryl, wherein each of 3-6 membered heterocyclyl and 5-6 membered heteroaryl is independently unsubstituted or substituted with 1, 2, 3 or 4 $R^y$;

each of $R^5$ and $R^6$ is independently OH, $NH_2$, $C_{1-6}$ alkyl, $C_{1-6}$ alkoxy, $C_{1-6}$ alkylamino, $C_{3-6}$ cycloalkyl, $C_{3-6}$ cycloalkyloxy, $C_{3-6}$ cycloalkylamino, 3-6 membered heterocyclyl, 3-6 membered heterocyclyloxy, 3-6 membered heterocyclylamino, $C_{6-10}$ aryl, $C_{6-10}$ aryloxy, $C_{6-10}$ arylamino, 5-6 membered heteroaryl, 5-6 membered heteroaryloxy or 5-6 membered heteroarylamino, wherein each of the $C_{1-6}$ alkyl, $C_{1-6}$ alkoxy, $C_{1-6}$ alkylamino, $C_{3-6}$ cycloalkyl, $C_{3-6}$ cycloalkyloxy, $C_{3-6}$ cycloalkylamino, 3-6 membered heterocyclyl, 3-6 membered heterocyclyloxy, 3-6 membered heterocyclylamino, $C_{6-10}$ aryl, $C_{6-10}$ aryloxy, $C_{6-10}$ arylamino, 5-6 membered heteroaryl, 5-6 membered heteroaryloxy and 5-6 membered heteroarylamino is independently unsubstituted or substituted with 1, 2, 3 or 4 $R^y$;

or $R^5$ and $R^6$ together with the phosphorus atom to which they are attached, form 3-6 membered heterocyclyl or 5-6 membered heteroaryl, wherein each of 3-6 membered heterocyclyl and 5-6 membered heteroaryl is independently unsubstituted or substituted with 1, 2, 3 or 4 $R^y$;

each $R^y$ is independently deuterium, F, Cl, Br, I, CN, $NO_2$, —COOH, OH, $NH_2$, —SH, —C(=O)—$C_{1-6}$ alkyl, —C(=O)—$C_{1-6}$ alkoxy, —S(=O)$_2$—$C_{1-6}$ alkyl, —S(=O)$_2$—$C_{1-6}$ alkylamino, $C_{1-6}$ alkyl, $C_{1-6}$ alkoxy, $C_{1-6}$ haloalkyl, $C_{1-6}$ haloalkoxy, hydroxy $C_{1-6}$ alkyl, amino $C_{1-6}$ alkyl, cyano $C_{1-6}$ alkyl, carboxy $C_{1-6}$ alkyl, $C_{3-6}$ cycloalkyl, 5-6 membered heterocyclyl, $C_{6-10}$ aryl or 5-6 membered heteroaryl.

2. The compound according to claim 1, wherein the $R^4$ is H, deuterium, $C_{1-6}$ alkyl, $C_{2-4}$ alkenyl, $C_{2-4}$ alkynyl, $C_{1-4}$ haloalkyl, $C_{3-6}$ cycloalkyl, 5-6 membered heterocyclyl, $C_{6-10}$ aryl or 5-6 membered heteroaryl, wherein each of the $C_{1-6}$ alkyl, $C_{2-4}$ alkenyl, $C_{2-4}$ alkynyl, $C_{1-4}$ haloalkyl, $C_{3-6}$ cycloalkyl, 5-6 membered heterocyclyl, $C_{6-10}$ aryl and 5-6 membered heteroaryl is independently unsubstituted or substituted with 1, 2, 3 or 4 $R^y$;

or $R^c$ and $R^4$ together with the nitrogen atom to which they are attached, form 5-6 membered heterocyclyl or 5-6 membered heteroaryl, wherein each of 5-6 membered heterocyclyl and 5-6 membered heteroaryl is independently unsubstituted or substituted with 1, 2, 3 or 4 $R^y$.

3. The compound according to claim 1, wherein the $R^4$ is H, deuterium, methyl, ethyl, n-propyl, isopropyl, n-butyl, isobutyl, tert-butyl, n-pentyl, n-hexyl, vinyl, allyl, propenyl, ethynyl, —$CHF_2$, —$CF_3$, —$CH_2CHF_2$, —$CH_2CF_3$, cyclopropyl, cyclobutyl, cyclopentyl, cyclohexyl, pyrrolidinyl, pyrazolidinyl, tetrahydrofuranyl, tetrahydrothienyl, tetrahydropyranyl, piperidinyl, morpholinyl, thiomorpholinyl, piperazinyl, phenyl, naphthyl, furanyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of the methyl, ethyl, n-propyl, isopropyl, n-butyl, isobutyl, tert-butyl, n-pentyl, n-hexyl, vinyl, allyl, propenyl, ethynyl, —CHF$_2$, —CF$_3$, —CH$_2$CHF$_2$, —CH$_2$CF$_3$, cyclopropyl, cyclobutyl, cyclopentyl, cyclohexyl, pyrrolidinyl, pyrazolidinyl, tetrahydrofuranyl, tetrahydrothienyl, tetrahydropyranyl, piperidinyl, morpholinyl, thiomorpholinyl, piperazinyl, phenyl, naphthyl, furanyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3 or 4 R$^y$;

or R$^c$ and R$^4$ together with the nitrogen atom to which they are attached, form pyrrolidinyl, pyrazolidinyl, imidazolidinyl, piperidinyl, morpholinyl, piperazinyl, pyrrolyl, pyridyl, pyrazolyl, imidazolyl, triazolyl, tetrazolyl, oxazolyl, isoxazolyl, oxadiazolyl, 1,3,5-triazinyl, pyrazinyl, thiazolyl or pyrimidinyl, wherein each of the pyrrolidinyl, pyrazolidinyl, imidazolidinyl, piperidinyl, morpholinyl, piperazinyl, pyrrolyl, pyridyl, pyrazolyl, imidazolyl, triazolyl, tetrazolyl, oxazolyl, isoxazolyl, oxadiazolyl, 1,3,5-triazinyl, pyrazinyl, thiazolyl and pyrimidinyl is independently unsubstituted or substituted with 1, 2, 3 or 4 R$^y$.

4. The compound according to claim 1, wherein each of the R$^5$ and R$^6$ is independently OH, NH$_2$, C$_{1-4}$ alkyl, C$_{1-4}$ alkoxy, C$_{1-4}$ alkylamino, C$_{3-6}$ cycloalkyl, C$_{3-6}$ cycloalkyloxy, C$_{3-6}$ cycloalkylamino, 5-6 membered heterocyclyl, 5-6 membered heterocyclyloxy, 5-6 membered heterocyclylamino, C$_{6-10}$ aryl, C$_{6-10}$ aryloxy, C$_{6-10}$ arylamino, 5-6 membered heteroaryl, 5-6 membered heteroaryloxy or 5-6 membered heteroarylamino, wherein each of the C$_{1-4}$ alkyl, C$_{1-4}$ alkoxy, C$_{1-4}$ alkylamino, C$_{3-6}$ cycloalkyl, C$_{3-6}$ cycloalkyloxy, C$_{3-6}$ cycloalkylamino, 5-6 membered heterocyclyl, 5-6 membered heterocyclyloxy, 5-6 membered heterocyclylamino, C$_{6-10}$ aryl, C$_{6-10}$ aryloxy, C$_{6-10}$ arylamino, 5-6 membered heteroaryl, 5-6 membered heteroaryloxy and 5-6 membered heteroarylamino is independently unsubstituted or substituted with 1, 2, 3 or 4 R$^y$;

or R$^5$ and R$^6$ together with the phosphorus atom to which they are attached, form 5-6 membered heterocyclyl or 5-6 membered heteroaryl, wherein each of 5-6 membered heterocyclyl and 5-6 membered heteroaryl is independently unsubstituted or substituted with 1, 2, 3 or 4 R$^y$.

5. The compound according to claim 1, wherein each of the R$^5$ and R$^6$ is independently OH, NH$_2$, methyl, ethyl, n-propyl, isopropyl, n-butyl, isobutyl, tert-butyl, methoxy, ethoxy, n-propyloxy, isopropyloxy, N-methylamino, N,N-dimethylamino, N-ethylamino, N,N-diethylamino, N-n-propylamino, N-isopropylamino, cyclopropyl, cyclobutyl, cyclopentyl, cyclohexyl, cyclopropyloxy, cyclobutyloxy, cyclopentyloxy, cyclo hexyloxy, N-cyclopropylamino, N,N-dicyclopropylamino, N-cyclobutylamino, N-cyclopentylamino, N-cyclohexylamino, 5-6 membered heterocyclyl, 5-6 membered heterocyclyloxy, 5-6 membered heterocyclylamino, phenyl, phenyloxy, N-phenylamino, 5-6 membered heteroaryl, 5-6 membered heteroaryloxy or 5-6 membered heteroarylamino, wherein each of the methyl, ethyl, n-propyl, isopropyl, n-butyl, isobutyl, tert-butyl, methoxy, ethoxy, n-propyloxy, isopropyloxy, N-methylamino, N,N-dimethylamino, N-ethylamino, N,N-diethylamino, N-n-propylamino, N-isopropylamino, cyclopropyl, cyclobutyl, cyclopentyl, cyclohexyl, cyclopropyloxy, cyclobutyloxy, cyclopentyloxy, cyclo hexyloxy, N-cyclopropylamino, N,N-dicyclopropylamino, N-cyclobutylamino, N-cyclopentylamino, N-cyclohexylamino, 5-6 membered heterocyclyl, 5-6 membered heterocyclyloxy, 5-6 membered heterocyclylamino, phenyl, phenyloxy, N-phenylamino, 5-6 membered heteroaryl, 5-6 membered heteroaryloxy and 5-6 membered heteroarylamino is independently unsubstituted or substituted with 1, 2, 3 or 4 R$^y$;

or R$^5$ and R$^6$ together with the phosphorus atom to which they are attached, form 5-6 membered heterocyclyl or 5-6 membered heteroaryl, wherein each of 5-6 membered heterocyclyl and 5-6 membered heteroaryl is independently unsubstituted or substituted with 1, 2, 3 or 4 R$^y$.

6. The compound according to claim 1, wherein each R$^y$ is independently deuterium, F, Cl, Br, I, CN, NO$_2$, —COOH, OH, NH$_2$, —SH, —C(=O)—C$_{1-4}$ alkyl, —C(=O)—C$_{1-4}$ alkoxy, —S(=O)$_2$—C$_{1-4}$ alkyl, —S(=O)$_2$—C$_{1-4}$ alkylamino, C$_{1-4}$ alkyl, C$_{1-4}$ alkoxy, C$_{1-4}$ haloalkyl, C$_{1-4}$ haloalkoxy, hydroxy C$_{1-4}$ alkyl, amino C$_{1-4}$ alkyl, cyano C$_{1-4}$ alkyl, carboxy C$_{1-4}$ alkyl, C$_{3-6}$ cycloalkyl, 5-6 membered heterocyclyl, C$_{6-10}$ aryl or 5-6 membered heteroaryl.

7. The compound according to claim 1, wherein each R$^y$ is independently deuterium, F, Cl, Br, I, CN, NO$_2$, —COOH, OH, NH$_2$, —SH, —C(=O)-methyl, —C(=O)-ethyl, —C(=O)-methoxy, —C(=O)-ethoxy, —S(=O)$_2$-methyl, —S(=O)$_2$-ethyl, —S(=O)$_2$-n-propyl, —S(=O)$_2$-isopropyl, —S(=O)$_2$-n-butyl, —S(=O)$_2$-tert-butyl, —S(=O)$_2$-methylamino, —S(=O)$_2$-ethylamino, —S(=O)$_2$-n-propylamino, —S(=O)$_2$-isopropylamino, —S(=O)$_2$-tert-butylamino, methyl, ethyl, n-propyl, isopropyl, n-butyl, isobutyl, tert-butyl, methoxy, ethoxy, n-propyloxy, isopropyloxy, —CHF$_2$, —CF$_3$, —CH$_2$CHF$_2$, —CH$_2$CF$_3$, trifluoromethoxy, hydroxymethyl, hydroxyethyl, aminomethyl, aminoethyl, cyanomethyl, cyanoethyl, carboxymethyl, cyclopropyl, cyclobutyl, cyclopentyl, cyclohexyl, 5-6 membered heterocyclyl, phenyl or 5-6 membered heteroaryl.

8. The compound according to claim 1, wherein each of R$^a$, R$^b$ and R$^c$ is independently H, deuterium, F, Cl, Br, I, CN, NO$_2$, —COOH, OH, NH$_2$, C$_{1-4}$ alkyl, C$_{1-4}$ alkoxy, C$_{1-4}$ haloalkyl, C$_{1-4}$ haloalkoxy, hydroxy C$_{1-4}$ alkyl, amino C$_{1-4}$ alkyl, cyano C$_{1-4}$ alkyl, carboxyl C$_{1-4}$ alkyl, C$_{3-6}$ cycloalkyl, 5-6 membered heterocyclyl, C$_{6-10}$ aryl or 5-6 membered heteroaryl.

9. The compound according to claim 1, wherein each of R$^a$, R$^b$ and R$^c$ is independently H, deuterium, F, Cl, Br, I, CN, NO$_2$, —COOH, OH, NH$_2$, methyl, ethyl, n-propyl, isopropyl, methoxy, ethoxy, —CHF$_2$, —CF$_3$, —CH$_2$CHF$_2$, —CH$_2$CF$_3$, trifluoromethoxy, hydroxymethyl, hydroxyethyl, aminomethyl, aminoethyl, cyanomethyl, carboxymethyl, cyclopropyl, cyclobutyl, cyclopentyl, cyclohexyl, 5-6 membered heterocyclyl, phenyl or 5-6 membered heteroaryl.

10. The compound according to claim 1, wherein the R$^2$ is H, deuterium, methyl, ethyl, n-propyl, isopropyl, n-butyl, isobutyl, tert-butyl, —CHF$_2$, —CF$_3$, —CH$_2$CHF$_2$, —CH$_2$CF$_3$, cyclopropyl, cyclobutyl, cyclopentyl, cyclohexyl, 5-6 membered heterocyclyl, phenyl, 5-6 membered heteroaryl or

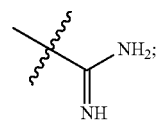

each of R$^{3a}$, R$^{3b}$ and R$^{3c}$ is independently H, deuterium, F, Cl, Br, I, CN, NO$_2$, —COOH, OH, NH$_2$, —C(=O)- methyl, —C(=O)-ethyl, —C(=O)-methoxy, —C(=O)-ethoxy, methyl, ethyl, n-propyl, isopropyl, n-butyl, isobutyl, tert-butyl, methoxy, ethoxy, —CHF$_2$, —CF$_3$, —CH$_2$CHF$_2$, —CH$_2$CF$_3$, trifluoromethoxy, hydroxymethyl, hydroxyethyl, aminomethyl, aminoethyl, cyanomethyl, carboxymethyl, cyclopropyl, cyclobutyl, cyclopentyl, cyclohexyl, 5-6 membered heterocyclyl, phenyl or 5-6 membered heteroaryl.

11. The compound according to claim 1 having one of the following structures:

(a)
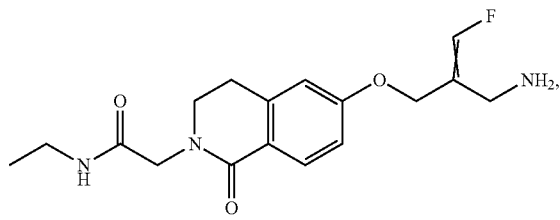

(b)
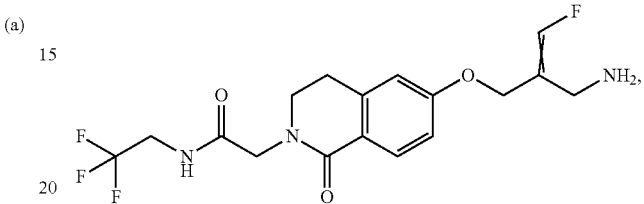

(c)
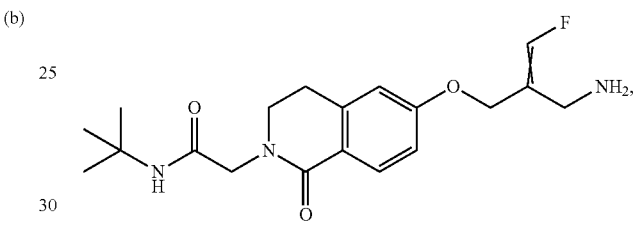

(d)
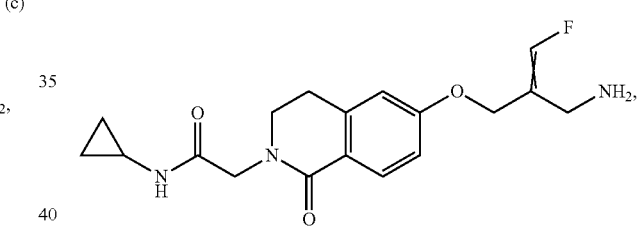

(e)
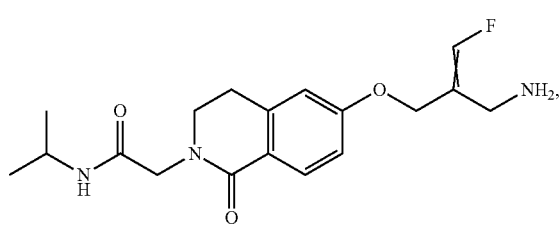

(f)
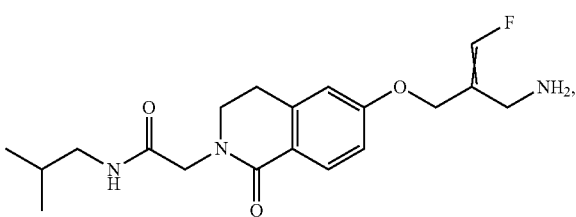

(g)
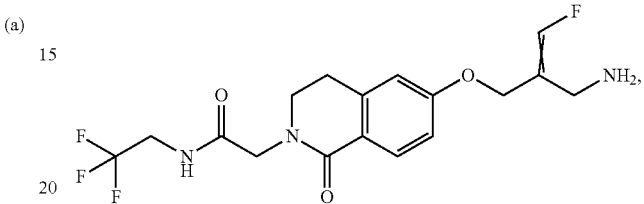

(h)
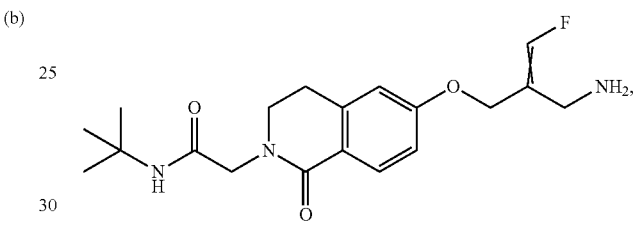

(i)
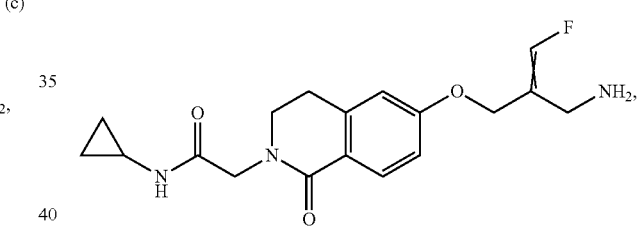

(j)
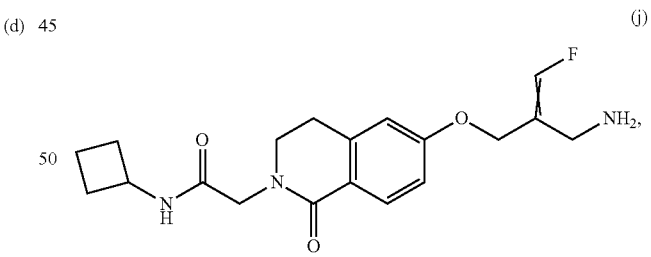

(k)
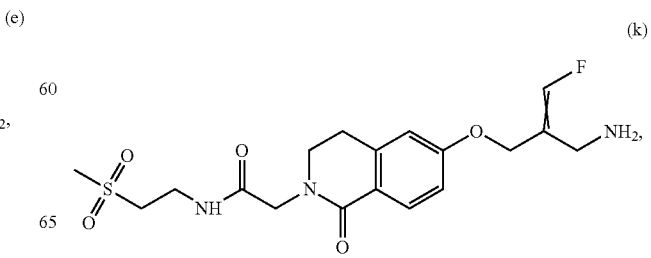

(l)
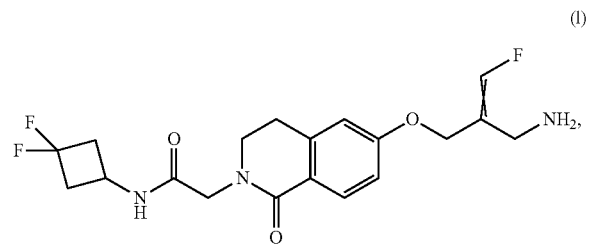
(m)
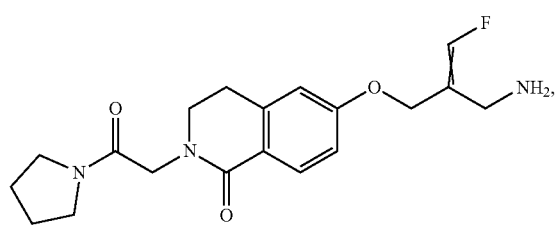
(n)
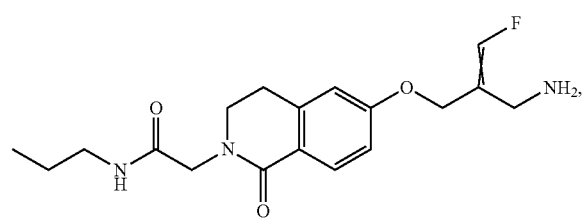
(o)
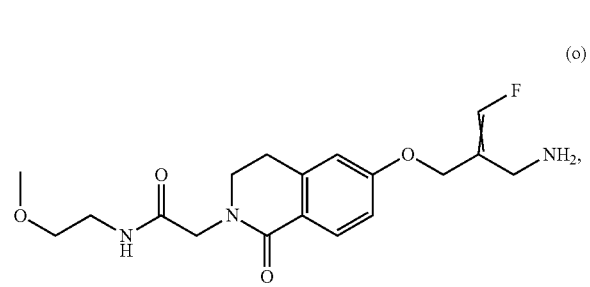
(p)
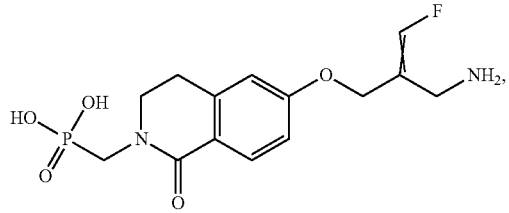
(q)
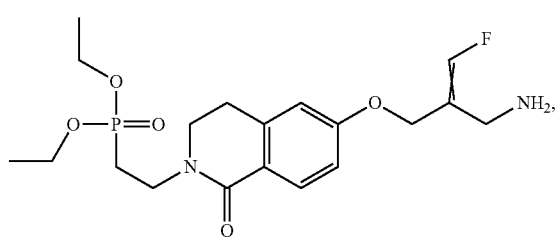
(r)
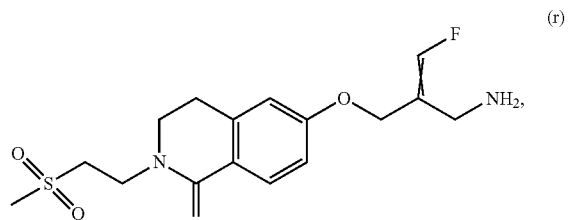
(s)
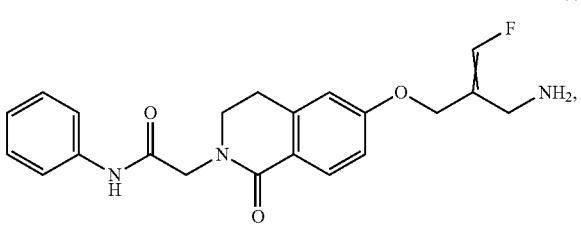
(t)
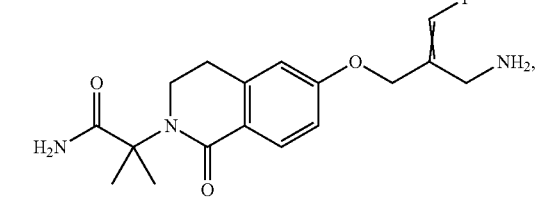
(u)
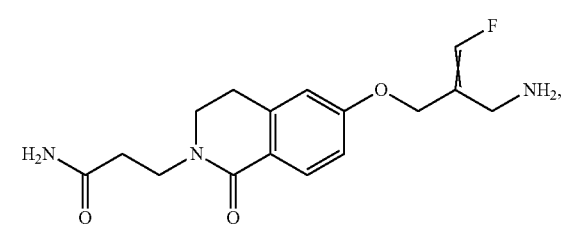
(v)
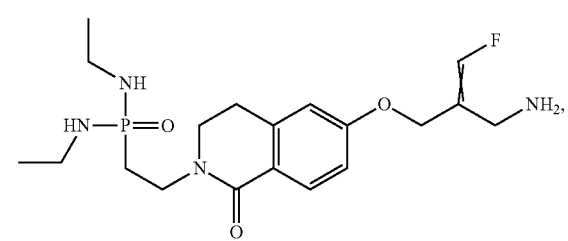
or a stereoisomer, a geometric isomer, a tautomer, an N-oxide, a pharmaceutically acceptable salt thereof.
12. The compound according to claim 1 having one of the following structures:
(1)
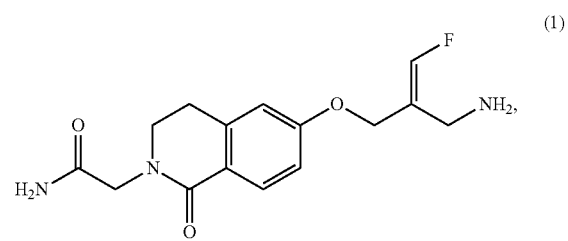

99
-continued
(2)
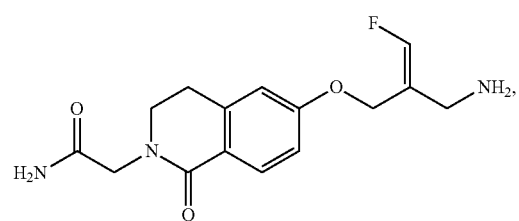
100
-continued
(9)
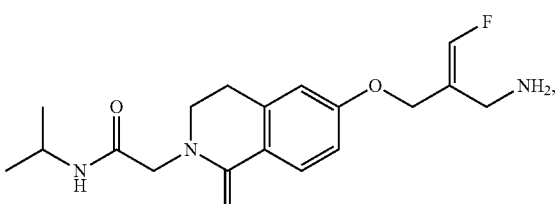
(3)
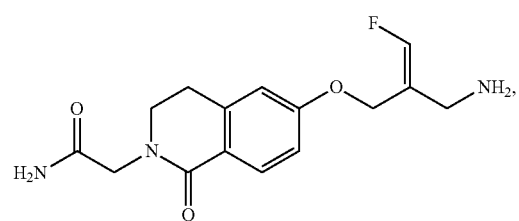
(10)
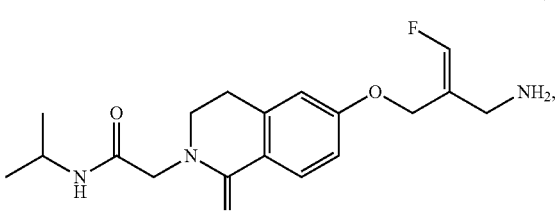
(4)
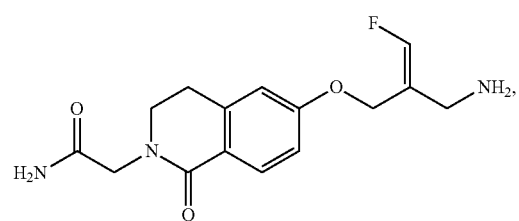
(11)
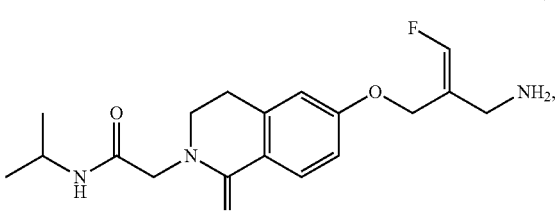
(5)
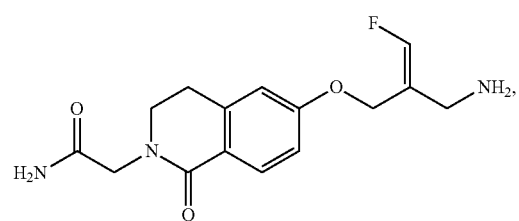
(12)
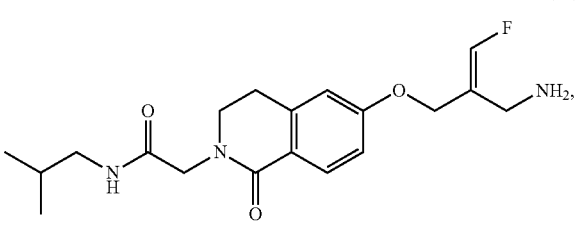
(6)
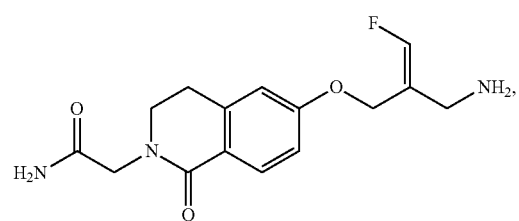
(13)
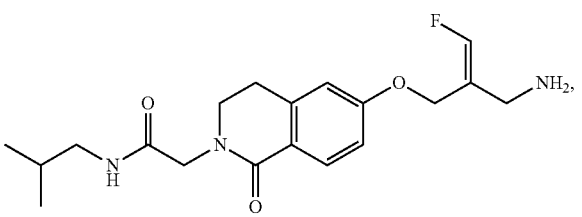
(7)
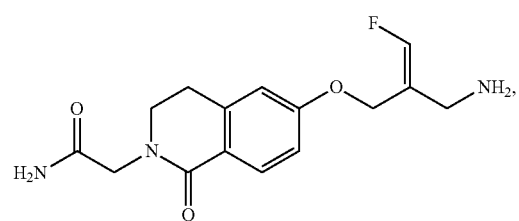
(14)
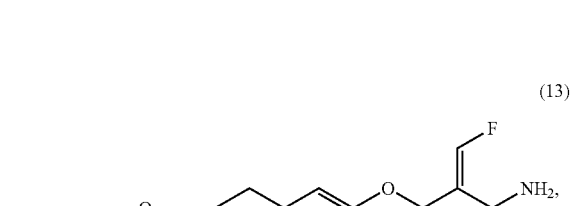
(8)
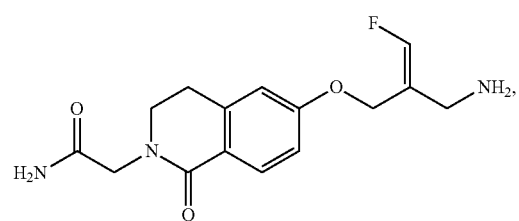

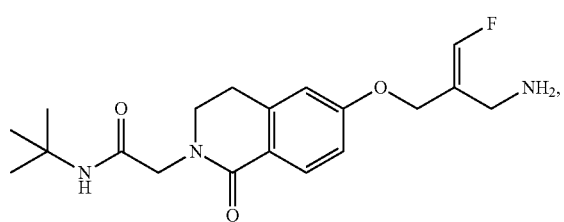
(15)
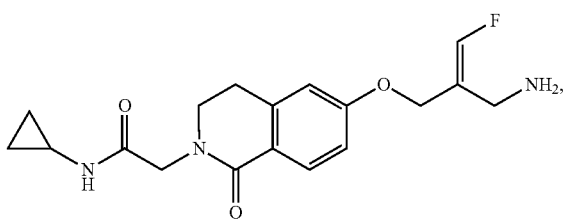
(16)
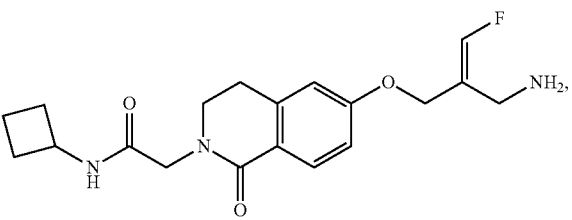
(17)
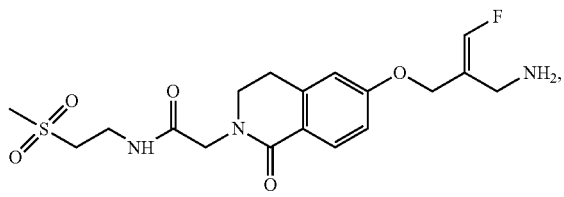
(18)
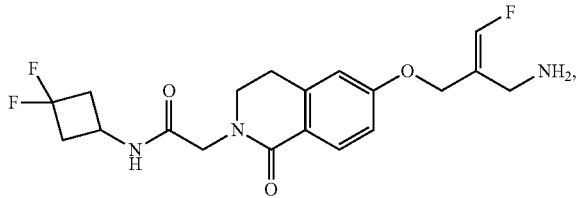
(19)
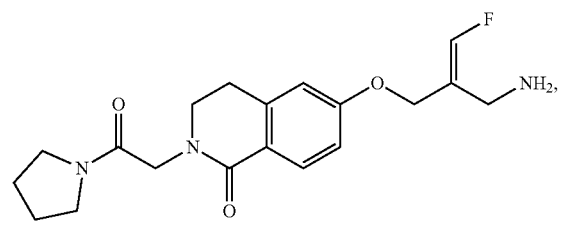
(20)
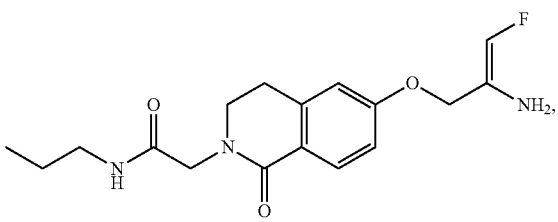
(21)
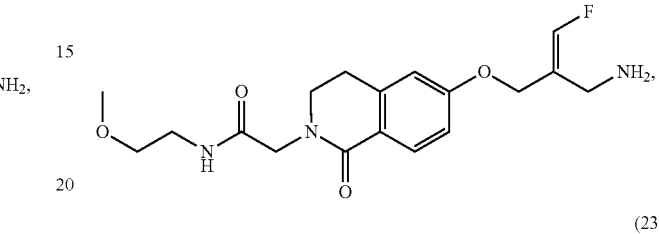
(22)
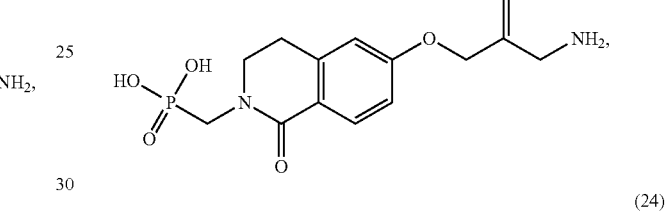
(23)
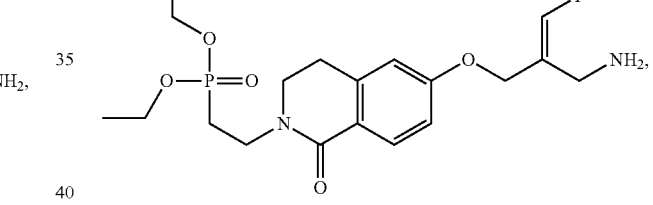
(24)
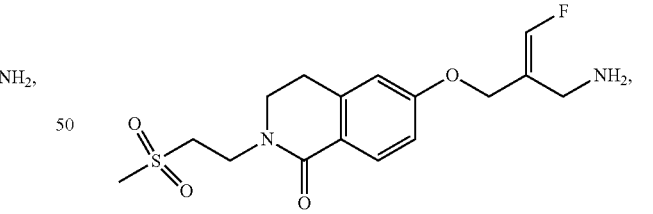
(25)
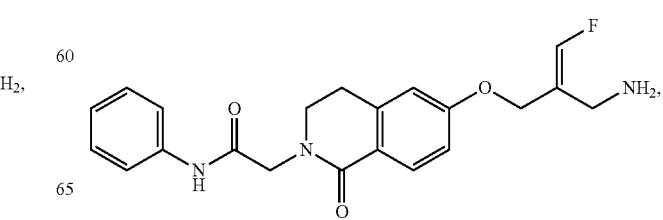
(26)

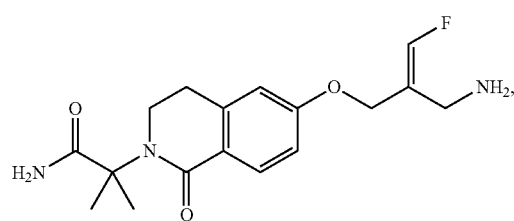
(27)
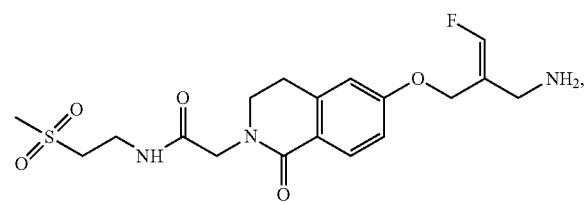
(33)
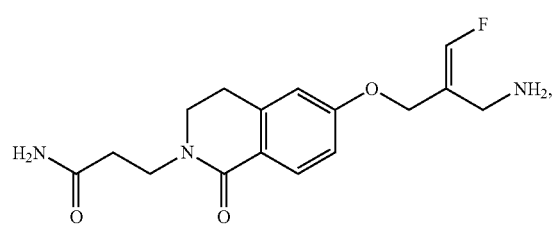
(28)
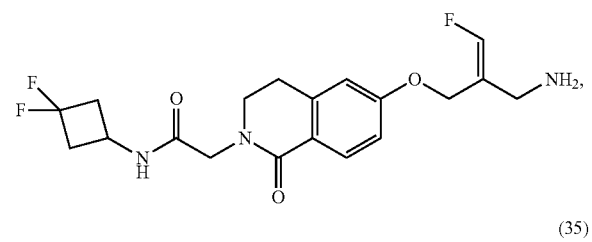
(34)
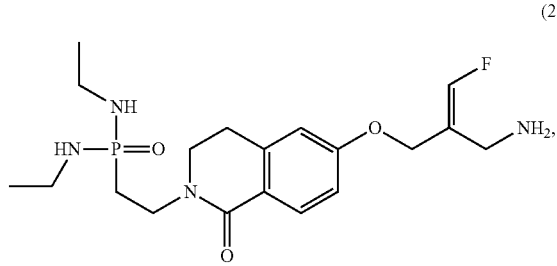
(29)
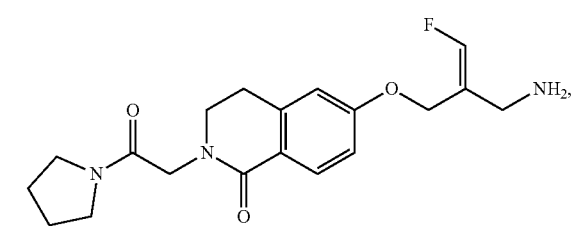
(35)
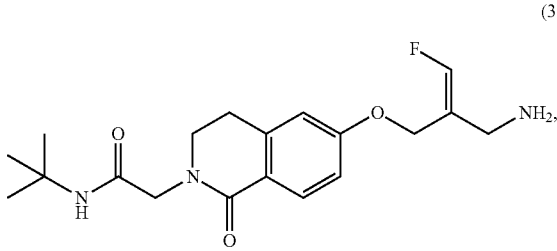
(30)
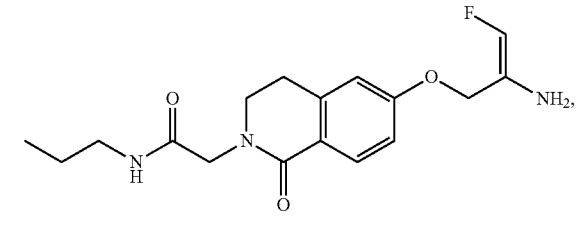
(36)
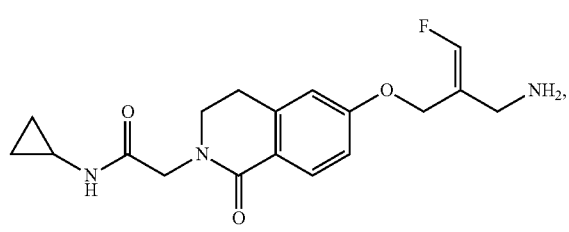
(31)
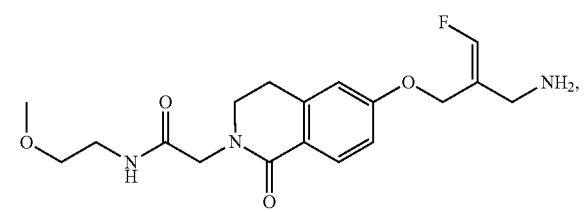
(37)
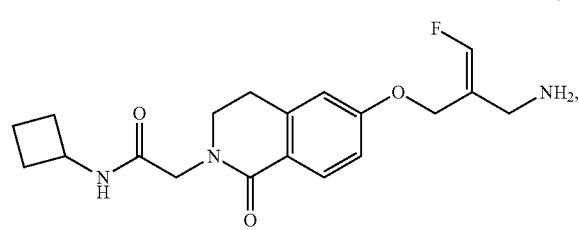
(32)
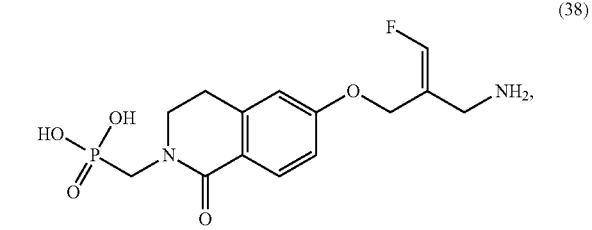
(38)

-continued

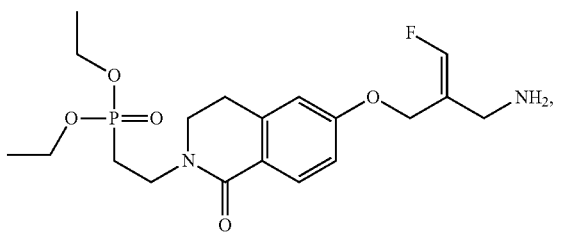
(39)

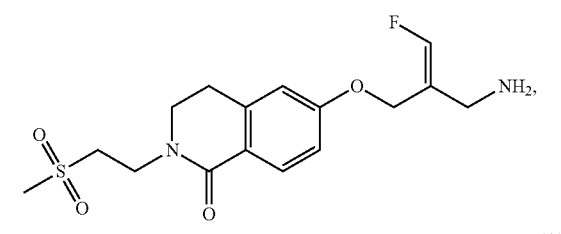
(40)

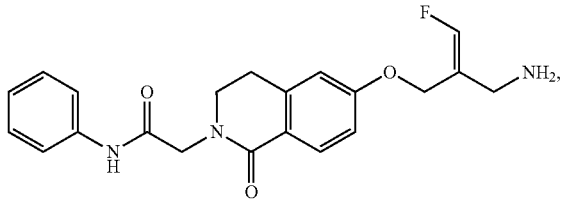
(41)

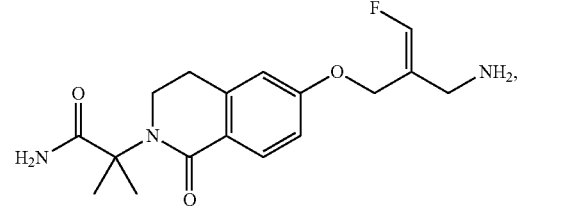
(42)

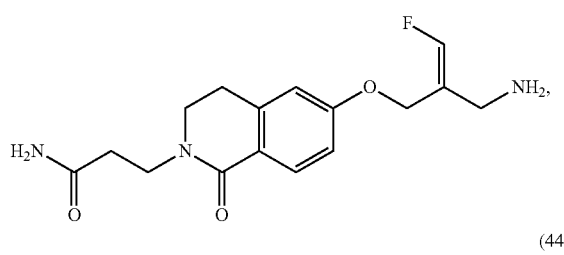
(43)

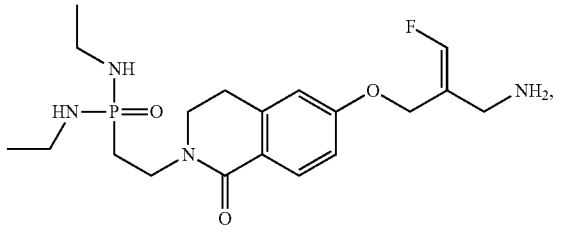
(44)

or a stereoisomer, a geometric isomer, a tautomer, an N-oxide, a pharmaceutically acceptable salt thereof.

13. The compound according to claim 1, wherein the pharmaceutically acceptable salt is hydrochloride, hydrobromide, phosphate, oxalate, maleate, tartrate, citrate, malate or methanesulfonate.

14. A pharmaceutical composition comprising the compound of claim 1, optionally, further comprising any one of pharmaceutically acceptable carriers, excipients, adjuvants, vehicles or combinations thereof.

15. A method of inhibiting SSAO/VAP-1, or treating or ameliorating a disease related to SSAO/VAP-1 protein or regulated by SSAO/VAP-1 in a subject comprising administering to the subject a therapeutically effective amount of the compound according to claim 1;
wherein the disease related to SSAO/VAP-1 protein or regulated by SSAO/VAP-1 is inflammation and/or a disease related to inflammation.

16. The method of claim 15, wherein the inflammation and/or a disease related to inflammation is arthritis, synovitis, a Crohn's disease, ulcerative colitis, an inflammatory bowel disease, hepatopathy, or an eye disease.

17. The method of claim 16, wherein the arthritis is osteoarthritis, rheumarthritis, rheumatoid arthritis or juvenile rheumatoid arthritis; the inflammatory bowel disease is irritable bowel syndrome; the hepatopathy is a liver autoimmune disease, autoimmune hepatitis, primary biliary cirrhosis, sclerosing cholangitis, autoimmune cholangitis, an alcoholic liver disease or a non-alcoholic fatty liver disease; the eye disease is uveitis, iritis, retinitis, autoimmune ophthalmia, inflammation driven by angiogenesis and/or lymphogenesis, macular degeneration;
wherein the non-alcoholic fatty liver disease is non-alcoholic simple fatty liver, non-alcoholic steatohepatitis, non-alcoholic fatty liver disease-related cryptogenic cirrhosis or primary liver cancer.

18. A method of inhibiting SSAO/VAP-1, or treating or lessening a disease related to SSAO/VAP-1 protein or regulated by SSAO/VAP-1 in a subject comprising administering to the subject a therapeutically effective amount of the pharmaceutical composition according to claim 14.

19. The method of claim 18, wherein the inflammation and/or a disease related to inflammation is arthritis, synovitis, a Crohn's disease, ulcerative colitis, an inflammatory bowel disease, hepatopathy, or an eye disease.

20. The method of claim 19, wherein the arthritis is osteoarthritis, rheumarthritis, rheumatoid arthritis or juvenile rheumatoid arthritis; the inflammatory bowel disease is irritable bowel syndrome; the hepatopathy is a liver autoimmune disease, autoimmune hepatitis, primary biliary cirrhosis, sclerosing cholangitis, autoimmune cholangitis, an alcoholic liver disease or a non-alcoholic fatty liver disease; the eye disease is uveitis, iritis, retinitis, autoimmune ophthalmia, inflammation driven by angiogenesis and/or lymphogenesis, macular degeneration;
wherein the non-alcoholic fatty liver disease is nonalcoholic simple fatty liver, nonalcoholic steatohepatitis, non-alcoholic fatty liver disease-related cryptogenic cirrhosis or primary liver cancer.

* * * * *